(12) United States Patent
Yoshioka et al.

(10) Patent No.: US 7,460,698 B2
(45) Date of Patent: Dec. 2, 2008

(54) ULTRASONIC PICTURE PROCESSING METHOD AND ULTRASONIC PICTURE PROCESSING APPARATUS

(75) Inventors: Hideki Yoshioka, Nishinomiya (JP); Mutsumi Watanabe, Kobe (JP); Mayumi Yuasa, Kobe (JP); Masahide Nishiura, Osaka (JP)

(73) Assignee: Kabushiki Kaisha Toshiba, Kawasaki-shi (JP)

( * ) Notice: Subject to any disclaimer, the term of this patent is extended or adjusted under 35 U.S.C. 154(b) by 812 days.

(21) Appl. No.: 11/026,015

(22) Filed: Jan. 3, 2005

(65) Prior Publication Data
US 2005/0111717 A1    May 26, 2005

Related U.S. Application Data

(60) Continuation of application No. 09/778,097, filed on Feb. 7, 2001, now Pat. No. 6,859,548, which is a division of application No. 08/937,007, filed on Sep. 24, 1997, now abandoned.

(30) Foreign Application Priority Data

| Sep. 25, 1996 | (JP) | ................................... | 8-253188 |
| Sep. 26, 1996 | (JP) | ................................... | 8-254498 |
| Sep. 26, 1996 | (JP) | ................................... | 8-254603 |
| Sep. 26, 1996 | (JP) | ................................... | 8-254604 |

(51) Int. Cl.
*G06K 9/00*    (2006.01)
(52) U.S. Cl. .................. 382/128; 382/131; 382/132
(58) Field of Classification Search ................ 382/100, 382/128, 131, 132; 128/922, 200.16, 916; 250/455; 348/699; 600/407, 437, 449, 443, 600/453
See application file for complete search history.

(56) References Cited

U.S. PATENT DOCUMENTS

| 4,337,661 A | 7/1982 | Kretz |
| 4,729,019 A | 3/1988 | Rouvrais |
| 4,747,146 A | 5/1988 | Nishikawa et al. |

(Continued)

FOREIGN PATENT DOCUMENTS

EP    0 268 370 A3    5/1988

(Continued)

OTHER PUBLICATIONS

Takeshi Hozumi et al. "Echocardiographic Estimation of Left Ventricular Cavity Area with a Newly Developed Automated Contour Tracking Method", Journal of the American Society of Echocardiography, vol. 10, iss 8, pp. 822-829, Published Oct. 1997.*

U.S. Appl. No. 11/203,064, filed Aug. 15, 2005, Nishiura.

*Primary Examiner*—Brian Q Le
(74) *Attorney, Agent, or Firm*—Oblon, Spivak, McClelland, Maier & Neustadt, P.C.

(57) ABSTRACT

An ultrasonic picture processing method comprising the steps of extracting contour information of a target from respective frame pictures of an ultrasonic moving image, dividing the extracted contour information into a plurality of regions at a preset interval, comparing the divided contour information parts with one another and making a predetermined determination of the ultrasonic moving pictures based on the comparison results.

10 Claims, 30 Drawing Sheets

U.S. PATENT DOCUMENTS

| | | |
|---|---|---|
| 5,239,591 A | 8/1993 | Ranganath |
| 5,353,354 A | 10/1994 | Keller et al. |
| RE34,974 E | 6/1995 | Terashima |
| 5,570,430 A * | 10/1996 | Sheehan et al. ............ 382/128 |
| 5,601,084 A | 2/1997 | Sheehan et al. |
| 6,236,738 B1 | 5/2001 | Zhu et al. |
| 6,429,457 B1 | 8/2002 | Berggren et al. |
| 6,432,739 B1 | 8/2002 | Gudesen et al. |
| 6,449,184 B2 | 9/2002 | Kato et al. |
| 6,459,095 B1 | 10/2002 | Heath et al. |
| 6,461,916 B1 | 10/2002 | Adachi et al. |
| 6,473,351 B2 | 10/2002 | Tomanek et al. |
| 6,487,106 B1 | 11/2002 | Kozicki et al. |
| 6,621,740 B2 | 9/2003 | Hosogane et al. |
| 6,627,944 B2 | 9/2003 | Mandell et al. |
| 6,635,914 B2 | 10/2003 | Kozicki et al. |
| 6,670,637 B2 | 12/2003 | Yamazaki et al. |
| 6,781,868 B2 | 8/2004 | Bulovic et al. |
| 2005/0111717 A1 | 5/2005 | Yoshioka et al. |

FOREIGN PATENT DOCUMENTS

| | | |
|---|---|---|
| EP | 0 385 688 A2 | 9/1990 |
| EP | 0 727 822 A2 | 8/1996 |
| JP | 59-155234 | 9/1984 |
| JP | 61-206083 | 9/1986 |
| JP | 62-269276 | 11/1987 |
| JP | 2-206443 | 8/1990 |
| JP | 4-84957 | 3/1992 |
| JP | 4-241849 | 8/1992 |
| JP | 4-270983 | 9/1992 |
| JP | 5-184577 | 7/1993 |
| JP | 5-261095 | 10/1993 |
| JP | 6-114059 | 4/1994 |
| JP | 6-285064 | 10/1994 |
| JP | 7-106440 | 4/1995 |
| JP | 7-192111 | 7/1995 |
| JP | 7-249115 | 9/1995 |
| JP | 7-250834 | 10/1995 |
| JP | 7-303642 | 11/1995 |
| JP | 8-117236 | 5/1996 |
| JP | 8-190634 | 7/1996 |
| JP | 8-206117 | 8/1996 |
| RU | 2071126 C1 | 12/1996 |

* cited by examiner

CONTOUR REGION

DISPLAY REGION

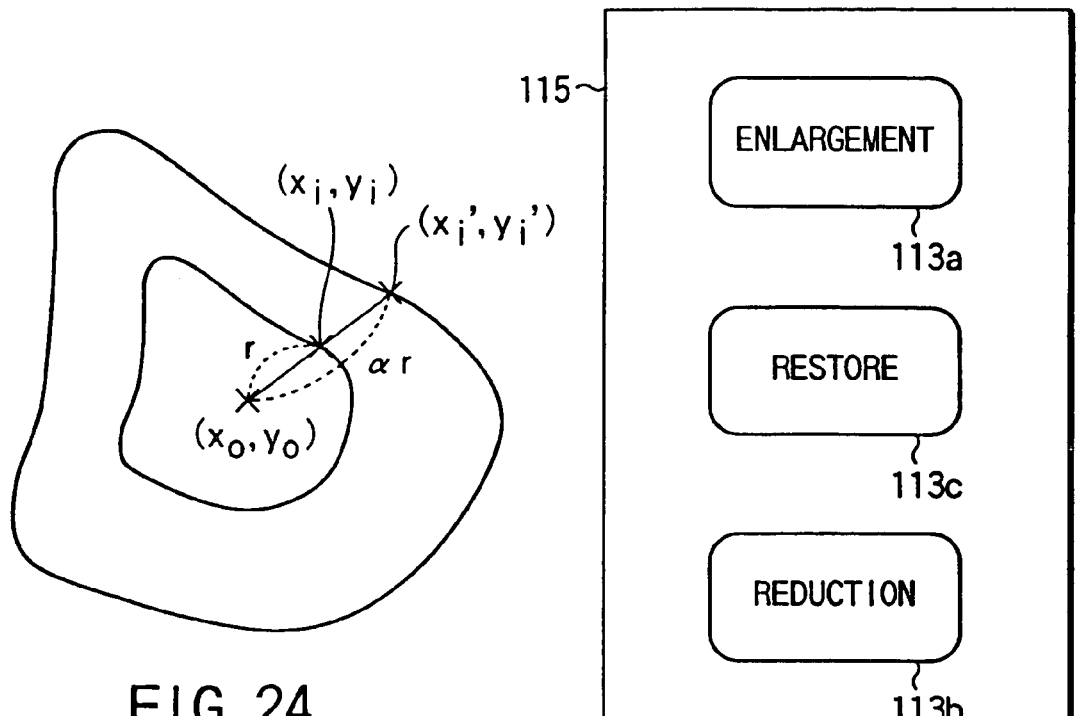
FIG. 24
FIG. 25
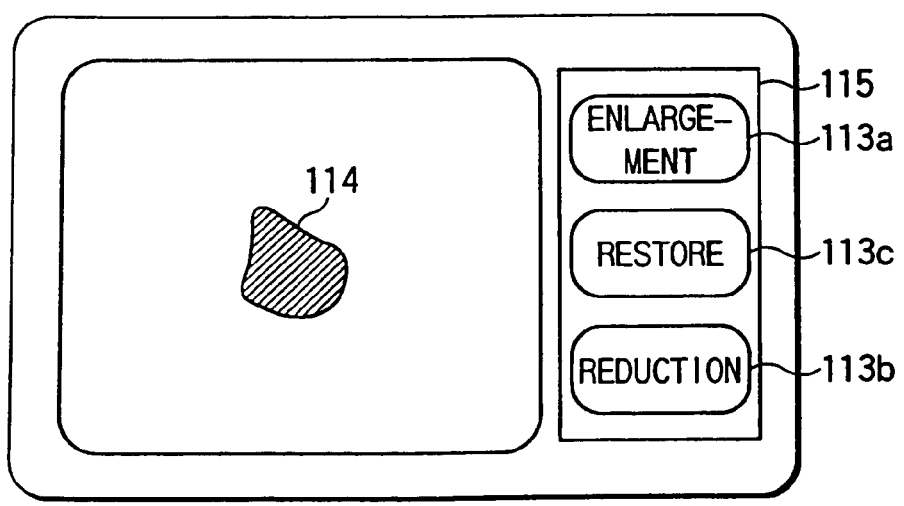
FIG. 26

EXTRACTED HEART CONTOUR $$\left(\text{VOLUME } V = \frac{\pi}{4} \sum_{i=1}^{N} r_i \cdot d\right)$$

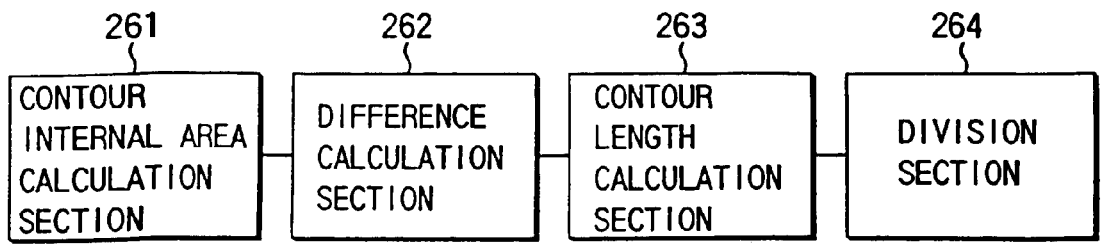
FIG. 47
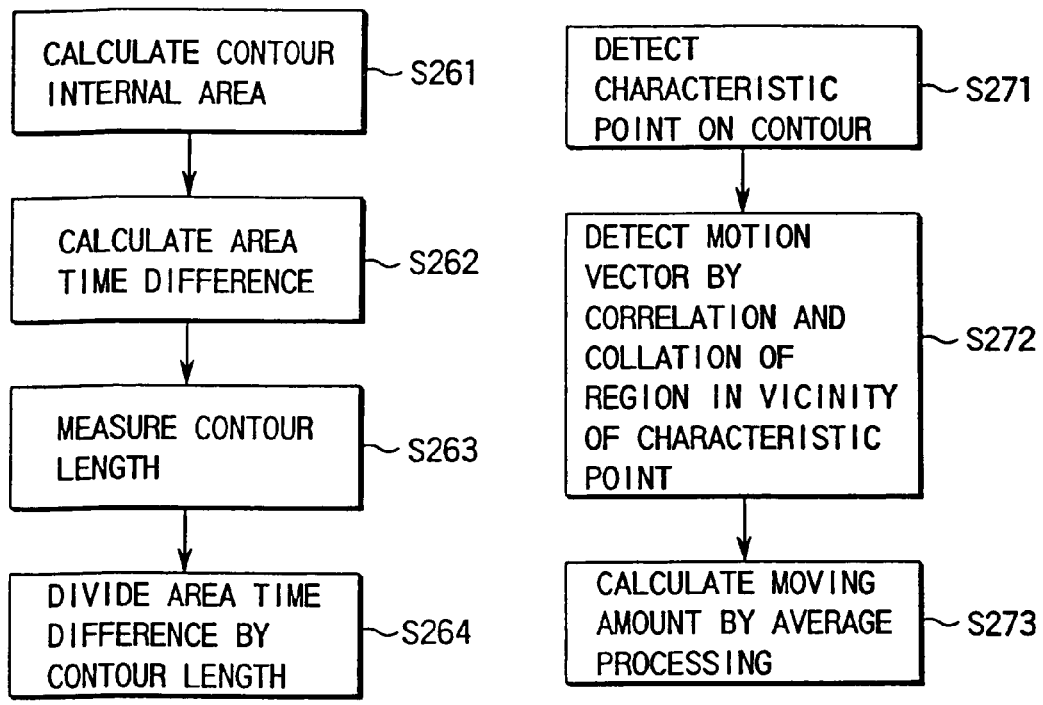
FIG. 48
FIG. 50
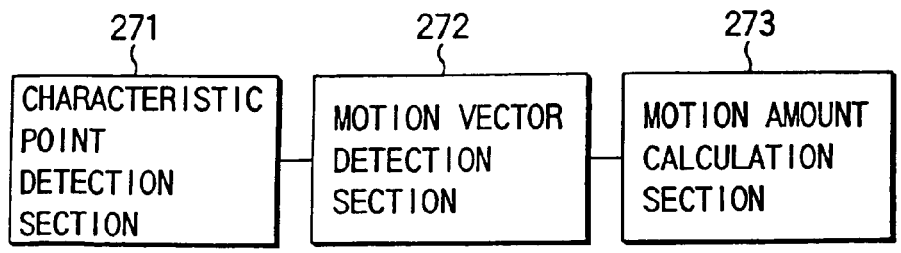
FIG. 49

ULTRASONIC PICTURE PROCESSING METHOD AND ULTRASONIC PICTURE PROCESSING APPARATUS

CROSS-REFERENCES TO RELATED APPLICATIONS

This application is a continuation of and claims the benefit of priority under 35 USC § 120 from U.S. application Ser. No. 09/778,097, filed Feb. 7, 2001 now U.S. Pat. No. 6,859,548, allowed, which is a division of U.S. Ser. No. 08/937,007, filed Sep. 24,1997, now abandoned. This application also is based upon and claims the benefit of priority under 35 USC § 119 from Japanese Patent Application Nos. 8-253188, filed Sep. 25, 1996; 8-254498, filed Sep. 26, 1996; 8-254603, filed Sep. 26, 1996; and 8-254604, filed Sep. 26, 1996, the entire contents of which are incorporated herein by reference.

BACKGROUND OF THE INVENTION

The present invention relates to an ultrasonic picture processing method and an ultrasonic picture processing apparatus for determining and collecting pictures which are important to the diagnosis of a disease and which are not affected by the movement of a subject's body and by the movement of inspector's hands, from ultrasonic pictures obtained by an ultrasonic diagnosis apparatus, and to an ultrasonic picture processing apparatus.

The present invention also relates to an picture processing apparatus for extracting the contour of a target and displaying a picture capable of determining whether or not the extracted picture is fitted to the target.

In recent years, as people's eating habits are improving, the number of people suffering from diseases such as obesity and hypertension is increasing in Japan. Since the mortality rate of cardiac diseases resulting from these diseases is a second highest next to cancer, they are becoming more and more serious problems. In the diagnosis of a cardiac disease, an electrocardiogram is used as a primary diagnosis method. For further detailed picture-using diagnosis, diagnosis using an ultrasonic diagnosis apparatus is widely applied due to convenience and low cost (compared to other diagnosis apparatuses such as X-ray CT, MRI and PET).

When diagnosing of a cardiac disease using the ultrasonic diagnosis apparatus, real-time moving pictures obtained by the apparatus are used in most cases. A doctor observes the movement of the cardiac wall of a patient for one piece of diagnostic information and diagnoses whether the patient's heart is abnormal. In case of a cardiac disease such as cardiac infarction and stenocardia, the abnormal movement of the cardiac wall is observed. It is desirable that such observation is conducted while parts other than the to-be-observed heart are static. This is because it is necessary to find out an abnormally moving region within the incessantly moving cardiac wall and to make a precise diagnosis.

Meanwhile, in case of an picture diagnosis by using the ultrasonic diagnosis apparatus, a system for collecting pictures by applying an ultrasonic probe to a subject is adopted. In this system, not only the patient but also the ultrasonic probe is not fixed and it is possible to freely change an observed region. Such a system is advantageous in convenience and the degree of freedom. However, if the movement of the heart is observed using this system, pictures tend to be blurred due to the movement of the subject's body and the movement of the inspector's hands. Even if pictures are collected while carefully preventing the blur of pictures, it is not clear whether or not pictures not blurred and suited for diagnosis can be obtained and the inspector needs to determine whether or not the pictures are appropriate. This determination lacks objectivity and causes an increase in the burden on the inspector. Such a system cannot expect effective diagnosis and may increase diagnosis time.

As described above, if making a diagnosis of a heart by using the ultrasonic diagnosis apparatus, it is necessary to pay attention to collecting blur-free pictures suited for diagnosis. The determination whether blur-free pictures have been obtained depends on the inspector, which disadvantageously lacks objectivity and imposes a burden on the inspector.

Moreover, since such information as to whether pictures useful for the diagnosis have been collected cannot be obtained, effective diagnosis cannot be conducted and more time is required for the diagnosis.

Furthermore, if movements of ultrasonic pictures of the heart are analyzed on various points of the heart, they are considered beneficial to the various diagnoses of cardiac functions. To this end, if movement states of respective parts can be tracked by extracting contours of the pictures, states of functions of the parts of the heart can be properly grasped and more beneficial diagnosis can be expected.

However, according to the conventional method of displaying contours of the heart obtained as ultrasonic pictures, the extracted contours are merely superimposed over original pictures or displayed completely differently. Due to this, it is difficult to determine whether the extracted contours are correct or not and it is therefore impossible to track states of movements of various parts of the heart. It goes without saying that the conventional method cannot be applied to the grasp of more detailed states of cardiac functions.

In addition, as software for drawing, coloring and filtering, there is computer graphic software (so-called a draw tool). Using the draw tool on a calculator, it is possible to form a graphic such as a contour manually and to modify, scale and color the manually formed contour. The draw tool, however, lacks functions such as comparison of a target and the picture of the target by superimposing the picture over the target and analysis of time series shape changes. Due to this, the draw tool cannot be applied to the evaluation of the accuracy of the contour extraction result and the analysis of the movement state of the moving target using contour lines of the picture of the target as described above.

It is therefore an object of the present invention to provide an ultrasonic picture processing method and an ultrasonic picture processing apparatus capable of determining and collecting pictures which are important to the diagnosis of a disease and are not affected by the movement of the subject's body or the movement of inspector's hands, from ultrasonic pictures obtained by the ultrasonic diagnosis apparatus.

It is also another object of the present invention to provide an ultrasonic picture processing method and an ultrasonic picture processing apparatus capable of easily determining whether extracted contours are correct, capable of tracking and analyzing movement states of various parts from the extracted contour information and capable of making use of the result for a diagnosis.

It is another object of the present invention to provide a picture processing apparatus and a picture processing method capable of automatically calculating a terminal diastole period area or volume and a terminal systole period area or volume, capable of lessening a burden to the inspector and capable of obtaining an objective, accurate inspection result.

It is another object of the present invention to provide a cardiac function analysis support apparatus and a cardiac function analysis support method of precisely associating cardiac wall contours in various time phases to allow information calculated from contour information to be displayed in the form which can be easily evaluated and thereby allow local movement states of the cardiac wall to be easily evaluated.

BRIEF SUMMARY OF THE INVENTION

The present invention provides an ultrasonic picture processing method and an ultrasonic picture processing apparatus wherein contour information of a target is extracted from ultrasonic moving picture information, the contour information is sampled at preset time intervals for generating a plurality of time series contour data, and the contour data is compared with other contour data, respectively to output comparison results.

The present invention provides an ultrasonic picture processing method and an ultrasonic picture processing apparatus wherein contour information of a target is extracted from ultrasonic moving picture information, the contour information is sampled at preset time intervals to generate a plurality of time series contour data, and the contour data is sequentially compared with other adjacent contour data, respectively, to make a predetermined determination of ultrasonic moving pictures based on comparison results.

The present invention provides a picture processing apparatus and a picture processing method having functions of extracting the contour of a target on a picture, superimposing the extracted contour over the target on the picture and using, as the displayed contour, a dotted line or a contour line in at least a desired portion.

The contour of the target on the picture is extracted. A display picture is generated by superimposing the extracted contour, which is indicated by a dotted line, over the target on the picture or by superimposing the extracted contour over the target on the picture only in a required region, and is then outputted. That is, the contour is indicated by a dotted line or part of the contour, such as an upper half of the contour and a right half of the contour, is displayed. In this way, it is possible to display the contour to the extent that the entire contour can be estimated only from information about the displayed portion. As a result, the shape of the extracted contour and that of the target can be easily compared.

The present invention also provides a picture processing apparatus comprising means for operating a position command and a movement command and means for extracting the contour of the target on the picture, generating a display picture so as to display the extracted contour and the target by superimposing the extracted contour over the target on the picture and generating a display picture so as to temporarily change the shape of or temporarily move the position of part of the contour including a portion indicated by the position command operation to thereby display the part of the contour together with the target on the picture.

The contour of the target on the picture is extracted. The extracted contour is superimposed over the target on the picture to thereby become a display picture. In addition, by operating a position command, the desired position of the contour is indicated. By operating a movement command, the movement of the contour is indicated. In accordance with these commands, a display picture is changed such that the entire contour or part of the contour including a portion indicated by the command operation is temporarily deformed or moved. That is, if, for example, part of the contour is pulled by using a mouse, it is temporarily deformed and displayed. If stopping the mouse operation, part of the contour which has been pulled, returns to an original position and displayed. As a result, the shape of the extracted contour and that of the target can be easily compared.

The present invention also provides a picture processing apparatus having a function of displaying the entire extracted contour or part of the extracted contour which is expanded outside by a predetermined amount or contracted inside in accordance with the above command operation.

If a command is issued by the command operation, the entire extracted contour or part of the extracted contour which is expanded outside by a predetermined amount or contracted inside by a predetermined amount is displayed. As a result, the shape of the extracted contour and that of the target can be easily compared.

The present invention also provides a picture processing apparatus having a function of displaying the entire extracted contour region or part of the contour region by moving it horizontally or vertically by a predetermined amount in accordance with the above command operation.

If a command is issued by the above command operation, the display picture is changed such that the entire extracted contour or designated part of the extracted contour, which is moved horizontally or vertically by a predetermined amount in accordance with the command operation, is displayed. Therefore, it is possible to manually change the position of the contour on the display picture while keeping the original shape and magnitude. As a result, the shape of the extracted contour and that of the target can be easily compared.

The present invention further provides a picture processing apparatus having functions of extracting the contour of the target on the picture, oscillating and thereby displaying the entire extracted contour or part of the extracted contour externally, internally or both externally and internally by a predetermined amount with reference to the contour position of the target on the picture.

The contour of the target on the picture is extracted. The display picture is changed such that the entire extracted contour or part of the extracted contour is repeatedly moved so as to oscillate it externally, internally or both externally and internally by a predetermined amount with reference to the contour position of the target on the picture. Therefore, the wobbling (wavering) contour is displayed while maintaining the original shape, thereby facilitating comparing the shape of the extracted contour with the shape of the target.

In addition, the present invention provides a picture processing apparatus comprising means for extracting the contour of the target on the picture and issuing a command for switching between a display and a non-display of the contour at predetermined time intervals and means for generating a display picture obtained by superimposing the contour over the target picture during a time period in which the contour is to be displayed and for generating a display picture including only the target picture during periods other than the above time period to thereby flash-displaying the contour picture.

The contour of the target on the picture is extracted. A display picture is generated by superimposing the extracted contour over the target on the picture, whereby the contour is displayed. If a command is issued, the contour display period and the contour non-display period are switched. During the contour non-display period, the contour is eliminated and only the target picture is present on the display picture. During the contour display period, the display picture is changed to the picture where the contour is superimposed over the above picture, whereby the contour is displayed. As a result, if a command is issued, the contour is flash-displayed, thus facilitating comparing the shape of the extracted contour with that of the target.

The present invention provides a picture processing apparatus comprising means for extracting the contour of the target on the picture and issuing a switching command, means for selectively generating a display picture obtained by superimposing the contour of the target over the target picture and a display picture including only the target picture, in accordance with the switching command.

The contour of the target on the picture is extracted. A display picture is generated by superimposing the extracted contour over the target on the picture, whereby the contour is displayed. When a switching command is issued, the display picture is changed to a display picture including only the target picture, and displayed. As a result, if a switching command is give by an operator's operation, it is possible to eliminate or display the contour by the operator's operation, thus facilitating comparing the shape of the extracted contour with that of the target.

The present invention also provides a picture processing apparatus comprising means for extracting the contour of the target on the picture and designating a desired region of the extracted contour, means for issuing a switching command, means for selectively generating a display picture obtaining by superimposing the contour of the target over the target picture, a display picture including only the target, a display picture obtaining by eliminating the contour designated by the designation means or the contour other than the designated contour from the superimposed picture of the target picture and the target contour, in accordance with the switching command.

The contour of the target on the picture is extracted. A display picture is generated by superimposing the extracted contour over the target on the picture, whereby the extracted contour is displayed. When a desired region of the extracted contour is designated and a switching command is issued, the display picture is changed to a display picture obtained by superimposing the contour over the above target picture while the designated contour or the contour other than the designated contour is eliminated in accordance with the switching command, and the changed picture is displayed. When a switching command is given, the display picture is changed to a display picture including only the target picture and displayed. As a result, if a switching command is given by the operator's operation, it is possible to eliminate or display the contour by the operator's operation, and to designate an eliminated region or a display region, thus facilitating comparing the shape of the extracted contour with that of the target.

The present invention provides a picture processing apparatus having functions of extracting the contour of the target on the picture, making the brightness of the picture with that of the original picture and generating a display picture so as to display the contour and the original picture with different colors.

The contour of the target on the picture is extracted. A display picture is generated by superimposing the extracted contour over the target on the picture, and the display picture is displayed. At this time, the brightness of the contour is made proportional to that of the original picture and is given a color different from that of the original picture. By so doing, the contour and the original picture are displayed with difference colors. That is, a translucent contour is displayed. As a result, while the original picture can be observed even in the contour portion, the contour portion can be also observed, thus facilitating comparing the shape of the extracted contour with that of the target.

As described above, the present invention is intended to extract the contour of the target on the picture, to divide the extracted contour into a display portion and a non-display portion and to display the target picture and the display portion of the contour by superimposing the display portion of the contour over the target picture. In addition, the present invention is intended to extract the contour of the target on the picture and to display the extracted contour region by superimposing it over the target on the picture and by scaling it. Furthermore, the present invention is intended to display the contour with a different color from that of the original picture and to switch the display picture between the picture obtained by superimposing the contour over the target and the picture including only the original picture. Therefore, the contour picture and the original picture can be easily compared, thereby making it easy to compare the shape of the contour and that of the original picture at high accuracy. Due to this, it becomes possible to apply the present invention to the evaluation of the accuracy of the contour extraction result or the analysis of the movement state of the moving target by using the contour lines.

The present invention provides a picture processing apparatus comprising means for extracting contours of the target from a series of moving pictures, means for obtaining contour internal areas for respective pictures from the contour information extracted from the respective pictures, means for detecting either a maximum contour internal area or a minimum contour internal area or both maximum and minimum contour internal areas within a predetermined time period and means for obtaining the contour internal area of the above picture from the detected value.

The picture processing apparatus for extracting contours of the heart from a series of heart moving pictures showing the cross section of the heart comprises means for obtaining contour internal areas for respective pictures from the contour information extracted from the respective pictures, means for obtaining either a maximum or minimum contour internal area or both maximum and minimum contour internal areas among the contours of the respective pictures within a predetermined time period and means for specifying pictures corresponding to either the heart terminal diastole period or the heart terminal systole period, or both the heart terminal diastole period and the heart terminal systole period based on the detected values.

That is, the present invention provides a picture processing apparatus for extracting contours of the target from moving pictures obtained by, for example, the ultrasonic diagnosis apparatus, calculating areas of the extracted contours and detecting the maximum and minimum areas as a terminal diastole area and a terminal systole area, respectively.

The present invention provides a picture processing apparatus for extracting contours of the target from moving pictures obtained by, for example, the ultrasonic diagnosis apparatus, respectively, calculating internal volumes of the extracted contours using the extracted contours, obtaining maximum and minimum volumes among the obtained contour internal volumes and detecting the maximum and minimum volumes as a terminal diastole volume and a terminal systole volume, respectively.

The present invention provides a picture processing method comprising the steps of extracting contours of the target from moving pictures obtained by, for example, the ultrasonic diagnosis apparatus, obtaining an area/volume showing a minimum moving amount on time-by-time basis from moving amounts obtained by using the extracted contours and detecting a maximum and a minimum area/volume as a terminal diastole area/volume and a terminal systole area/volume, respectively.

According to the present invention, it is possible to accurately determine the heart terminal diastole period and the heart terminal systole period from concrete areas or volumes of the heart and to obtain the pumping function of the heart quantitatively. Thus, objective measurement information useful to the diagnosis of the subject's cardiac function can be easily obtained while lessening the burden on the inspector.

The present invention provides a cardiac function analysis support apparatus and a cardiac function analysis support method for dividing cardiac wall contours into a plurality of regions based on the characteristic points of the cardiac wall contours detected manually or automatically from the cardiac wall contour information extracted manually or automatically from time series heart pictures obtained from the picture diagnosis apparatus, associating the divided contour regions in different time phases with one another and outputting cardiac movement information.

By so doing, even if the cardiac wall moves in parallel to the contour tangent direction, characteristic points can be detected. As a result, it is possible to accurately associate characteristic points for time series pictures and to accurately associate a plurality of pictures of the cardiac wall portions divided based on the characteristic points. That is, it is possible to divide a cardiac wall region and to analyze the cardiac function conformable to the actual cardiac wall movement.

According to the present invention, an annulus valva and a cardiac apex or a papillary muscle are set as characteristic points. By so doing, inappropriate association is prevented from occurring in the vicinity of valves or the cardiac apex, which has been a problem, particularly, to the center line method. Besides, the use of the papillary muscle enables association by short axis pictures to be conducted accurately.

According to the present invention, the divided cardiac wall contour regions are classified for positions at the cardiac wall, respectively. Among the classified cardiac wall contours, adjacent contours are displayed with different colors or different brightness. By so doing, it is possible to display cardiac wall regions referred to as a front wall cardiac apex portion and a lower wall base portion with different colors, thereby facilitating grasping the state of the wall movements in respective cardiac wall regions.

According to the present invention, a picture in a desired time phase serving as a reference time phase is automatically or manually set among time series heart pictures, the cardiac wall contours are divided, moving amounts of division points of the contours of the pictures in respective time phases from the corresponding division points of the contour of the picture in the reference time phase are calculated, respectively. The calculated moving amounts are displayed by at least one of numerical display, graph display or color display of the cardiac wall. By so doing, it is possible to easily discriminate a region having a large moving amount from a region having a small moving amount in the cardiac wall, thereby increasing the efficiency of the analysis of the cardiac function.

According to the present invention, velocity information obtained from the ultrasonic diagnosis apparatus is classified for the divided points of the cardiac wall contours. Velocity statistic is calculated for the classified cardiac wall positions, respectively and the calculated velocity statistic is displayed by at least one of numerical display, graph display and color display of cardiac wall. By so doing, it is possible to easily confirm velocity information of respective cardiac wall regions classified for the sake of a diagnosis, thereby increasing the efficiency of the analysis of the cardiac function.

The present invention is characterized in that a dynamic range of the moving amounts of the cardiac wall division points is detected, display colors for displaying velocity information obtained from the ultrasonic diagnosis apparatus on the picture are allotted within the dynamic range. By so doing, even if the overall wall movement is small, it is possible to clearly display differences in moving amounts between parts of the cardiac wall.

Additional object and advantages of the invention will be set forth in the description which follows, and in part will be obvious from the description, or may be learned by practice of the invention. The object and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 24 is a diagram for describing an example of an enlarged contour in the picture processing apparatus of FIG. 23;

FIG. 25 shows the operation input section of the picture processing apparatus of FIG. 23;

FIG. 26 is a diagram for describing an operation example in the picture processing apparatus of FIG. 23;

FIG. 47 is a block diagram of the picture processing apparatus in an embodiment according to the present invention;

FIG. 48 is a flowchart showing a processing flow in the picture processing apparatus in the embodiment of FIG. 47;

FIG. 49 is a block diagram of the picture processing apparatus in an embodiment according to the present invention;

FIG. 50 is a flowchart showing a processing flow in the picture processing apparatus in the embodiment of FIG. 49;

DETAILED DESCRIPTION OF THE INVENTION

Embodiments of the present invention will be described with reference to the drawings.

First, the structure of an ultrasonic picture processing apparatus will be described with reference to FIG. 1.

Figure 1:
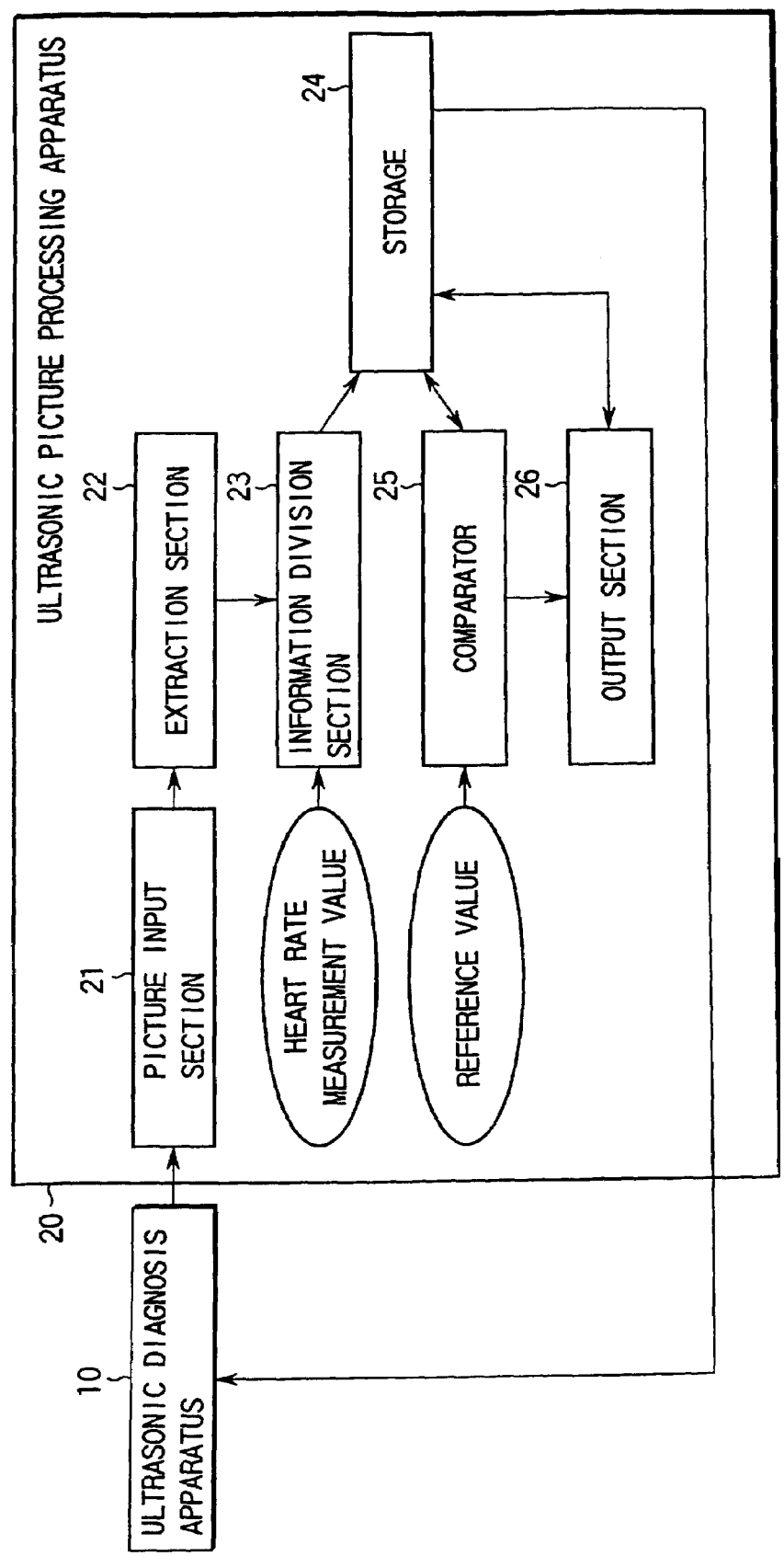
FIG. 1 is a block diagram showing an example of the structure of an ultrasonic picture processing apparatus using the ultrasonic picture processing method in the first embodiment according to the present invention.

In FIG. 1, an ultrasonic diagnosis apparatus 10 is connected to an ultrasonic picture processing apparatus 20. The ultrasonic picture processing apparatus 20 comprises a moving picture input section 21, a contour extraction section 22, a sampling section 23, a storage 24, a comparator 25 and an output section 26. Heart moving pictures outputted from the ultrasonic diagnosis apparatus 10 are sequentially inputted into the moving picture input section 21. The contour extraction section 22 extracts contours of moving pictures inputted into the moving picture input section 21 or extracts a region of the heart.

An information divider 23 divides time series information of contours of a cardiac wall or a region of the heart extracted at the contour extraction section 22 for each predetermined sampling time period, for example, a sampling time period set based on a heart rate measurement value inputted from an external apparatus. The divided information is temporarily stored in the storage 24.

The comparator 25 compares the divided information about the contours of the cardiac wall or the regions of the heart stored in the storage 24 with one another. The comparator 25 also compares a comparison value (or a reference value) previously stored therein and suited for a diagnosis with the divided information about the contours of the cardiac wall or the regions of the heart stored in the storage 24, to determine whether moving pictures are useful for the diagnosis. The moving pictures, if determined as useful pictures, are stored in, for example, the storage 24.

Figure 5:
FIG. 5 shows an example of comparison results of moving information about sampled contours.

The output section 26 includes, for example, a display for displaying comparison values indicated by a formula (1) in a time series manner; i.e., Diff (a, b), Diff (b, c), . . . or as shown in FIG. 5. The output section 26 also reads the moving pictures determined as useful for the diagnosis by the comparator 25, from the storage 24 and displays them. The moving pictures determined as useful pictures are fed to the ultrasonic diagnosis apparatus 10 to serve as processing targets during predetermined diagnosis processing.

FIG. 1 describes the ultrasonic picture processing apparatus 20 as an external apparatus connected to the ultrasonic diagnosis apparatus 10. The structure elements of the ultrasonic moving picture processing apparatus 20 shown in FIG. 1 may be incorporated into the ultrasonic diagnosis apparatus 10.

The ultrasonic moving picture processing method in the first embodiment according to the present invention will be described with reference to FIGS. 1 through 6, using a case of the diagnosis of the heart by way of example.

Figure 2:
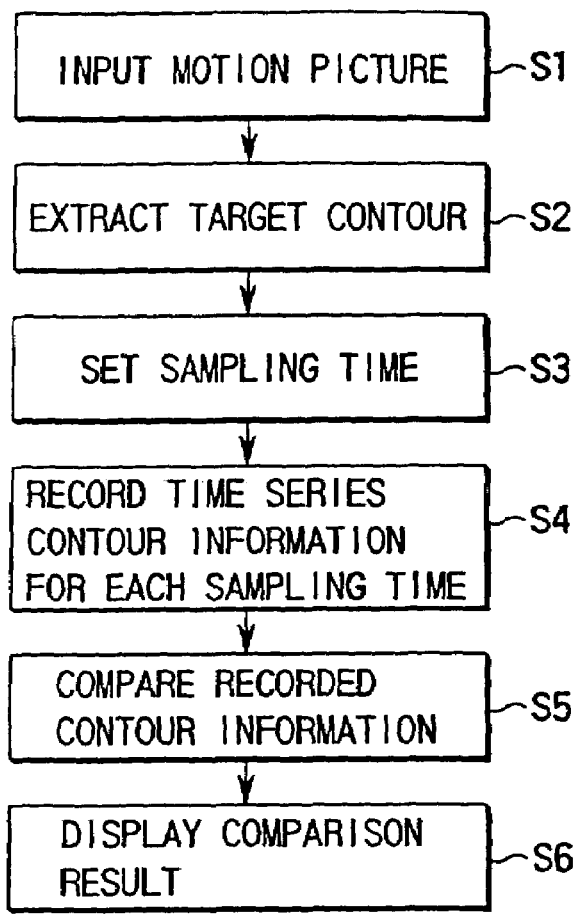
FIG. 2 is a flowchart for describing processing steps of the ultrasonic picture processing method in the first embodiment according to the present invention.

As shown in the flowchart of FIG. 2, heart moving pictures are inputted into the moving picture input section 21 of the ultrasonic moving picture processing apparatus 20 from the ultrasonic diagnosis apparatus 10 (S1). Contours of a target (cardiac wall) are extracted from the inputted moving pictures by the extraction unit 22 (S2). The extraction of the contours of the cardiac wall can be automatically and easily performed by using, for example, a method of active contour models and balloons (Laurent D, Cohen, CVGIP: IU, 53(2): 211=218, 1991). Next, sampling time periods for dividing time series contour information are set (S3). In this embodiment, the values which have been inputted in advance are set as sampling time. Thereafter, respective pieces of time series contour information extracted at the thus set sampling time are stored in the storage 24 (S4). Pieces of the stored contour information are compared with one another by the comparator 25 (S5).

Figure 3:
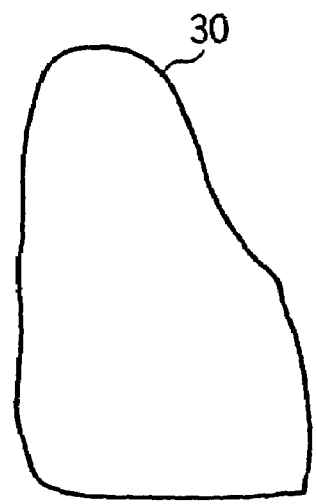
FIG. 3 shows an example of an extracted cardiac wall contour.
Figure 4:
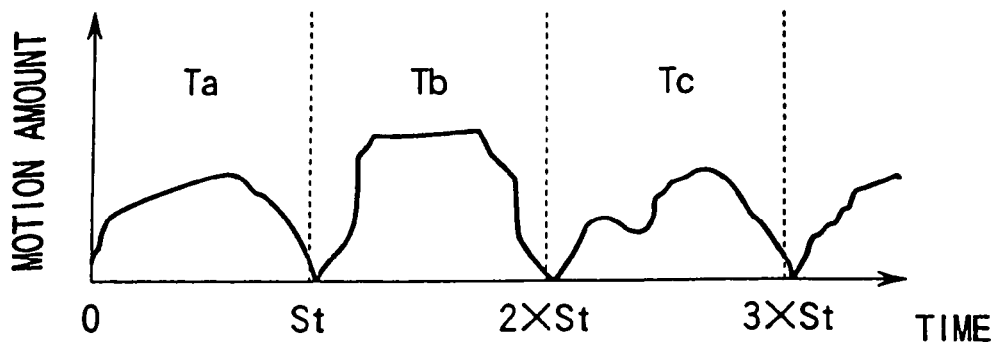
FIG. 4 is a diagram for describing a method for moving information about the extracted time series contours.

The comparison in this embodiment is conducted as follows. As shown in FIG. 3, movement amounts of the entire cardiac wall contour 30 extracted in the step S2 are averaged and divided for every sampling time St and the movements are recorded (see FIG. 4). In this embodiment, since absolute values of the movement amounts are recorded with reference to a contour at a given time period, positive values are obtained as shown in FIG. 4. Due to the periodic cardiac movement, a periodic graph is obtained as shown in FIG. 4.

The sampled data series are set as Ta, Tb, Tc . . . and adjacent data series such as Ta and Tb, Tb and Tc, are compared. The comparison is made using an error of mean square as shown in the following formula (1):

$$Diff(a,b) = \sum_{i=0}^{n-1} \frac{\sqrt{(Ta(i) - Tb(i))^2}}{n} \quad (1)$$

The formula (1) shows an example of the comparison of the data series Ta and Tb. In the formula (1), Ta(i) denotes the i-th data (i-th movement amount) of the data series Ta, Tb(i) denotes the i-th data of the data series Tb and n denotes the number of data series. The number n is determined by the processed number during the extraction of the cardiac wall contours. For example, if the frame rate of moving pictures obtained from the ultrasonic diagnosis apparatus is 30 (frame/second) and contours of all of the frames of the moving pictures are extracted, then n is calculated by the following formula (2), while the contour data sampling time set as Ts (second) as described above:

$$n = Ts \times 30 \quad (2)$$

Finally, comparison values obtained from the formula (1) are displayed in a time series manner such as Diff (a, b), Diff (b, c), . . . as shown in FIG. 5 (S6).

Figure 6:
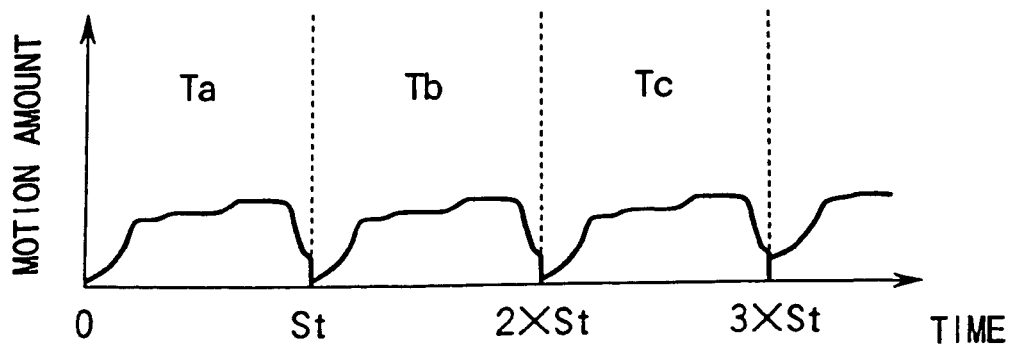
FIG. 6 shows an example of moving information about cardiac wall contours without an influence of the movement of hands and the movement of a body.

Due to the periodic heart movement, if there are no movements, such as the movement of the body or the movement of hands, other than the heart, a periodic and uniform curve is provided by plotting the movement amounts of the cardiac wall as shown in FIG. 6. In such a case, the comparison value Diff in the formula (1) is quite low (almost "0").

On the other hand, if the movement of the body or the movement of hands are added to the movement of the cardiac wall, the movement amounts of the cardiac wall are expressed as an irregular curve as shown in FIG. 4 and the comparison value Diff becomes higher. As such a manner, since it is possible to determine whether or not the collected moving pictures include the movement of the body or the movement of the hands by comparing moving amounts of the contours in respective sampling periods, it is possible to easily collect moving pictures useful for the diagnosis.

In this embodiment, comparison values of the contour moving amounts are displayed for determining whether or not the moving pictures are useful for the diagnosis. It is also possible to determine the usefulness of the moving pictures by displaying graphs obtained by plotting contour movements on time-by-time bases as shown in FIGS. 4 and 6. In the latter case, determination cannot be made based on a quantitative index. However, since visual determination is possible to a certain extend, pictures free from the movement of the body or the movement of the hands can be easily collected. The comparison result of contour movement amounts are displayed by plotting comparison values on time-by-time basis. The comparison values may be displayed directly.

Next, the second embodiment according to the present invention will be described with reference to FIG. 7.

Figure 7:
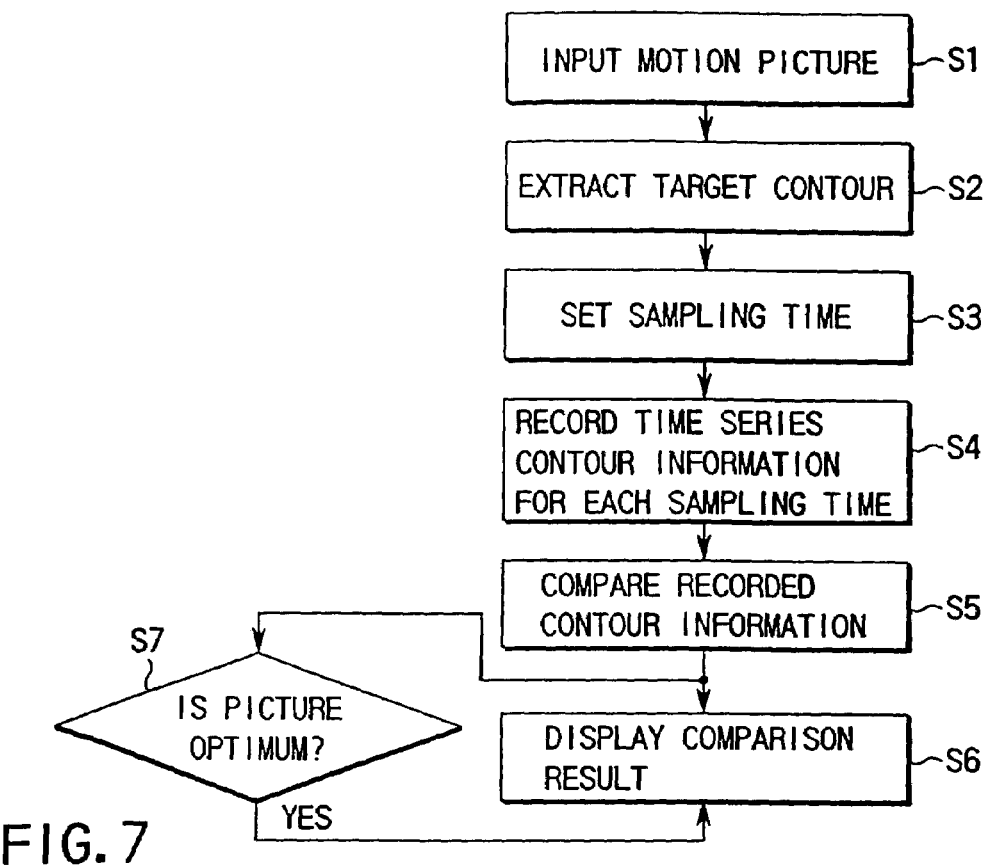
FIG. 7 is a flowchart for describing processing steps of the ultrasonic picture processing method in an embodiment according to the present invention.

FIG. 7 is a flowchart showing other processing steps of the ultrasonic picture processing method in this embodiment. The same steps as those in FIG. 2 are denoted by the same reference numerals. Description will be given only to steps different from the case of FIG. 2. That is, in this embodiment, a comparison value suited for a diagnosis is set as a reference value in advance as shown in FIG. 7. By comparing the contour information with the reference value, it is determined whether or not moving pictures are useful for the diagnosis (S7). The comparison results are displayed, as well (S6).

The ultrasonic moving pictures determined as useful for the diagnosis are fed back to, for example, the ultrasonic diagnosis apparatus and become diagnosis targets.

The third embodiment according to the present invention will be described with reference to FIG. 8.

Figure 8:
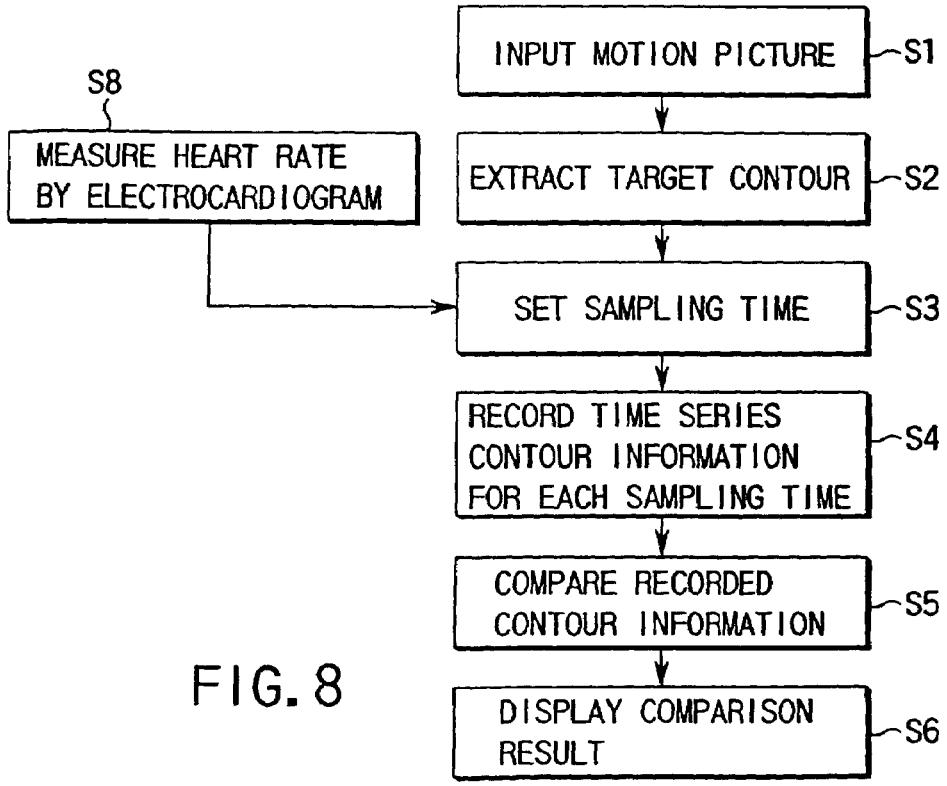
FIG. 8 is a flowchart for describing processing steps of the ultrasonic picture processing method in an embodiment according to the present invention.

FIG. 8 is a flowchart showing other processing steps of the ultrasonic picture processing method in this embodiment. In these steps, sampling time is determined based on heartbeat information obtained by an electrocardiograph as shown in the block diagram of FIG. 1.

Specifically, as shown in FIG. 8, the processing is the same as that of FIG. 2 from steps S1 through S6. However, in step S3, when sampling time is set, heartbeat is measured by the electrocardiograph (S8) and sampling time is set based on the heartbeat information obtained from the electrocardiograph.

Due to the periodic cardiac movement, it is desirable that the sampling time for time series contour information is the same as the period of the heartbeat. The heartbeat period of a human is about 1 second; however, it depends on individual subjects. Therefore, if setting sampling time based on the information from the electrocardiograph as mentioned above, it is possible to determine whether or not the collected moving pictures are suited for the diagnosis at high precision.

Next, another embodiment will be described with reference to FIGS. 9 through 11. This embodiment illustrates a case of calculating comparison values not using an average contour movement amount but the contour movement amounts of respective parts. Description will be given only to elements different from those of the preceding embodiments.

Figure 9:
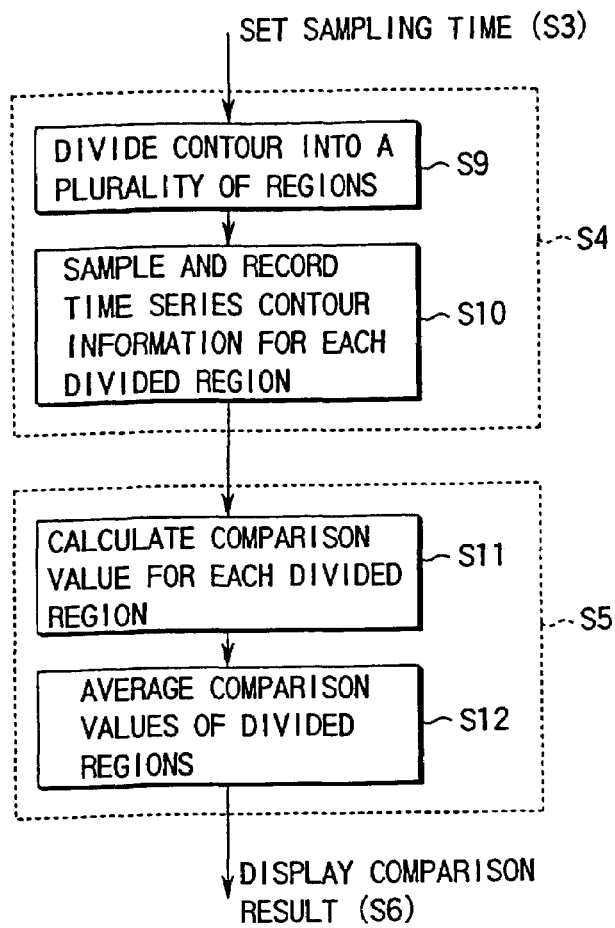
FIG. 9 is a flowchart for describing recording processing of time series information for every sampling time and comparison processing of the recorded contour information in the ultrasonic picture processing method in an embodiment according to the present invention.
Figure 10:
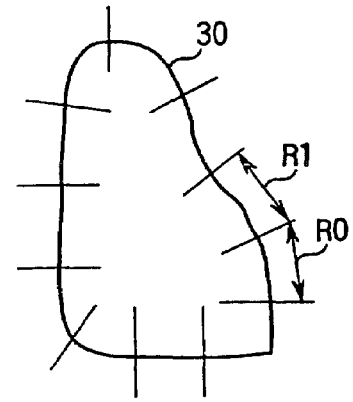
FIG. 10 is a diagram for describing a method for dividing contours.
Figure 11:
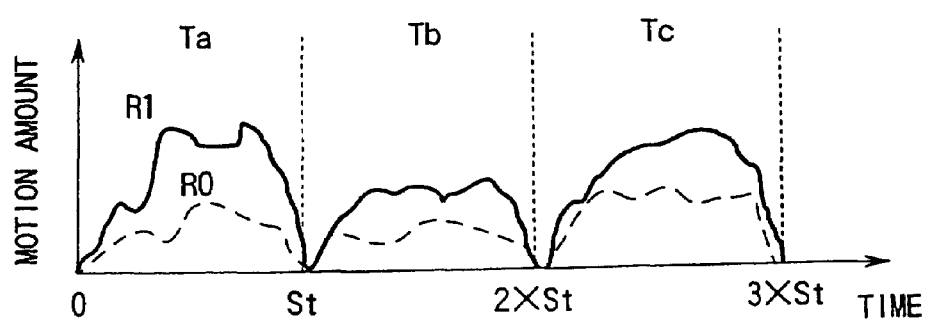
FIG. 11 is a diagram for describing a method for sampling divided time series contour information.

As shown in FIG. 9, in step S4, when time series contour information is recorded, the extracted cardiac wall contour 30 are divided into a plurality of regions (R1, R2, . . . , RN−1), respectively as shown in FIG. 10 (S9). Time series information about respective divided regions (such as regions R0, R1) is recorded for every sampling time (St) as shown in FIG. 11 (S10).

Next, during the comparison of contour information in the step S5, data series comparison is made for respective divided regions (R0, R1, . . . , RN−1) by using the above-described method and comparison values in the respective regions are calculated by the following formula (3) (S11).

$$\text{Diff\_R0}(a, b) = \sum_{i=0}^{n-1} \frac{\sqrt{(Ta(i) - Tb(i))^2}}{n} \quad (3)$$

$$\text{Diff\_R1}(a, b) = \sum_{i=0}^{n-1} \frac{\sqrt{(Ta(i) - Tb(i))^2}}{n}$$

$$\vdots$$

In the formula (3), DiffΔR0 (a, b) denotes a comparison value of the data series Ta and Tb in the region R0 and Diff ΔR1 (a, b) denotes a comparison value of the data series Ta and Tb in the region R1. Thereafter, in this embodiment, the calculated comparison values are averaged using a formula (4) (S12) and the results are displayed as comparison values of the overall contours as shown in FIG. 5 (S6).

$$\frac{\sum_{i=0}^{N-1} \text{Diff\_R1}(a, b)}{N} \quad (4)$$

In the formula (4), N denotes the number of divided contours. Other processing steps are the same as those in the first embodiment.

Yet another embodiment according to the present invention will be described with reference to FIGS. 12 and 13. This embodiment illustrates a case of using region information as time series data used in the comparison processing in the embodiment of FIG. 2.

Figure 12:
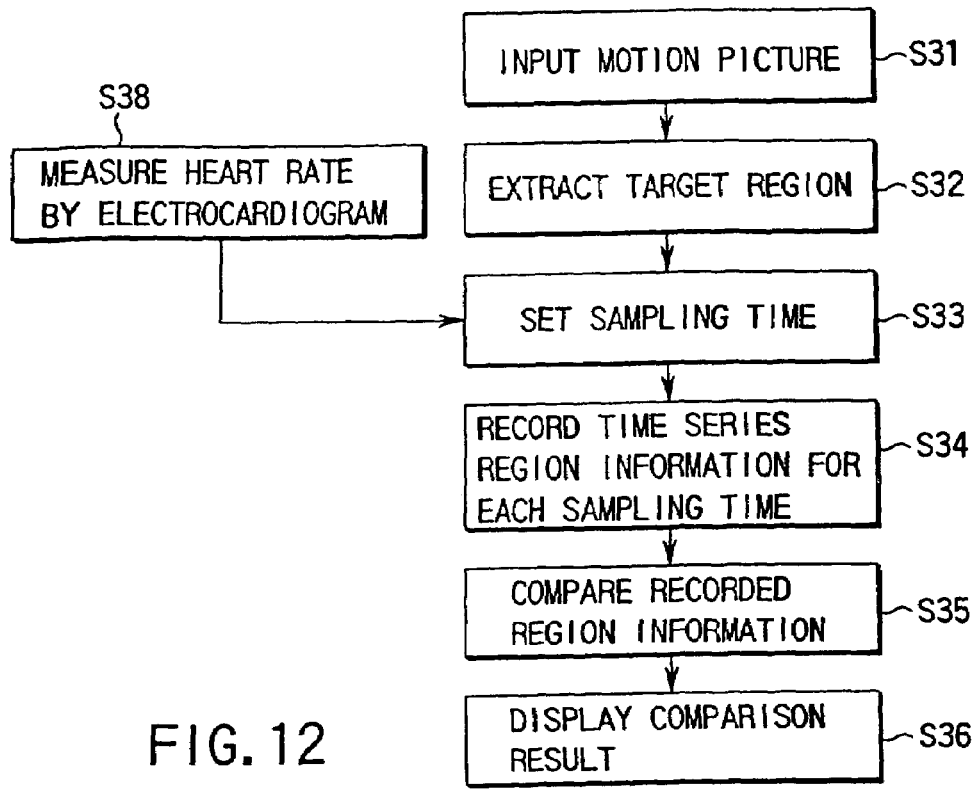
FIG. 12 is a flowchart for describing processing steps of the ultrasonic picture processing method in an embodiment according to the present invention.
Figure 13:
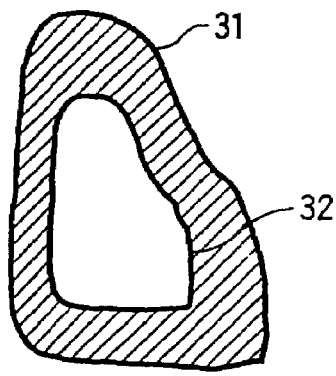
FIG. 13 shows an example of a cardiac muscle region used for the extraction of moving information.

FIG. 12 is a flowchart showing the processing steps of the ultrasonic picture processing method of this embodiment.

Heart moving pictures are inputted from the ultrasonic diagnosis apparatus (S31). A region of the heart is extracted from the inputted moving pictures (S32). In this embodiment, the region refers to a heart muscle (a region between an outer cardiac wall 31 and an inner cardiac wall 32).

Thereafter, as in the case of FIG. 8, the heart rate is measured by the electrocardiograph (S38) and sampling time is set based on the information obtained from the measurement of the heart rate (S33). Time series region information is recorded for every sampling time (S34). Respective pieces of the recorded time series region information are compared (S35). Finally, comparison results are displayed (S36).

Figure 14:
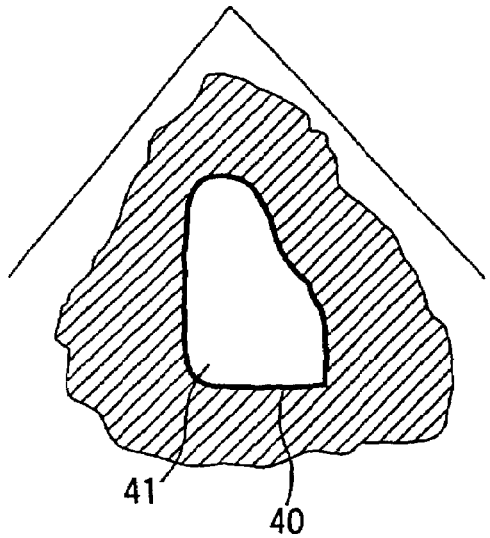
FIG. 14 shows an example of a region used for the extraction of moving information.

In this embodiment, the region information used in the comparison is related to the region of the entire heart muscle. However, it is also possible to divide the heart muscle into a plurality of regions as described in the embodiment of FIG. 9 and to compare time series region information. Furthermore, this embodiment uses the heart muscle as a target region. However, using the fact that the echo strength of blood and those of other portions differ (usually, the echo strength of blood is lower than those of other portions) in the ultrasonic diagnosis apparatus, it is possible to divide a target region into a blood region 41 surrounded by the cardiac wall 40 and the remaining region (indicated by oblique lines) as shown in FIG. 14 and to obtain movement information about one of or both of the divided regions.

Figure 15:
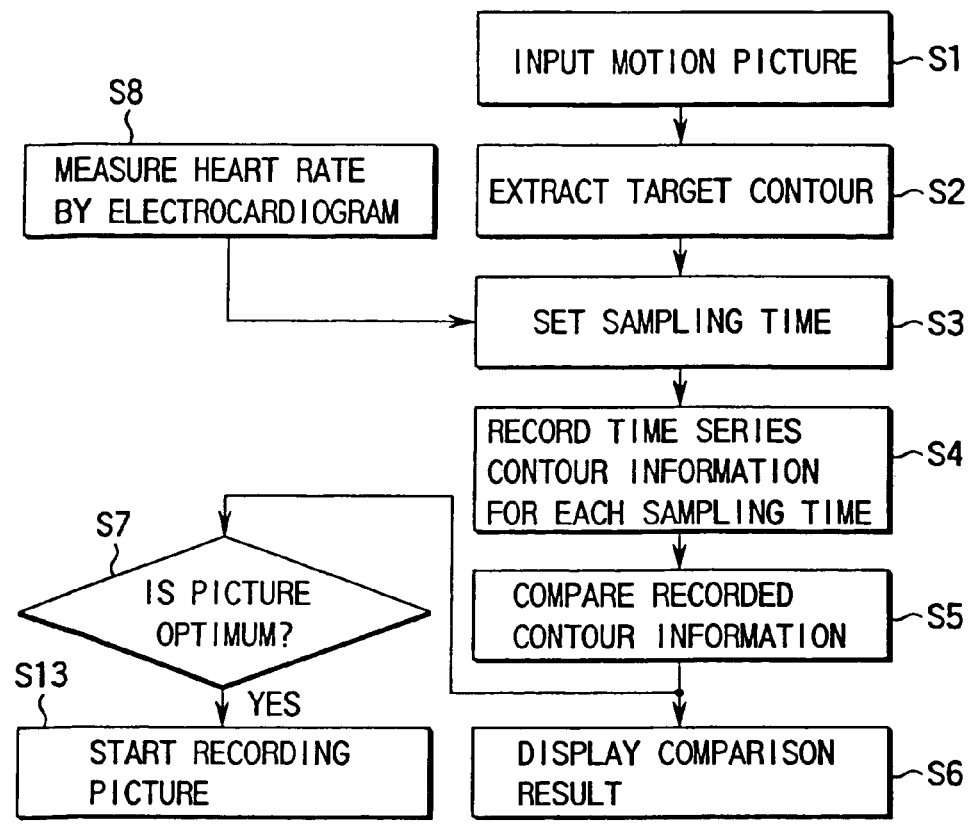
FIG. 15 is a flowchart for describing processing steps of the ultrasonic picture processing method in an embodiment according to the present invention.

Another embodiment will be described with reference to FIG. 15. This embodiment illustrates a case of conducting processing (recording of moving pictures) in accordance with the result of the recorded time series information. In the flowchart of FIG. 15, the same processing steps as those of FIGS. 2, 7 and 8 are denoted by the same reference numerals.

In FIG. 15, after comparing the recorded contour information in a step S5, the results are displayed in a step S6. As described in the embodiment of FIG. 2, it is determined whether or not a picture satisfies a preset criteria (whether it is a picture free from the hand movement or the body movement and suited for the diagnosis) (S7). If satisfying the criteria, the original moving picture is recorded in a predetermined storage medium (S13).

The moving pictures satisfying the criteria are fed back to, for example, the ultrasonic diagnosis apparatus and become diagnosis targets.

By so doing, unnecessary pictures unsuited for the diagnosis are not recorded and wastefulness of the storage medium can be thus eliminated.

The embodiments described with reference to FIGS. 1 through 15 employ the movement amounts of the contours or region of a target as information to be used when determining whether pictures are useful for the diagnosis. It is possible to employ movement amounts obtained by automatically detecting or manually setting characteristic points 50 on the target 40, i.e., adjacent to the contour thereof and tracking these movements.

Figures 16, 17:
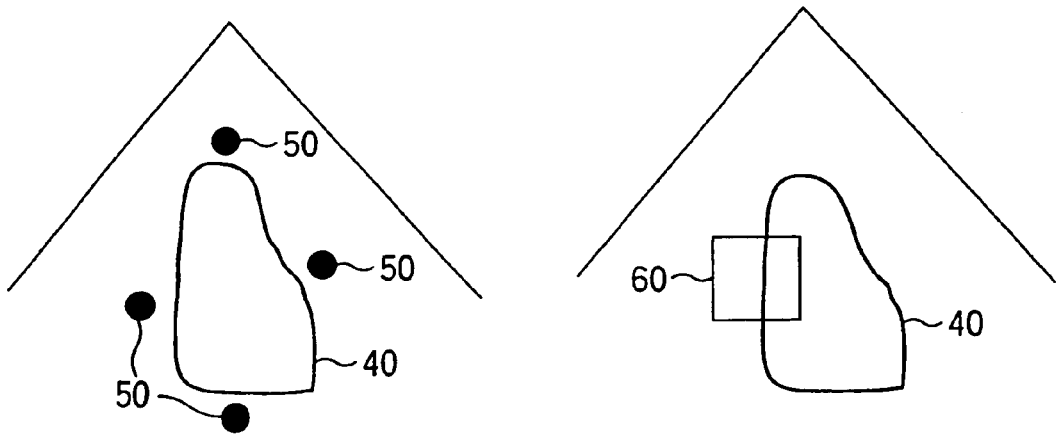
FIG. 16 shows an example of characteristic points on a picture used for the extraction of moving information in an embodiment according to the present invention.
FIG. 17 shows an example of a concerned region on a picture used for the extraction of moving information in the ultrasonic picture processing method in an embodiment according to the present invention.

Alternatively, as shown in FIG. 17, it is possible to set an optional concerned region 60 on the target (or cardiac wall) 40, to track the region 60 by calculating an optical flow in the inner region or by using the correlation method and to thereby obtain and compare time series movement amounts.

Although the above-described embodiments employ a heart as a target, the present invention can be applied to organs other than the heart. In such cases, other organs do not move periodically like the heart and movements of the contours or region are not represented by a periodic curve. Due to this, it is not necessary to set sampling time periods based on the electrocardiograph information. Rather, preset optional time periods can be used.

The methods described above can be stored as programs which can be executed by a computer, in a storage medium such as a magnetic disc (floppy disc, hard disc and the like), an optical disc (CD-ROM, DVD and the like) and a semiconductor memory.

In the above-described embodiments, contour information or region information is extracted from ultrasonic moving pictures and the time series contour information or region information is divided based on the preset sampling time periods. However, it is also possible to divide the ultrasonic moving picture based on preset sampling time periods in advance and then to extract contour information or region information from the frame pictures during the respective time period.

As described above, according to the embodiments of the present invention, moving pictures which are free from the movement of the subject's body or the movement of the inspector's hands and important to the diagnosis of a disease can be easily determined and collected from the ultrasonic pictures obtained by the ultrasonic diagnosis apparatus.

Now, the description will be given to a picture processing apparatus and method capable of displaying pictures such that it can be easily determined whether the extracted contours are correct or not and that movement states of respective portions can be tracked and analyzed from the extracted contour information.

Figure 18:
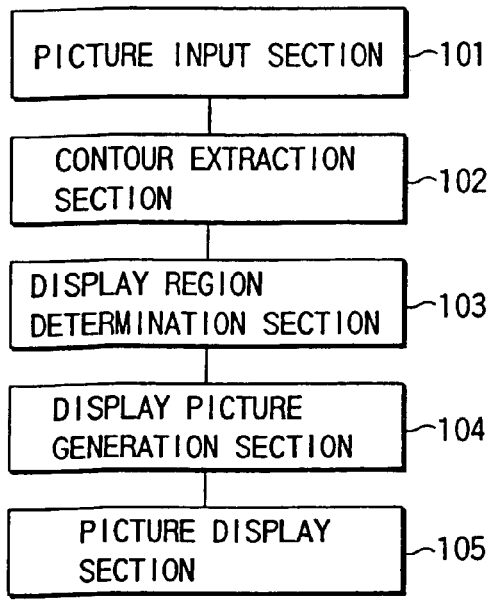
FIG. 18 is a schematic block diagram of the picture processing apparatus in an embodiment according to the present invention.

As shown in FIG. 18, the picture processing apparatus comprises a picture input section 101, a contour extraction section 102, a display region determination section 103 and a display picture generation section 104.

The picture input section 101 receives ultrasonic pictures from, for example, the ultrasonic diagnosis apparatus, as original picture and input the pictures into the contour extraction section 102. The contour extraction section 102 has a function of extracting contours of a target from the original pictures inputted by the picture input section 101. The display region determination section 103 has a function of determining a region to be displayed from the contour region (the entire region of the extracted contour lines) extracted by the contour extraction section 102. The display picture generation section 104 has a function of generating a display picture by superimposing a display region within the contour region determined by the display region determination section 103 over the original pictures previously inputted by the picture input section 101. The picture display section 105 displays the picture obtained by the display picture generation section 104.

With the above structure, when the picture input section 101 inputs an original picture such as an ultrasonic picture into the contour extraction section 102, the contour extraction section 102 extracts the contour of a target from the original picture received from the picture input section 101 by a method using active contour models and feeds the contour to the display region determination section 103. The display region determination section 103 determines a display region from the extracted contour region (the entire region of the extracted contour lines) and feeds the determined information, that is, the display region to the display picture generation section 104. The display picture generation section 104 generates a display picture by superimposing the display region within the contour region determined by the display region determination section 103 (a display target region within the entire region of the contour lines) over the original picture previously inputted by the picture input section 101. The picture display section 105 displays the display picture obtained by the display picture generation section 104, that is, a superposition picture of the contour picture over the original picture. The display picture is therefore a picture obtained by superimposing the respective contour lines over the original picture, whereby both the original picture and the contour lines can be observed. This makes it possible to easily verify whether the contour lines are aligned to the target portion and to observe a picture.

Figure 19:
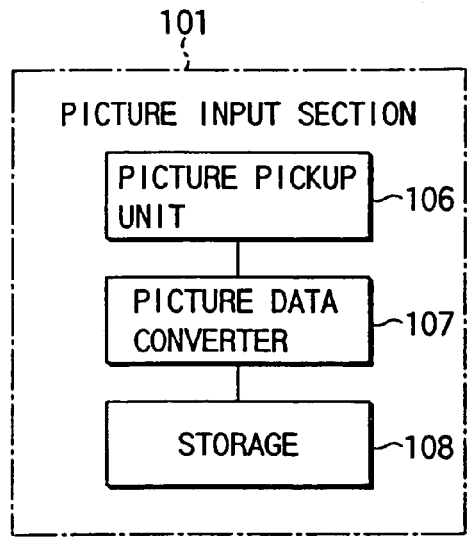
FIG. 19 is a block diagram of the picture input section of the picture processing apparatus of FIG. 18.

The picture input section 101 has a structure as shown in FIG. 19. Namely, the picture input section 101 comprises an picture pickup unit 106, an picture data converter 107 and a picture storage section 108.

Among these elements, the picture pickup unit 106 obtains a real-time moving picture (as well as a still picture). The unit 106 corresponds to, for example, a medical diagnosis apparatus such as an ultrasonic diagnosis apparatus. The picture data converter 107 converts a picture signal obtained by the picture pickup unit 106 into a data format in units of frames (units of picture planes) so that the contour extraction section 102 can handle it. The picture storage section 108 stores picture signal data converted by the picture data converter 107.

The picture input section 101 having this structure coverts a picture signal from the picture pickup unit 106, such as an ultrasonic diagnosis apparatus, into a data format which can be handled by the contour extraction section 102 at the picture data converter 107 and stores the converted data in the picture storage section 108. The picture input section 101 then reads the data stored in the picture storage section 108 and supplies the data to the contour extraction section 102 and to the display picture generation section 104.

Figure 20:
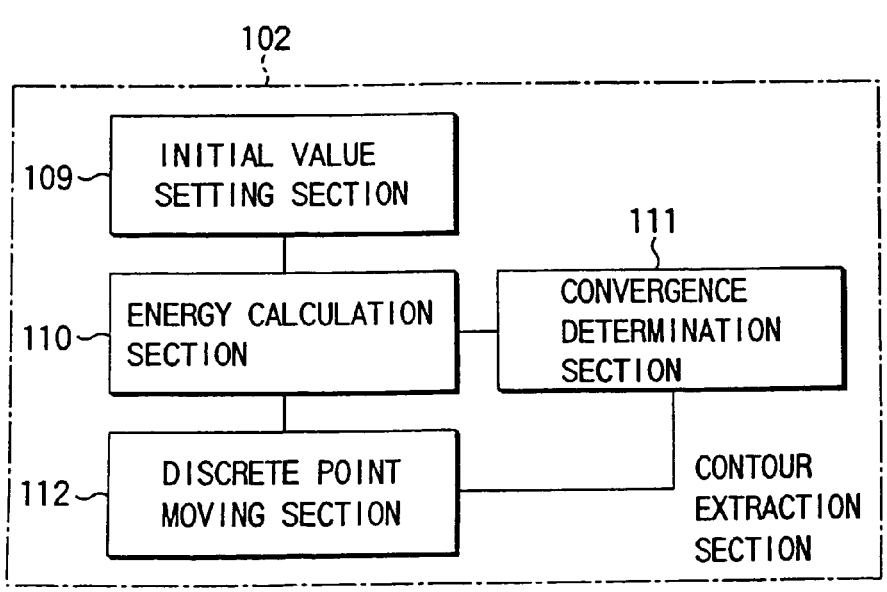
FIG. 20 is a block diagram of the contour extraction section of the picture processing apparatus of FIG. 18.

The contour extraction section 102 has a structure as shown in FIG. 20. A case of extracting contours using active contour models will be described hereinafter. The contour extraction section 102 comprises an initial value setting section 109, an energy calculator 110, a convergence determination section 111 and a discrete point moving section 112.

Among these elements, the initial value setting section 109 has a function of setting an initial contour. In this case, the initial value setting section 109 sets a contour by manually providing the coordinate of the initial contour. If the coordinate of the initial contour is provided manually, a GUI (graphical user interface) and a pointing device such as a mouse, a pen, a track ball, are used. By operating the direction cursor of the pointing device, a coordinate is designated on the display picture plane. An initial contour is thereby plotted and inputted on the picture plane. An original picture is displayed on the display plane. Using the pointing device, the coordinates of positions of the contour lines are designated and plotted on the original picture. The inputted coordinate positions are displayed on the picture plane and stored as coordinate position information. The contour thus inputted is expressed as a collection of representative coordinates on the contour and stored in this form in the built-in memory of the initial setting section 109.

The energy calculator 110 calculates the sum of the internal energy of the contour, picture energy and external energy given at need. The discrete point moving section 112 has a function of moving the contour (conducting a convergence calculation) so that the energy sum calculated by the energy calculator 110 is as small as possible.

The convergence determination section 111 functions to receive information about the sum of energies calculated by the energy calculator 110, to determine whether or not a change in the sum of energy is smaller than a predetermined value, to determine that the sum of energy is convergent when the change is smaller than the predetermined value, to issue a command to stop the convergence calculation to the energy calculator 110 and to thereby end the convergence calculation at the energy calculator 110.

The display region determination section 103 functions to set a region for connecting representative points on the contour obtained by the contour extraction section 102 by straight lines or curves and to determine a display portion within the region.

The display picture generation section 104 functions to replace only the pixel value in the portion of the original picture inputted by the picture input section 101 corresponding to the display region within the contour region determined by the display region determination section 103, with a different pixel value and to thereby generate α display picture having the display region within the contour region superimposed over the original picture. The picture display section 105 functions to display the picture generated by the display picture generation section 104 on a display device.

The contour extraction section 102 having the above structure operates as follows. An initial contour is set by the initial value setting section 109. Coordinates of the initial contour are given manually. The contour is expressed as a collection of representative coordinates on the contour and stored in this form in the built-in memory. When the initial contour is set by the initial value setting section 109, the energy calculator 110 calculates a sum of the internal energy of the initial contour, picture energy and external energy given at need. The discrete point moving section 112 moves the contour so that the energy sum calculated by the energy calculator 110 is as small as possible.

The convergence determination section 111 monitors a change in the energy sum calculated by the energy calculator 110, determines whether this change is smaller than a predetermined value and issues a command to stop a convergence calculation to the discrete point moving section 112 when the change is smaller than the predetermined value. When the change is larger than the predetermined value, the convergence determination section 111 operates so that the discrete point moving section 112 repeats moving the contour. When the change is smaller than the predetermined value as a result, the discrete point moving section 112 ends moving the discrete point.

Figure 21A:
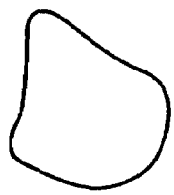
FIGS. 21A and 21B show a contour region and a display region in the picture processing apparatus of FIG. 18, respectively.
Figure 21B:
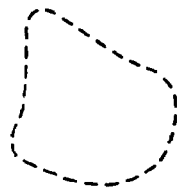

The display region determination section 103 sets a display region as a region obtained by connecting representative points of the contour obtained by the contour extraction section 2 by straight lines or curves. The display region determination section 103 determines a portion to be displayed in that region. The portion is, for example, a portion in which the contour is repeatedly displayed and not displayed at certain intervals (refer to FIGS. 21A and 21B).

The display picture generation section 104 generates a display picture by replacing only the pixel value of a portion of the original picture inputted by the picture input section 101, corresponding to the display region within the contour determined by the display region determination section 103, with a different pixel value.

Figure 22:
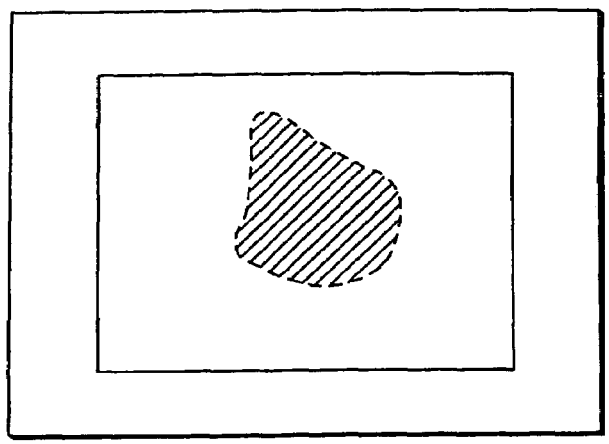
FIG. 22 shows an example of picture display in the picture processing apparatus of FIG. 18.

The display section 105 displays the picture generated by the display picture generation section 104 on a display device such as a display (refer to FIG. 22).

Both the information about the contour extraction result and the information about the vicinity of the contour of the original picture can be indicated at a time by failing to display part of the contour region as mentioned above.

In other words, in this embodiment, when an original picture, which is, for example, an ultrasonic picture of the heart, is inputted, a contour is roughly inputted on the ultrasonic picture of the heart and the inputted contour line is automatically corrected by the energy calculation and the like based on the inputted contour. Then the contour lines or the picture of the contour region in the designated display target portion is superimposed over the original picture and displayed. Furthermore, the picture on the displayed contour line or in the contour region is periodically replaced with the original picture, thereby making it possible to clearly compare the contour with the target portion of the original picture.

The apparatus in this embodiment can easily extract a target portion of the original picture and allows a user to easily determine whether or not the extracted contour is correct based on the direct comparison of the extracted contour with the original picture.

Therefore, by evaluating the accuracy of the extracted contour and utilizing the information about the accurately extracted contour for an analysis, it is possible to apply the contour line of the moving target picture to the analysis of the moving state of the target.

Another embodiment for extracting and displaying contour lines will be described.

In this embodiment, an example of displaying the contour expanded outside by a predetermined amount or reduced inside by means of inputting commands by a user interactively.

Figure 23:
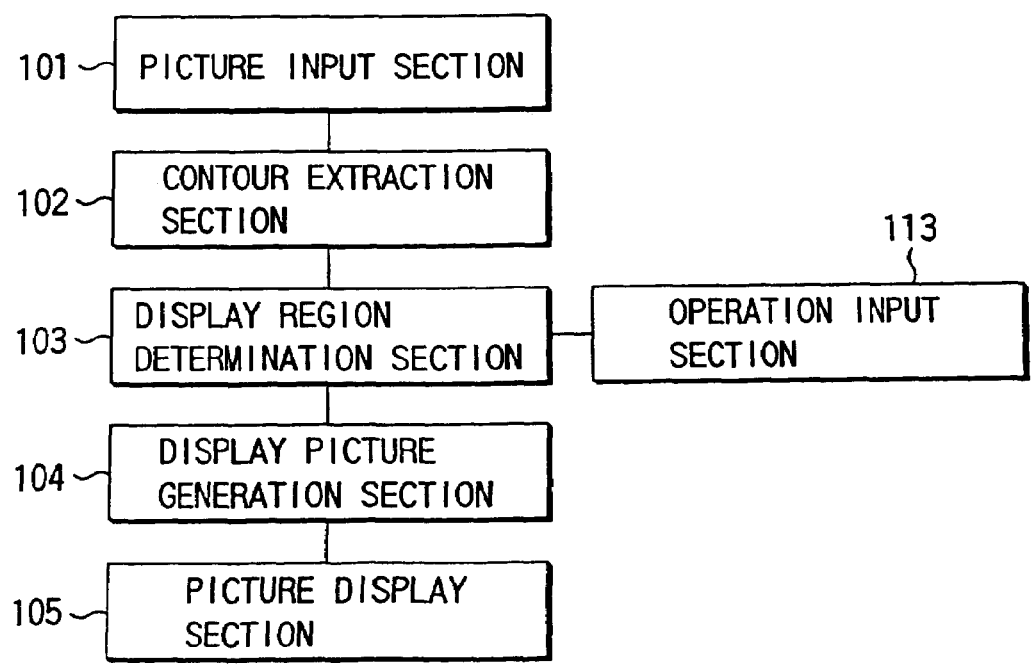
FIG. 23 is a block diagram of the picture processing apparatus in an embodiment according to the present invention.

The structure of this embodiment is illustrated by FIG. 23. The picture processing apparatus of FIG. 23 comprises a picture input section 101, a contour extraction section 102, a display region determination section 103, a display picture generation section 104, a picture display section 105 and an operation input section 113.

The picture input section 101, the contour extraction section 102, the display picture generation section 104 and the picture display section 105 in this embodiment are the same as those in the embodiment of FIG. 18. The apparatus in this embodiment is characterized by comprising the operation input section 113. The operation input section 113 designates the picture display magnification of a target portion on the display plane, displays the target portion in the form shown in FIG. 25 on the picture plane and designates a scaling rate by selecting the rate using a mouse cursor.

As shown in FIG. 25, the operation input section 113 has three operations buttons; i.e., an "enlargement" button 113a, a "reduction" button 113b, and a "return" button 113c. When pushing the "enlargement" button 113a, the picture scaling rate α is increased. When pushing the "reduction" button 113b, The picture scaling rate α is reduced. When pushing the "return" button 113c, the picture scaling rate α is returned to the original rate and a command to display a picture at 100% magnification can be issued. This command is outputted by using the value of the scaling rate a.

This embodiment shows an example of using buttons at the operation input section 113. A slide bar, a dial, a mouse and the like may be used as input means, as well.

The display region determination section 103 converts coordinate of the contour data X into X' based on the scaling rate α given from the operation input section 113 (refer to FIG. 24):

$$X=\{(x1, y1), (x2, y2), \ldots, (xn, yn)\} \quad (5)$$

$$X=\{(x1', y1'), (x2', y2'), \ldots, (xn', yn')\} \quad (6)$$

Here, xi'=x0+α(xi−x0); yi'=y0+α(yi−y0); n is the number of representative points; and (x0, y0) is the center of gravity of the contour.

$$x_0 = \frac{1}{n}\sum_{i=1}^{n} x_i \quad (7)$$

$$y_0 = \frac{1}{n}\sum_{i=1}^{n} y_i \quad (8)$$

The example of the operation will be described hereinafter.

FIG. 26 illustrates a picture plane displayed on the picture display section 105. The picture display shows a state right after the contour extraction section 102 conducts processing shown in FIG. 18, the display picture generation section 104 generates a display picture obtained by superimposing an extracted contour region (all of the extracted contour lines) over an original picture. and the picture display section 105 displays the display picture 114. On this plane, reference numeral 114 denotes a picture of the target region obtained by superimposing the contour region over the original picture and reference numeral 15 denotes buttons 113a to 113c.

Figure 27:
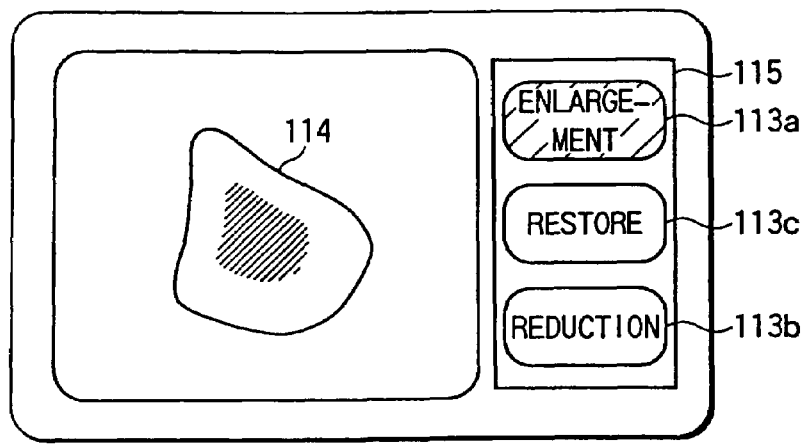
FIG. 27 is a diagram for describing an operation example in the picture processing apparatus of FIG. 23.
Figure 28:
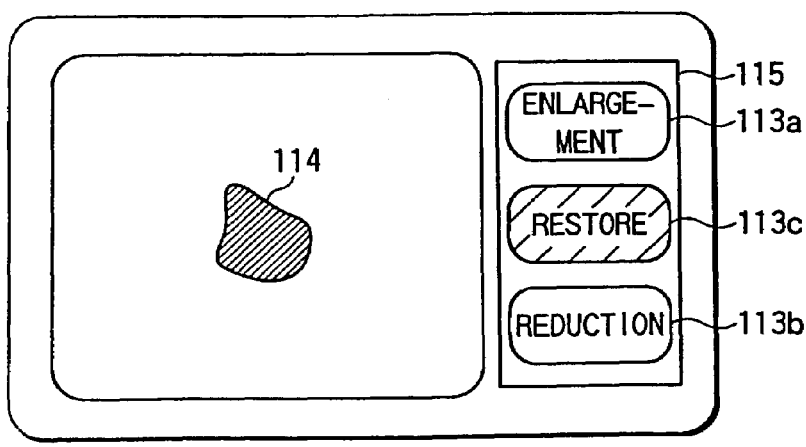
FIG. 28 is a diagram for describing an operation example in the picture processing apparatus of FIG. 23.
Figure 29:
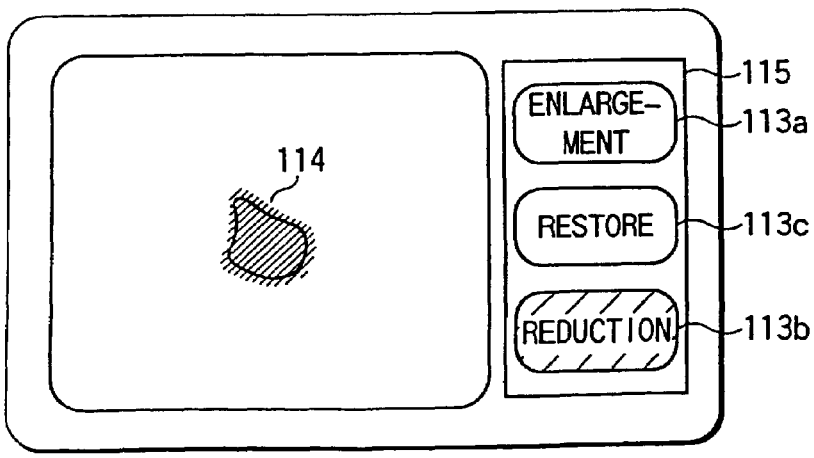
FIG. 29 is a diagram for describing an operation example in the picture processing apparatus of FIG. 23.

FIG. 27 illustrates a display plane on the picture display section 105 when operating the buttons and, in particular, right after pushing the "enlargement" button 113a. Only the contour region (or extracted contour lines) is enlarged and the picture of the target region is not enlarged. By expanding only the contour region (or extracted contour lines) outside, the original picture in the vicinity of the contour region can be observed. Thereafter, by pushing the "return" button 113c, the picture returns to its original unscaled (in FIG. 28). If the contour region can be more easily observed by reducing the picture inside, the "reduction" button 113b is pushed to thereby reduce the picture inside (in FIG. 29).

This embodiment displays the picture in the contour region (or extracted contour lines) by scaling the picture on the original picture. Due to this, it is possible to easily compare the picture in the contour region with the original picture, thereby facilitating the comparison and determination of the shape at high accuracy.

Figure 30:
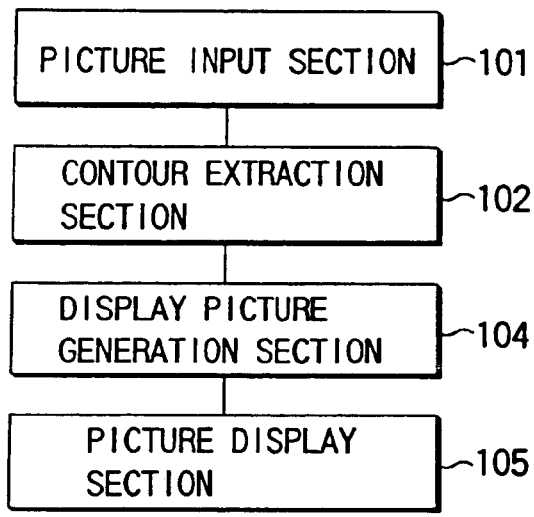
FIG. 30 is a block diagram of the picture processing apparatus in an embodiment according to the present invention.

The embodiment shown in FIG. 30 illustrates a case of displaying the contour by wobbling it inside and outside by a predetermined amount with reference to the extracted contour portion. The structure of this embodiment is the same as the embodiment of FIG. 23 except that the operation input section 113 can designate an amplitude A and a time period T of the wobbling. It is of course possible to automatically designate them. The system in this embodiment has a function of, if given an amplitude A and a time period T of wobbling, moving the picture in the contour region (or extracted contour lines) at the amplitude A and at the time period T and generating a picture to be displayed over the original picture.

The system in this embodiment is also provided with the operation input section 113. If the operation input section 113 designates an amplitude A and a time period T of wobbling, information about the amplitude A and time period T is supplied to the display region determination section 103.

The display region determination section 103, if given the amplitude A and time period T from the operation input section 113, converts the coordinate of (xi, yi) of representative point on each contour into a coordinate (xi', yi') expressed by the following formula (9) and formula (10):

$$xi'=x0+A(xi-x0)\sin(2\pi t/T) \quad (9)$$

$$yi'=y0+A(yi-y0)\sin(2\pi t/T) \quad (10)$$

Here, π is the ratio of the circumference of a circle to its diameter, t is time and (xi, yi) is the center of gravity of the contour as described in the embodiment of FIG. 23.

According to the system in this embodiment having the above structure, a contour region (or all contour lines) is obtained by the same procedures as in FIG. 18, a display picture obtained by superimposing the contour region over the target region of the original picture is generated by the display picture generation section 104 and the obtained picture is displayed on the display unit such as a display by the picture display section 105.

Meanwhile, according to this system, if the operation input section 113 designates the amplitude A and time period T of wobbling, the information is given to the display region determination section 103. The display region determination section 103 converts a coordinate (xi, yi) of the representative point of the contour into a coordinate (xi', yi') expressed by the formulas (9) and (10). As a result, each representative point (xi, yi) of the contour changes at the amplitude A and time period T of the wobbling. The display region determination section 103 composes a contour region reflecting this change on the original picture. The contour region of the picture displayed by the display unit changes at the amplitude A and the time period T.

Consequently, the comparison and contrast of the picture in the contour region and the original picture can be easily made, thus facilitating comparing and determining the shape at high accuracy.

The method of realizing the present invention by means of software using a calculator will be roughly mentioned. In the software processing, coordinates of representative points on the contours are calculated in accordance with formulas (11) and (12) every time the time period t passes by a predetermined interval Δt. From the calculated coordinates, a contour region is generated by the approximation of a line or curve. After the original picture data is re-drawn on the display, the obtained contour region is re-drawn. By making such a program and executing the program using the calculator, the present invention can be realized.

In this embodiment, it is possible to automatically generate α contour region unlike the embodiment FIG. 23. Since the displayed contour region is moved periodically, both the vicinity of the contour within the picture and the extracted contour region can be observed while dispensing with user's trouble. It is more effective if a transparent contour region is provided by an after-image effect by reducing the time period T of wobbling.

Figure 31:
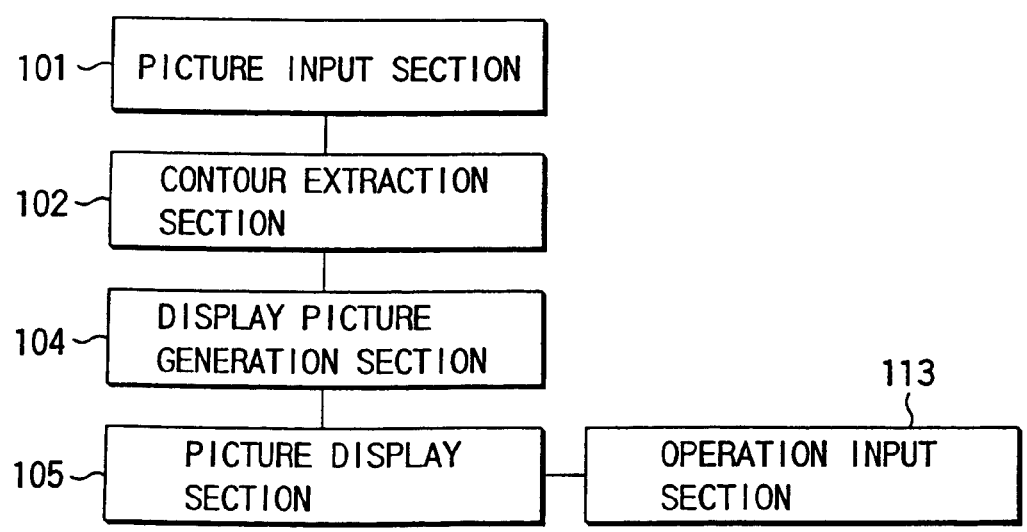
FIG. 31 is a block diagram of the picture processing apparatus in an embodiment according to the present invention.
Figure 32:
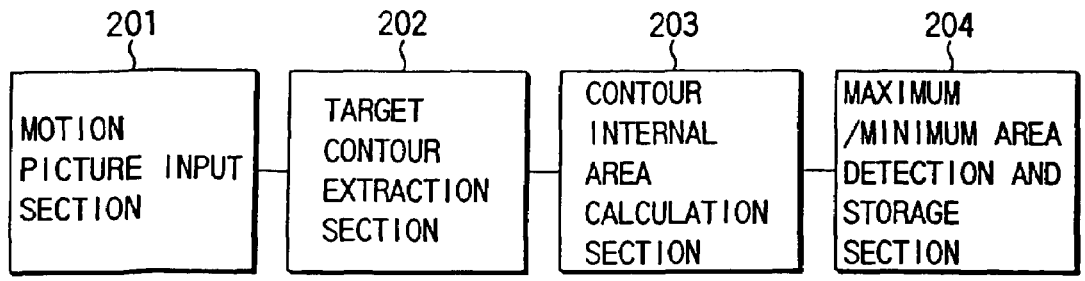
FIG. 32 is a block diagram of the picture processing apparatus in an embodiment according to the present invention.

In the embodiment of FIG. 31, a picture processing apparatus comprises a picture input section 101, a contour extraction section 102, a display picture generation section 104 and a picture display section 105.

The picture input section 101 and the contour extraction section 102 are the same as those shown in the embodiment of FIG. 18. According to the system of this embodiment, the display picture generation section 104 replaces a pixel value of a portion of the original picture corresponding to the contour region extracted by the contour extraction section 102, with a predetermined pixel value.

According to the system having such a structure, a contour region (or contour lines) is obtained in accordance with the same procedures as those in the embodiment of FIG. 18. The display picture generation section 104 replaces a portion of the original picture corresponding to the contour region extracted by the contour extraction section 102, with a predetermined pixel value and thereby generates a display picture.

Meanwhile, the picture display section 105 controls the original picture and the picture generated by the display picture generation section 104 such that they are alternately displayed at predetermined time intervals. By so doing, the picture generated by the display picture generation section 104 and the original picture are alternately displayed on the display unit by the picture display section 105.

In this way, according to this system, the display picture generation section 104 generates a picture obtained by replacing a portion of the original picture corresponding to the contour region, with a predetermined pixel value, and the original picture as well as the picture generated by the display picture generation section 104 are alternately displayed on the display unit.

Due to this, there exists a time period in which a contour region is not drawn. As a result, the original picture information can be grasped more precisely and both the vicinity of the contour within the picture and the extracted contour region can be observed while dispensing with the user's trouble. Thus, operability is improved. Besides, if the predetermined time interval $t$ is reduced, then a transparent contour region can be provided by an after-image effect and effective observation can be advantageously realized.

The display switching in this embodiment can be realized by software processing using a calculator. The method will be now described.

The display switching by means of software processing is conducted as follows. If a predetermined time interval is $\Delta t$ and time $t$ is $2n\Delta t$ (where $n$ is an integer), original picture data is re-drawn on the display. On the other hand, if time t is $(2n+1)\Delta t$, original picture data is re-drawn on the display and then the contour region previously obtained is re-drawn. By so doing, the picture generated by the display picture generation section 104 and the original picture can be alternately displayed.

The method shown in FIG. 31, different from the embodiment FIG. 23, can grasp original picture information more precisely since there exists a time period in which a contour region is not drawn. Besides, without troubling the user, the vicinity of the contour within the picture and the extracted contour region can be observed. Furthermore, if the predetermined time interval $t$ is reduced, a transparent contour region can be advantageously provided by an after-image effect.

In the embodiment of FIG. 31, the picture processing apparatus comprises a picture input section 101, the contour extraction section 102, the display picture generation section 104 and the picture display section 105.

The picture input section 101, the contour extraction section 102 and the display picture generation section 104 are the same as those in the embodiment of FIG. 30.

According to the system of the present invention, the picture display section 105 controls the original picture and the picture generated by the display picture generation section 104 such that they are alternately displayed. However, the picture generated by the display picture generation section 104 is displayed only when a command is manually given at the operation input section 113. For that reason, a button (display button) is provided at the operation input section 113 for the designation operation.

According to the system, while the display button on the operation input section 113 is being pushed, only the original picture obtained from the picture input section 101 is displayed. When the display button is released, only the generated picture of the picture display section 105 is displayed. Conversely, it is possible to display the generated picture of the picture display section 105 while the button is being pushed and the original picture is displayed when the button is released. It is also possible to change the display picture from "the generated picture of the picture display section 105" to "the original picture" to "the generated picture of the picture display section 105" to "the original picture" in this order every time the button is pushed. Further, operation means other than the button such as a slide bar, a dial, a mouse and the like may be used.

In this embodiment, different from the embodiment of FIG. 30, the timing for switching between the display and non-display of the contour region is freely determined. Since the switching can be thus freely made, it is possible to display a picture more conformable to the user's demand.

The sixth embodiment according to the present invention will be described.

The sixth embodiment is the modification of the embodiment of FIG. 30. The picture input section 101, the contour extraction section 102 and the picture display section 105 are the same as in FIG. 18. The display picture generation section 104 generates a picture by converting the pixel value of a portion of the original picture corresponding to the contour region extracted by the contour extraction section 102 in accordance with the following conversion processing. Specifically, if the brightness of the original picture is (I, I, I) in RGB color representation and the new brightness is (I, I, 0) in RGB color representation, the conversion is conducted as follows:

R=I
G=I
B=0

That is, the original picture is a color picture, and an R (red) component, a G (green) component and a B (blue) component of the original picture has the same brightness value which is I and colorless (either white or gray depending on the value of I). By the conversion processing, the R component and the G component are converted into "I" and the B component is converted into "0". As a result of the conversion processing, the monochrome pixel having the R component, G component and B component which are all I is converted into that having only the R component and the G component which are yellow. Therefore, after the above processing, the color of the contour region is changed to yellow. The brightness of the contour region is proportional to that of the original picture (that is, the brightness of the contour region having "I" is proportional to that of the original picture). Therefore, it is possible to obtain the original picture information even in the contour region. In addition, since information about the contour extraction result can be also obtained due to a change in color, it is possible to easily evaluate the contour extraction result.

In this embodiment, yellow is used as a color for representing the contour region. However, other colors may be used. As long as the brightness within the contour region can be kept, other conversion methods may be used. In this embodiment, the B component is fixed to 0 (B=0). However, it may be changed between "0" and "1" as time passes. In that case, the change can be obtained by wobbling both periodically and manually. If so, the change can give a visual impression more strongly, thereby facilitating the recognition of the contour region.

As described so far, the present invention extracts the contour of a target within a picture, divides the extracted contour into a display portion and a non-display portion and displays the target picture and the display portion within the contour by superimposing the display portion over the target picture. In addition, the present invention extracts the contour of the target within the picture, displays the extracted contour region by superimposing the contour region over the target picture within the picture and displays the contour while scaling it. Furthermore, the present invention changes the color of the contour when displaying it and can switch the display picture between the picture, over which the contour is superimposed, and the original picture. Therefore, the contour picture and the original picture can be easily compared, thereby facilitating the comparison and determination of the shape at accuracy.

As a result, it is possible to apply the present invention to the evaluation of the accuracy of the contour extraction result and the analysis of the state of the movement of a moving target using the contour lines of the picture.

The method described in the embodiment with reference to the drawings can be realized as software. The program by using the software can be stored in a storage medium, which can be read by a computer, such as a magnetic disc (a floppy disc, a hard disc), an optical disc (a CD-ROM, a DVD) and a semiconductor memory and can be distributed widely.

According to the embodiments of the present invention described above, it is possible to provide a picture processing apparatus and a picture processing method having an excellent advantage in that the determination of whether or not the extracted contour is correct can be easily made, which the conventional apparatus and method cannot make, and in that it is possible to apply the present apparatus and method to the analysis of the state of the movement of a moving target by using the contour of the picture of the target since the correct contour can be obtained.

Now, description will be given to various embodiments of a picture processing apparatus and a picture processing method capable of automatically obtaining, for example, a terminal diastole area or volume and a terminal systole area or volume of an ultrasonic picture.

Figure 33:
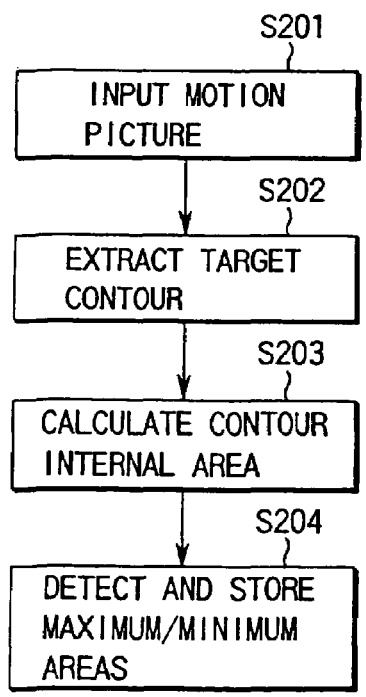
FIG. 33 is a flowchart for showing an example of a picture processing flow in the picture processing apparatus of FIG. 32.
Figure 34:
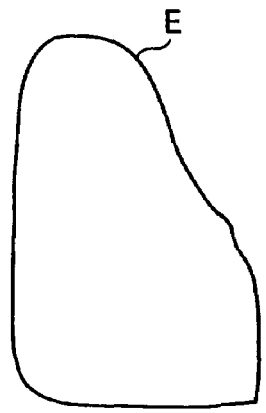
FIG. 34 shows an example of an extracted heart contour in the picture processing apparatus of FIG. 32.

FIG. 33 shows the structure of the ultrasonic picture processing apparatus. FIG. 34 shows the processing flow of a method for detecting picture collecting conditions of an ultrasonic picture.

A moving picture input section 201 inputs the moving picture of the heart of a subject by means of ultrasonic waves, X rays, magnetic resonance or the like. A target contour extraction section 202 extracts the contour of the heart from the heart moving picture for every picture (every frame). A contour internal area calculation section 203 calculates the area inside the extracted contour of the heart. A maximum/minimum area calculation/storage section 204 detects the maximum/minim areas among the calculated internal areas of the contour of the heart and stores the detected values while associating them with the pictures corresponding to the values, respectively.

According to the apparatus in this embodiment having this structure, moving pictures of the heart of the subject are inputted by the moving picture input section 201. This is done by obtaining moving pictures of the heart of the subject obtained by, for example, the ultrasonic diagnosis apparatus and using the obtained pictures as inputs.

More specifically, the moving picture input section 201 inputs moving pictures of the heart obtained in a time-series manner from, for example, the ultrasonic diagnosis apparatus (S201). The target contour extraction section 202 extracts the contour of the target (cardiac wall) from each of the inputted moving pictures (S202). The extraction of the contour of the cardiac wall can be conducted automatically and easily by means of, for example, the method using active contour models and balloons: "On Active Contour Models and Balloons (Laurent D. Cohen, CVGIP: IU, 53(2): 211-218, 1991). FIG. 34 shows the typical example of an extracted contour by that method. By conducting processing in step S202, contour information can be obtained for every picture as shown in FIG. 34.

Thereafter, processing is conducted by the contour internal area calculating section 203. The contour internal area calculation section 203 calculates the internal area of each of the contours based on the respective contour information extracted by the target contour extraction section 202 (S203). The maximum/minimum area calculation/storage section 204 detects and stores maximum/minimum values of the internal area of the contour of each picture obtained by the contour internal area calculation section 203 (S204).

Contours are extracted from the time-series ultrasonic pictures showing the sectional views of the heart and internal areas of the contours are calculated using the extracted contour information, thereby obtaining the maximum and minimum areas.

The detailed method for obtaining the maximum and minimum internal areas of the contours will be now described.

Figure 35:
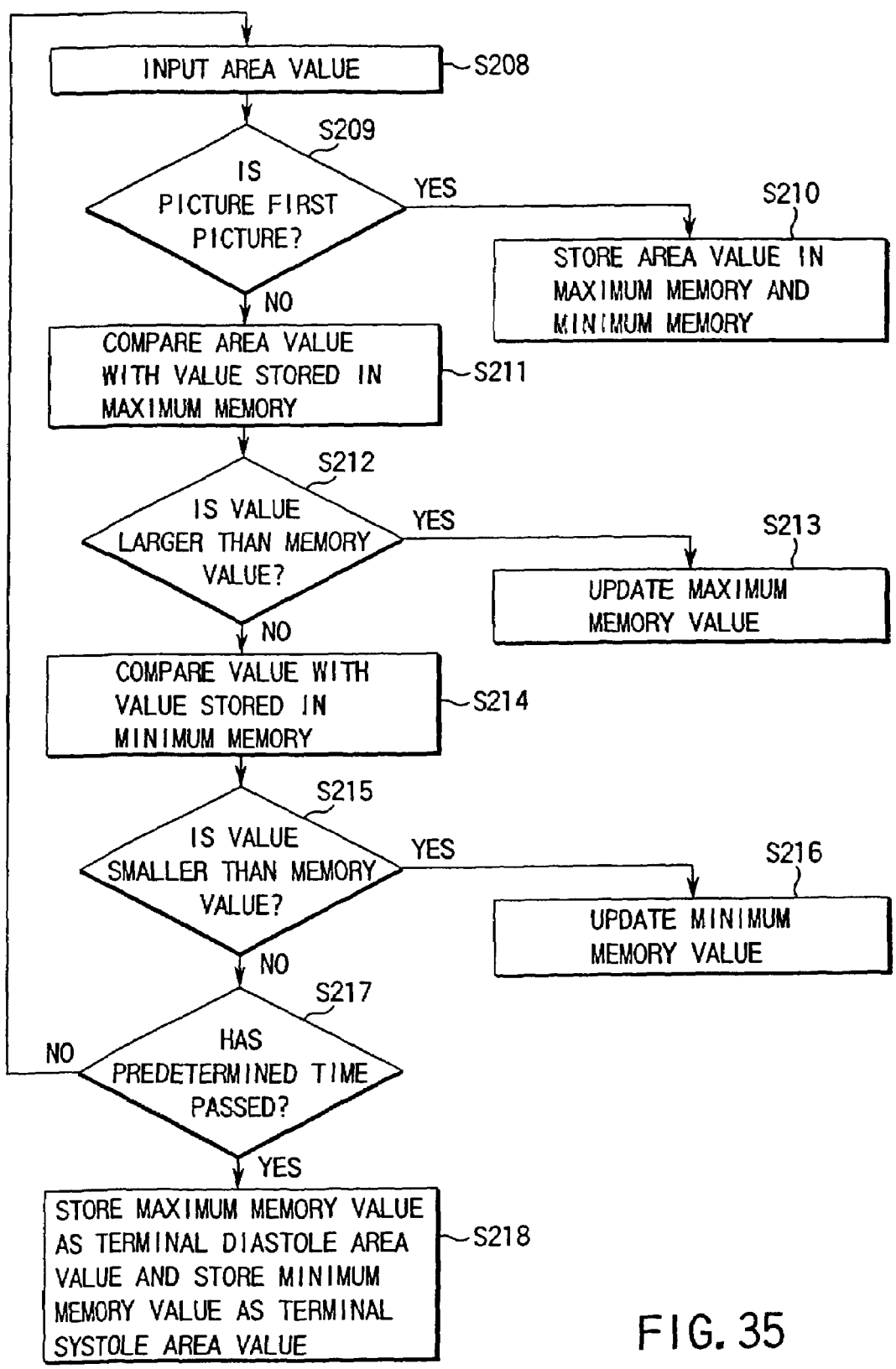
FIG. 35 is a flowchart for showing a detailed processing flow of the processing step S204 of FIG. 33.

FIG. 35 shows the example of the processing flow of the step S204 conducted by the maximum/minimum value detection/storage section 204 shown in FIG. 33 in more detail. In the step S204, the calculated value of the internal area of the contour obtained in step S203 is inputted (S208). It is determined whether it is a value is for the first picture (S209). If it is determined as first picture value, the inputted area is temporarily stored in maximum/minimum memories (S210).

Next, the stored value is compared with a value (a retained maximum value) stored in the maximum memory (S211). If the value temporarily stored in the maximum/minimum memories S210 is larger than the retained maximum value (S212), the maximum value is updated to the temporarily stored value in the maximum memory (S213).

Meanwhile, as a result of the determination in step S212, if the value temporarily stored in the maximum/minimum memories is not larger than the retained maximum value, the maximum value is not updated and the temporarily stored value is compared with a value (a retained minimum value) stored in the minimum memory (S214). If the value temporarily stored in the maximum/minimum memories in step S210 is smaller than the retained minimum value (S215), the minimum value in the minimum memory is updated to the temporarily stored value (S216). As a result of the determination in step S215, if the temporarily stored value is not smaller than the retained minimum value, the minimum value is not updated and the processing enters step S217.

In the step S217, it is determined whether or not the processing of input pictures for a predetermined time period is finished. If the processing for the predetermined time period is finished, a maximum memory value and a minimum memory value are stored as a terminal diastole area and a terminal systole area, while associating them with each other, respectively (S218).

The data can be stored in the memory by arranging in a form of (terminal diastole area value, the time phase thereof), (terminal systole area value, the time phase thereof) and the like. It is also possible to simultaneously store the electrocardiogram information about the corresponding time phases. These arranged values may be outputted to an output unit such as a printer instead of storing them in the memory or while doing so.

In this embodiment, contours of the heart are extracted based on the moving pictures of the real-time ultrasonic sectional image of the heart for every picture plane. The internal area of each of the contours is obtained and it is determined whether the area is the maximum or minimum value. The maximum and minimum value are updated and retained for a predetermined time period. Due to this, it is possible to detect the maximum and minimum sectional areas of the heart shown on the inputted pictures for a predetermined time period. If the predetermined time period is in line with the moving period of the heart, the terminal systole and the terminal diastole of the heart can be grasped automatically.

For the purpose of discovering the terminal heart systole period and the terminal heart diastole period, the following area measurement method is taken.

Figure 36:
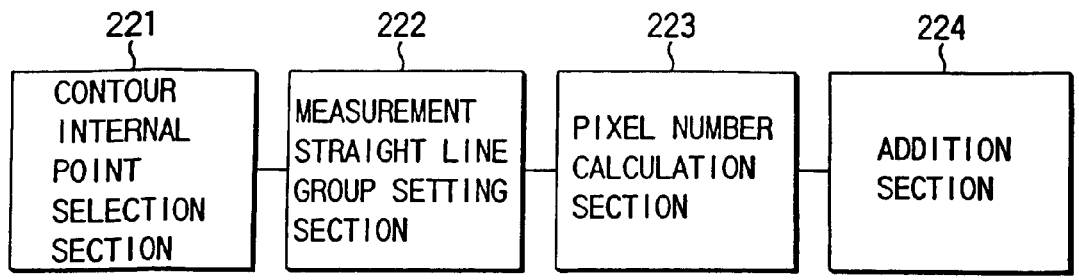
FIG. 36 is a block diagram of the picture processing apparatus in an embodiment according to the present invention.
Figure 37:
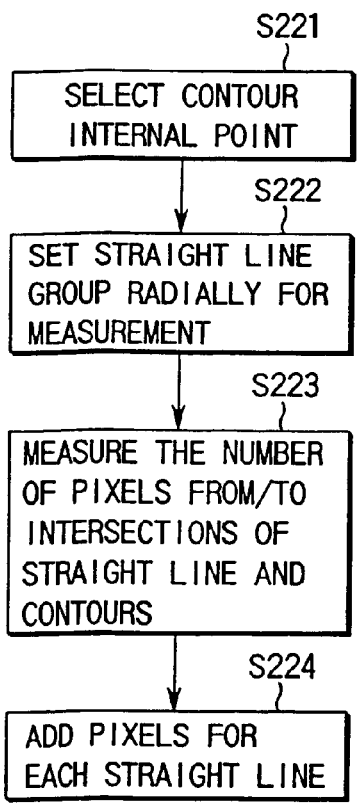
FIG. 37 is a flowchart showing an example of a picture processing flow in the picture processing apparatus of FIG. 36.

FIG. 36 shows an embodiment of a picture processing apparatus. FIG. 37 shows the processing flow of the picture processing apparatus.

In FIG. 36, the picture processing apparatus comprises a contour internal point selection section 221, a measurement straight line group setting section 222, a pixel number measurement section 223 and an addition section 224.

The contour internal point selection section 221 selects a required point inside the detected contour E. The measurement straight line group setting section 222 sets a measured group of straight lines provided radially around the required point. The pixel number measurement section 223 measures the number of passed pixels $\underline{p}$ for every straight line by the straight line set by the measurement straight line group setting section 222 crosses the contour. The addition section 224 obtains the cross-sectional area of the heart by adding the number of pixels $\underline{p}$ measured by the pixel number measurement section 223.

In such a structure, a point $\underline{C}$ is selected inside the detected contour E (S221). This is conducted by the contour internal point selection section 221. The internal point $\underline{C}$ of the contour $\underline{E}$ may be, for example, a point of the center of gravity having a coordinate (x, y) represented by the averages of all X and Y coordinates on the contour $\underline{E}$, respectively.

When the point $\underline{C}$ is selected, the measurement straight line group setting section 222 sets a measured group of straight lines arranged radially around the point of the center of gravity, that is, point $\underline{C}$ (S222). The pixel number measurement section 223 measures the number of passed pixels $\underline{p}$ for every straight line by the straight line crosses the contour (S223). At this time, the measured pixels are stored so as not to measure them a plurality of times. The addition section 224 adds the number of pixels $\underline{p}$ measured by the pixel number measurement section 223 and obtains the cross-sectional area of the heart.

Figure 38:
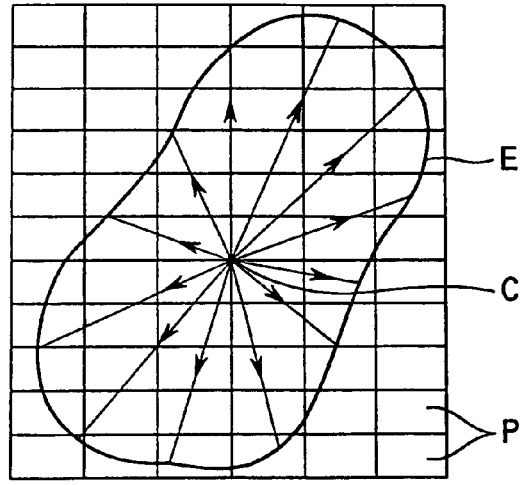
FIG. 38 is a diagram for describing how to obtain an area by counting the number of pixels in the picture processing of FIG. 36.

FIG. 38 typically shows how the processing is going on. The contour $\underline{E}$ of the heart has an almost convex, smooth shape. Therefore, if to-be-measured straight lines are set densely enough, the cross-section area of the heart can be accurately calculated by the method of this embodiment.

Figure 39:
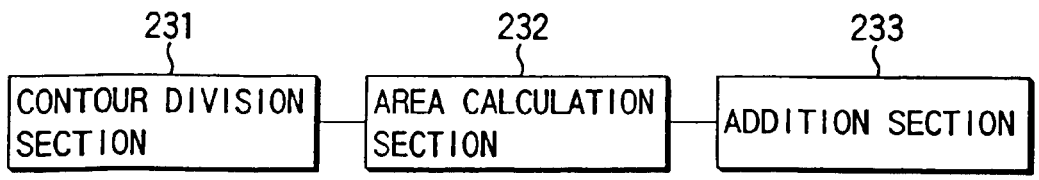
FIG. 39 is a block diagram of the picture processing apparatus in an embodiment according to the present invention.
Figure 40:
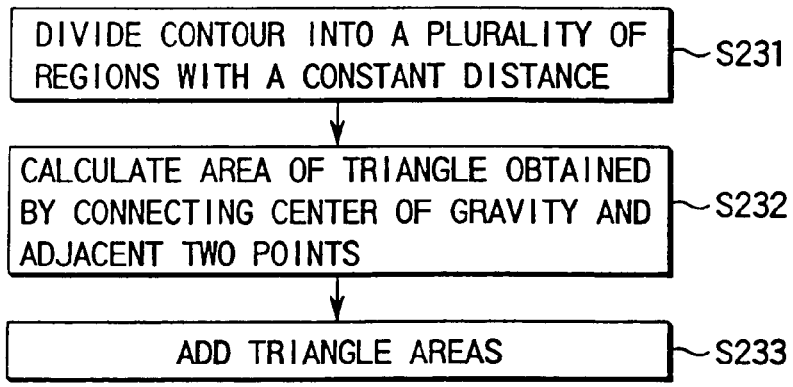
FIG. 40 is a flowchart for showing a processing flow in the picture processing apparatus in the embodiment of FIG. 39.

Another method for obtaining the cross-sectional area of the heart will be described with reference to FIGS. 39 and 40. A picture processing apparatus shown in FIG. 39 comprises a contour division section 231, an area calculation section 232 and an addition section 233. The contour division section 231 measures the length of a given contour $\underline{E}$, divides the length at predetermined intervals and obtains each division point represented as Pt. The area calculation section 232 uses the internal point $\underline{C}$ of the contour $\underline{E}$ obtained by the contour internal point selection section 221 in the embodiment of FIG. 37, creates a triangle by connecting the point $\underline{C}$, a representative point Pt and its adjacent representative points Pt for every point Pt and calculates the area of each triangle. The point $\underline{C}$ may be, for example, the point of the center of gravity having a coordinate (x, y) represented by averages of all of the X and Y coordinates on the contour $\underline{E}$.

The addition section 233 adds areas of the respective triangles obtained by the area calculation section 232 and thereby calculates the internal area of the contour.

In the apparatus of this embodiment having such a structure, the contour division section 231 measures the length of the contour $\underline{E}$ extracted by the contour extraction section, divides the length at predetermined intervals and set respective division points Pt as representative points (S231). After obtaining the respective points Pt, processing enters an area calculation step. This step is conducted by the area calculation section 232.

Figure 41:
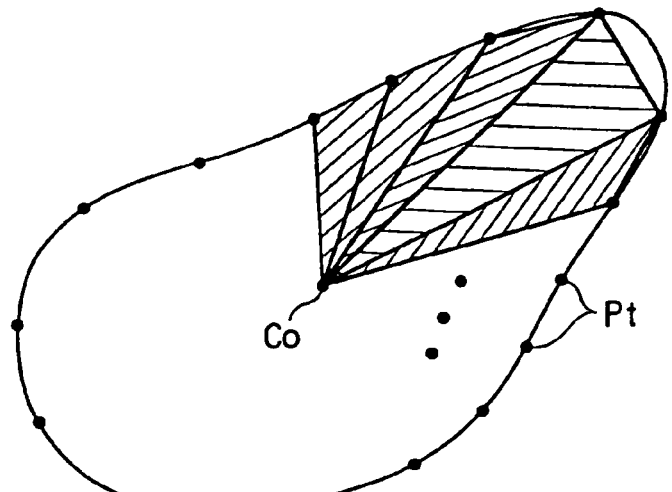
FIG. 41 is a diagram for describing how to obtain an area by polygon approximation in the processing of FIG. 40.

The area calculation section 232 creates a triangle by connecting the point C0 which is the point of the center of gravity, a representative point Pt and its adjacent representative point Pt for every point Pt (refer to FIG. 41) and calculates the area of the triangle (S232). The point C0 of the center of gravity has a coordinate (x, y) obtained by averaging all of the X and Y coordinate points on the contour, respectively.

Finally, the addition section 233 adds areas of all of the triangles and thereby calculates the internal area of the contour (S233).

As can be seen from the above, the area can be calculated by means of the polygon approximation.

The above-described methods are intended for discovering the heart terminal systole period and the heart terminal diastole period by obtaining the area of the cross-sectional heart image. However, it is possible to grasp the heart terminal systole period and the heart terminal diastole period by obtaining not only the area but also the volume as follows.

The description will now be given to methods for grasping the heart terminal systole period and the heart terminal diastole period by using the volume of the heart.

An embodiment for obtaining the volume of the heart from the cross-sectional heart image will be described with reference to FIGS. 42 through 44. This embodiment adopts a method for obtaining the heart terminal systole period and the heart terminal diastole period from the volume of the heart.

Figure 42:
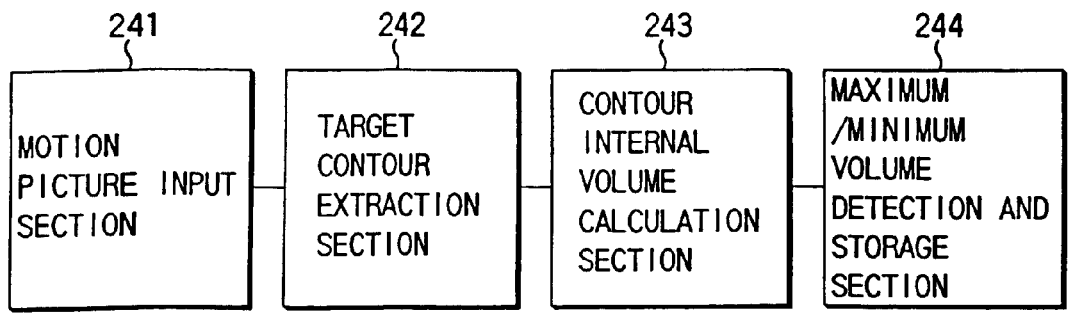
FIG. 42 is a block diagram of the picture processing apparatus in an embodiment according to the present invention.

As shown in FIG. 42, a picture processing apparatus comprises a picture input section 241, a target contour extraction section 242, a contour internal volume calculation section 243 and a maximum/minimum volume detection/storage section 244. The picture input section 241 inputs moving pictures of the heart of a subject. The target contour extraction section 242 extracts contours of the target heart from the moving pictures (frames) of the heart, respectively.

The contour internal volume calculation section 243 calculates internal volumes of the contours of the heart from the extracted contours of the heart. The maximum/minimum volume detection/storage section 244 detects a maximum volume and a minimum volume of the internal volumes of the contour obtained for respective pictures (respective frames) and stores the values while associating them with the corresponding pictures.

According to the method for obtaining the heart terminal systole period and the heart terminal diastole period from the volumes of the heart adopted in the embodiment of FIG. 42, a moving picture of the heart is first inputted from the ultrasonic diagnosis apparatus (S241). The target contour extraction section 242 then extracts the contour $\underline{E}$ of the target (cardiac wall) from the inputted moving picture (S242). The contour is extracted for every picture (every frame).

When the contour for every picture (every frame) is extracted, the contour internal volume calculation section 242 calculates the internal volume of the contour for the extracted contour (S243). The volume can be calculated by, for example, obtaining the central axis of the contour $\underline{E}$, dividing the central axis into a plurality of segments each having a predetermined distance $\underline{d}$, obtaining the volume of a circular cylinder having a diameter ri taken from one intersection between a segment passing one of the division points and perpendicular to the central axis and the contour $\underline{E}$ to another intersection therebetween and obtaining the sum of the obtained volumes of the cylinders.

Figure 43:
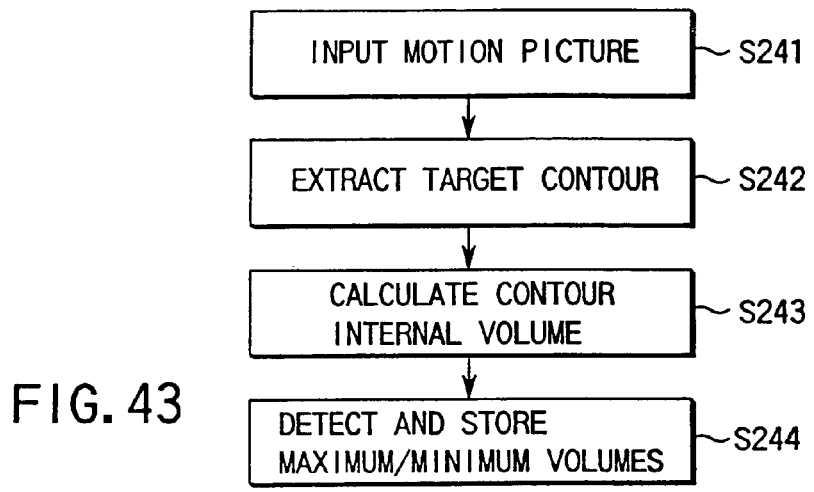
FIG. 43 is a flowchart showing a processing flow in the picture processing apparatus in the embodiment of FIG. 42.
Figure 44:
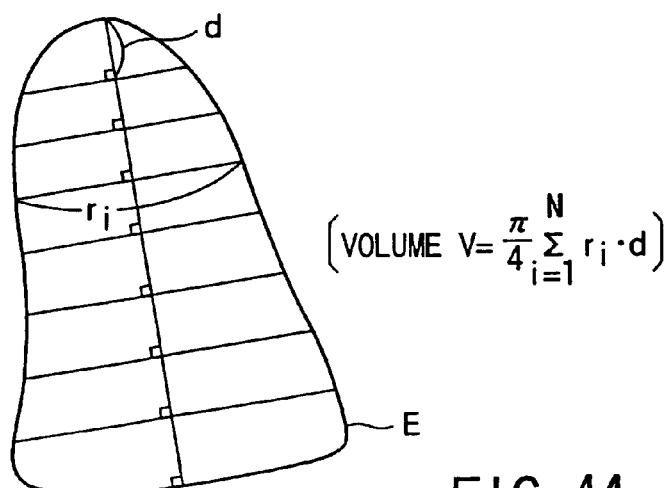
FIG. 44 is a diagram for describing how to obtain a volume of the cross section of the heart.
Figure 45:
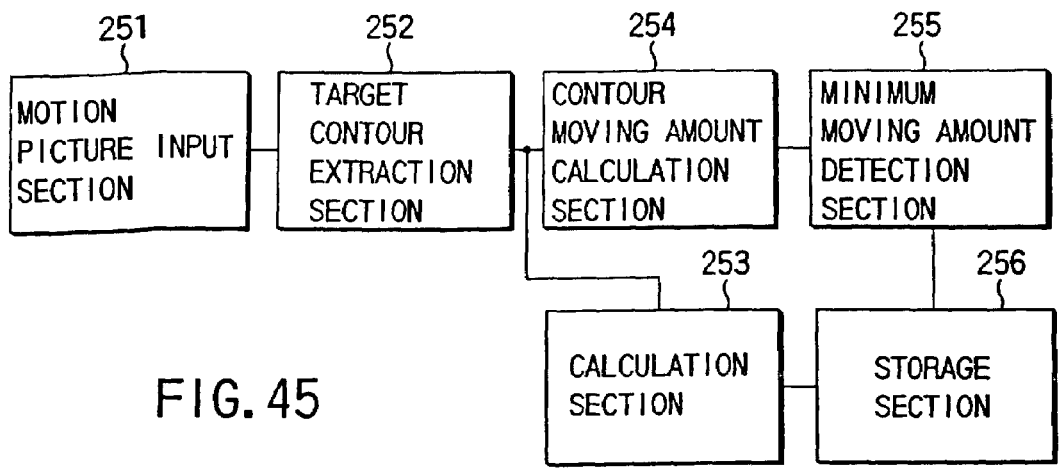
FIG. 45 is a block diagram of the picture processing apparatus in an embodiment according to the present invention.
Figure 46:
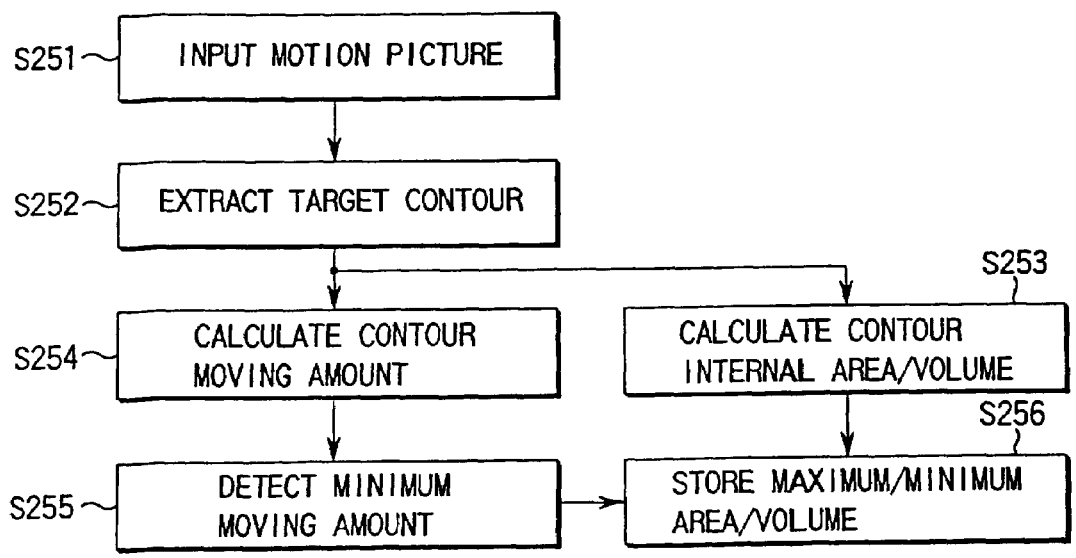
FIG. 46 is a flowchart showing a processing flow in the picture processing apparatus in the embodiment of FIG. 45.

Finally, the maximum/minimum volume detection/storage section 244 detects a maximum volume and a minimum volume in the same manner as shown in FIG. 43 and stores the values while associating them with the corresponding pictures (frames), respectively.

By using the volume measurement method, it is possible to grasp the heart terminal systole period and the heart terminal diastole period automatically.

There is a method for calculating the movement amounts between contours and obtaining a minimum value from the calculated movement values while taking it into consideration that the contour movement amount is a minimum in the terminal systole period and the terminal diastole period, and for specifying as a terminal diastole area/volume, the larger area/volume in the time phases and as a terminal systole area/volume, the smaller area/volume in the time phases. An embodiment using this method will be described hereinafter.

As shown in FIG. 34, a picture processing apparatus in this embodiment comprises a moving picture input section 251, a target contour extraction section 252, a contour internal area/volume calculation section 253, a contour movement amount calculation section 254, a minimum movement amount detection section 255 and a storage 256.

The moving picture input section 251 inputs moving pictures of the heart of a subject. The target contour extraction section 252 extracts the contour of the heart from every inputted moving picture (every frame) of the heart.

The contour moving amount calculation section 254 calculates the moving amount of the contours extracted by the target contour extraction section 252. The minimum movement amount detection section 255 obtains a minimum value and maximum value from the contour movement amounts obtained by the contour movement amount calculation section 254. The calculation section 253 calculates internal areas/volumes of the contours extracted by the target contour extraction section 252, respectively.

Among those areas/volumes, the larger area/volume and the smaller area/volume are stored as the terminal diastole period area/volume and the terminal systole area/volume, respectively while associating them with corresponding pictures. That is, a picture showing a larger area/volume in a certain time period (i.e., a picture showing a maximum area/volume in a time period among the time series pictures (frames) and a picture showing a smaller area/volume in a certain time period) are stored while associating these pictures with the corresponding values, respectively. The storage 256 stores and retains them.

In the apparatus having the above structure, moving pictures of the heart obtained from the moving picture input section 251 by, for example, the ultrasonic diagnosis apparatus are first inputted (S251). The target contour extraction section 252 extracts contours $\underline{E}$ of a target (cardiac wall) from the inputted time series moving pictures (S252), respectively.

The calculation section 253 calculates the internal areas/volumes of the contours based on the extracted contours $\underline{E}$, respectively (S253). At the same time, the contour movement amount calculation section 254 calculates contours moving amounts based on the extracted contours $\underline{E}$ (S254).

Using the fact that the movement amount becomes a minimum in the terminal expansion period and the terminal systole period, the minimum moving amount detection section 255 obtains a minimum value from the moving amounts calculated by the contour moving amount calculation section 254 (S255). The larger area/volume and the smaller area/volume in the above time phases are defined as a terminal diastole area/volume and a terminal systole area/volume, respectively and stored in the storage 256 while associating the values with the corresponding pictures (256).

As described above, by using that the contour moving amount becomes a minimum in the terminal diastole period and the terminal systole period, contour moving amounts are calculated and a minimum value is obtained from the calculated moving amounts. The larger area/volume and the smaller area/volume in those time phases are specified as a terminal diastole area/volume and a terminal systole area/volume, respectively. The heart terminal diastole period and the heart terminal systole period can be thereby discovered automatically.

Another embodiment for grasping the heart terminal diastole period and the heart terminal systole period will be described with reference to FIGS. 47 and 48.

This embodiment adopts a method for discovering a terminal systole period and a terminal diastole period of the heart from the difference in the internal areas of the respective heart contours by time-series arranging the contours obtained from the moving pictures of the heart, and for simultaneously obtaining the average movement amounts.

The structure of this embodiment comprises a contour internal area calculation section 261, a difference calculation section 262, a contour length measurement section 263 and a division section 264.

The contour internal area calculation section 261 calculates internal areas of contours from the contours of a target extracted from the target contour extraction section 252. The difference calculation section 262 arranges pictures in a time series manner and sequentially subtraction-processes the contour internal areas of the pictures, thereby obtaining time differences in areas as a result of the subtraction-processing conducted for continuous time periods. The contour length measurement section 263 counts the number of pixels on the contours and thereby measures contour lengths. The division section 264 divides time differences of area by the contour lengths and thereby obtains an average movement amount.

To obtain the average movement amount of the heart, according to this embodiment, contours $\underline{E}$ of ultrasonic cross-sectional images of the heart inputted as moving pictures are extracted and internal areas of the contours $\underline{E}$ are obtained, respectively (S261). The contour internal area calculation processing is conducted by the contour internal area calculation section 261. The pictures are arranged in a time series manner and the internal areas of the contours $\underline{E}$ are subtraction-processed in the generation order, to thereby obtain time differences of area as a result of the subtraction-processing conducted for continues time periods (S262). This processing is conducted by the difference calculation section 262.

Next, the contour length measurement section 263 measures contour lengths by counting the number of pixels on the contours E (S263). Finally, the division section 264 obtains an average moving amount by dividing time differences of areas by the contour lengths (S264).

As can be understood from the above description, it is possible to discover the terminal systole period and the terminal diastole period of the heart by arranging heart contours obtained from heart moving pictures in a time series manner and calculating differences in the internal areas of the heart contours. It is also possible to obtain useful diagnosis information including the heart movement amounts by obtaining an average heart moving amount. It should be emphasized that they can be realized automatically.

Now, referring to FIGS. 49 and 50, description will be given to an embodiment for obtaining the moving amount of the heart by adopting a method for obtaining characteristic points on contours, for estimating movements of the respective characteristic points and thereby for obtaining an average movement amount.

As shown in FIG. 49, the picture processing apparatus in this embodiment comprises a characteristic point detection section 271, a moving vector detection section 272 and a moving amount calculation section 273. The characteristic point detection section 271 obtains characteristic points on contours E extracted by the target contour extraction section 252, respectively. The moving vector detection section 272 correlates and collates a region in the vicinity of the obtained characteristic point and a picture in a time phase following the time phase of the former picture and detects the movement of the difference in coordinate between a point having the largest correlation value and an original characteristic point as a moving vector. The moving amount calculation section 273 obtains an average moving amount from moving vectors of respective characteristic points by statistic processing.

The apparatus in this embodiment having such a structure extracts contours E of cross-sectional images of the heart inputted as moving pictures and obtains characteristic points of the contours E, respectively.

To be more specific, the characteristic point detection section 271 obtains characteristic points based on the contours E of the cross-sectional images of the heart to obtain movement amounts (S271). These characteristic points may be selected by, for example, obtaining a point having a large curvature change on a contour E as a characteristic point. Alternatively, a variance of adjacent points on a contour E is obtained and a point having a value not less than a predetermined value may be selected as a characteristic point. Furthermore, by dividing a contour E into a plurality of parts at predetermined intervals, a characteristic point may be selected.

Processing by the moving vector detection section 272 then starts. The moving vector detection section 272 estimates movements of characteristic points on contours E.

In this embodiment, the evaluation is made as follows. A region in the vicinity of a characteristic point and a picture in the following time phase are correlated and collated and detects a difference in coordinate between a point having the largest correlation value and an original characteristic point as a moving vector (S272).

Processing by the moving amount calculation section 273 then starts. The moving amount calculation section 273 obtains an average moving amount from moving vectors of respective characteristic points by statistic processing (S273). In this embodiment, the averages of x components and y components of the respective moving vectors are obtained and the magnitudes are calculated, whereby an average moving amount is obtained.

In short, the present invention is characterized in that contours of a target are extracted from moving pictures obtained by, for example, an ultrasonic diagnosis apparatus, that internal areas of the extracted contours are calculated and that maximum and minimum areas are detected as a terminal diastole area and a terminal systole area, respectively.

Moreover, the picture processing method according to the present invention is characterized in that contours of the target are extracted from moving pictures obtained by, for example, the ultrasonic diagnosis apparatus, that contour internal volumes are calculated using the extracted contours, and that the maximum and minimum values are obtained and detected as a terminal diastole volume and a terminal systole volume, respectively.

In addition, the picture processing method according to the present invention is characterized in that contours of a target are extracted from moving pictures obtained by, for example, the ultrasonic diagnosis apparatus, that areas or volumes showing the smallest moving amount are obtained from moving amounts on a time-by-time basis by using those extracted contours and that the maximum area/volume and the minimum area/volume out of the obtained areas/volumes are detected as a terminal diastole area/volume and a terminal systole area/volume, respectively.

According to the present invention, areas or volumes are calculated from cross-sectional heart images obtained as moving pictures based on information about the extracted heart contours. The calculated areas/volumes are compared in a time series manner. As a result, it is possible to properly determine the terminal diastole period and the terminal systole period of the heart.

According to the present invention, concrete areas or volumes of the heart are obtained and, based on these obtained values, the terminal diastole period and the terminal systole period of the heart can be properly determined. This makes it possible to obtain objective measurement information useful to the diagnosis of the subject's heart function. Besides, since the information can be obtained automatically, the burden on the operator can be reduced.

It is noted that the present invention should not be limited to the above-described embodiments. Various modifications are possible. Furthermore, not only ultrasonic pictures but also cross-sectional pictures of CT scan or MRI as well as X-ray television pictures can be used in the present invention. It may be possible to use the present invention in fields other than the medical field.

Since the present invention utilizes moving pictures, pictures (or frame pictures) changing moving states in accordance with heartbeats can be inputted in a time series manner. Heart contours of those pictures in respective time phases are extracted and processed. However, it is not necessary to use all of the frame pictures. Instead, among the time series pictures (or frame pictures), some of the pictures which reflect moving states in a systole period and an diastole period may be selected and processed. Therefore, various modifications are possible depending on the circumstances.

The methods described with reference to the flowcharts of FIGS. 33, 35, 37, 40, 43, 46, 48 and 50 can be stored in a storage medium including a magnetic disc (such as a floppy disc and a hard disc) and an optical disc (such as a CD-ROM and a DVD) as programs which can be executed by a computer and distributed widely.

According to the embodiments of the present invention, it is possible to automatically obtain either areas or volumes or both of them in the terminal diastole period and the terminal systole period of the heart for the measurement of the pumping function which is important to the diagnosis of a disease, by using moving pictures obtained by, for example, an ultrasonic diagnosis apparatus. Therefore, if cross-sectional heart images are inputted as moving pictures, for example, then the terminal diastole period and the terminal systole period of the heart can be accurately determined from concrete values of the obtained areas and/or volumes based on the cross-sectional heart images, and the heart pumping function can be quantitatively obtained. Thus, the present invention can advantageously facilitate using objective measurement information which is useful to the diagnosis of the subject's heart function.

Now, description will be given to a heart function analysis support apparatus and method for accurately associating the cardiac wall contours and facilitating the evaluation of local movement states of the cardiac wall so that the display of information calculated from the contour information which can be easily evaluated is realized.

Figure 51:
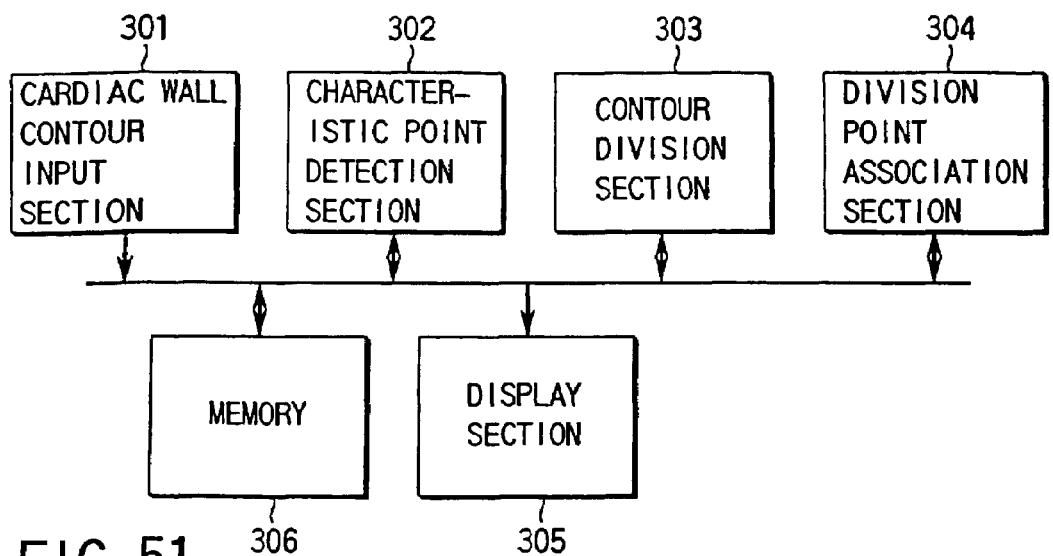
FIG. 51 is a block diagram of the cardiac function analysis support apparatus in an embodiment according to the present invention.

A heart function analysis apparatus shown in FIG. 51 comprises a cardiac wall contour input section 301 for inputting cardiac wall contour information, a characteristic point detection section 302 for detecting or inputting characteristic points on contours such as a cardiac apex and an annulus valva from the hear wall contours, a contour division section 303 for dividing the cardiac wall contours based on the characteristic points, a division point association section 304 for associating division points of moving pictures in a plurality of time phases, a display section 305 for classifying the divided cardiac wall contours into regions useful for diagnosis and for displaying the divided contours by means of at least one of numerical display, graph display, color display of the cardiac wall and a memory for storing contour information or division point information.

In the present apparatus having the above structure, the cardiac wall contour input section 301 inputs cardiac wall contour information. Time series cross-sectional images of the subject's heart are obtained from, for example, the ultrasonic diagnosis apparatus. Contours of the heart are extracted based on the obtained images. The extracted contours are used as the cardiac wall contour information. The cardiac wall contour information is stored in the memory 6. The cardiac wall contour information is fed to the characteristic point detection section 302.

When the cardiac wall contour information is inputted, the characteristic point detection section 302 detects characteristic points on contours such as a cardiac apex and an annulus valva from the cardiac wall contours based on the cardiac wall contour information. This can be automatically calculated by using the curvature of contours based on the shapes of the cardiac wall contours (automatic detection processing). It is also possible to manually input characteristic points using, for example, a mouse (manual input operation).

The contour division section 303 divides the cardiac wall contours based on the characteristic points obtained by the characteristic point detection section 302. The division information obtained by the division processing is stored in the memory 6. When the cardiac wall contours are divided, the division point association section 304 associates the division points on the contours of pictures in a plurality of time phases. The display section 305 classifies the divided cardiac wall contours into regions useful for diagnosis and displays them by means of at least one of numerical display, graph display and color display of the cardiac wall.

The detailed processing of the heart function analysis apparatus having the above structure will be described with reference to the flowchart of FIG. 52.

First, cardiac wall contour information is inputted from the cardiac wall contour input section 301. The cardiac wall contours may be inputted manually using, for example, a mouse on pictures or may be contour information obtained as a result of picture processing and the like (FIG. 53 and step A1 of FIG. 52).

Figure 54:
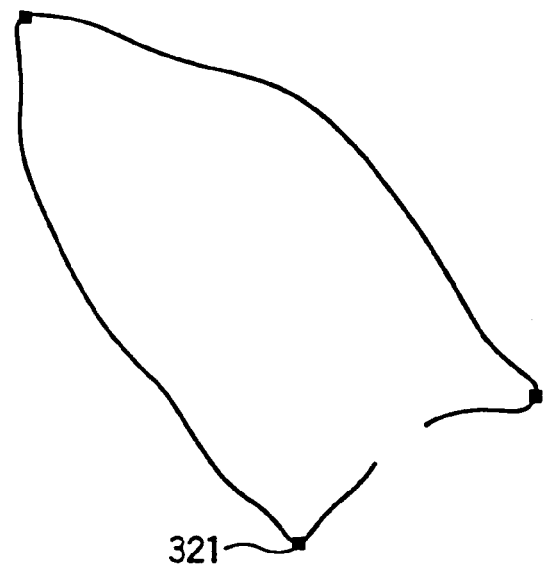
FIG. 54 is an explanatory diagram of the detection of characteristic points in the embodiment of FIGS. 52 and 53.

Next, characteristic points on the cardiac wall contours are detected by the characteristic point detection section 302. The characteristic point may be inputted manually using, for example, a mouse or calculated automatically using information about the curvature of contours based on the shapes of the cardiac wall contours (FIG. 54 and step A2 of FIG. 52).

The inputted cardiac wall contours are then divided based on the detected characteristic points (processing conducted in the contour division section 303).

The division of the cardiac wall contours is conducted by the following method.

This embodiment illustrates a method for dividing cardiac wall contours while a point of a cardiac apex and an annulus valva 302 are used as characteristic points.

Figure 55:
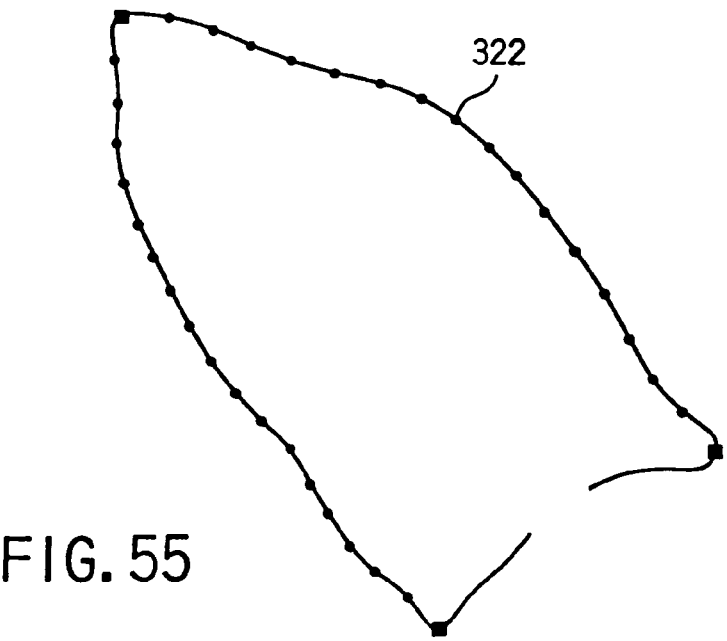
FIG. 55 is an explanatory diagram of contour division in the embodiment of FIGS. 52 and 53.

As shown in FIG. 55, a portion from a right annulus valva to a cardiac apex is divided into n parts and a portion from the cardiac apex to a right annulus valva is divided into m parts. Division points 322 are allotted with particular numbers, respectively and stored (Step A3 of FIG. 52). The division numbers m and n can be appropriately set in accordance with the density for analyzing the movement of the cardiac wall.

Figure 52:
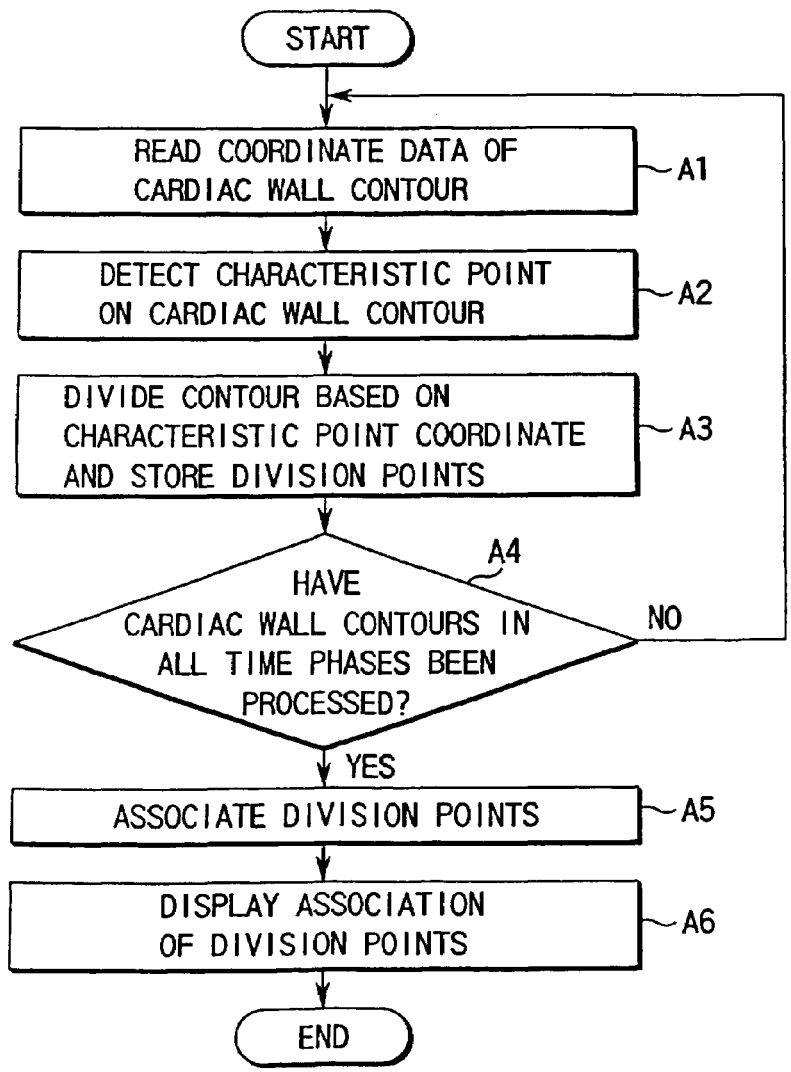
FIG. 52 is a flowchart for showing a processing flow in the cardiac function analysis support apparatus of FIG. 51.
Figure 53:
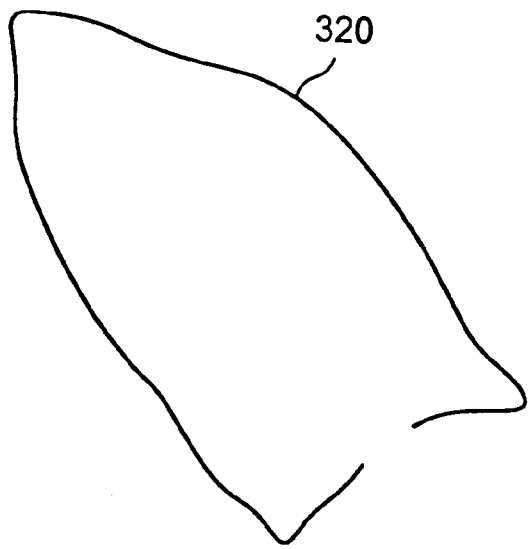
FIG. 53 is an explanatory diagram of the inputted contour in the embodiment of FIGS. 52 and 53.

The above-described processing steps are conducted for contour data in all time phases (Step A4 of FIG. 52). The division of the cardiac wall contours is finished.

When the cardiac wall contours are divided, division points for respective time phases are associated. More specifically, division points having the same number are associated with one another (Step A5 of FIG. 52). This step is conducted by the division point association section 304.

Figure 56:
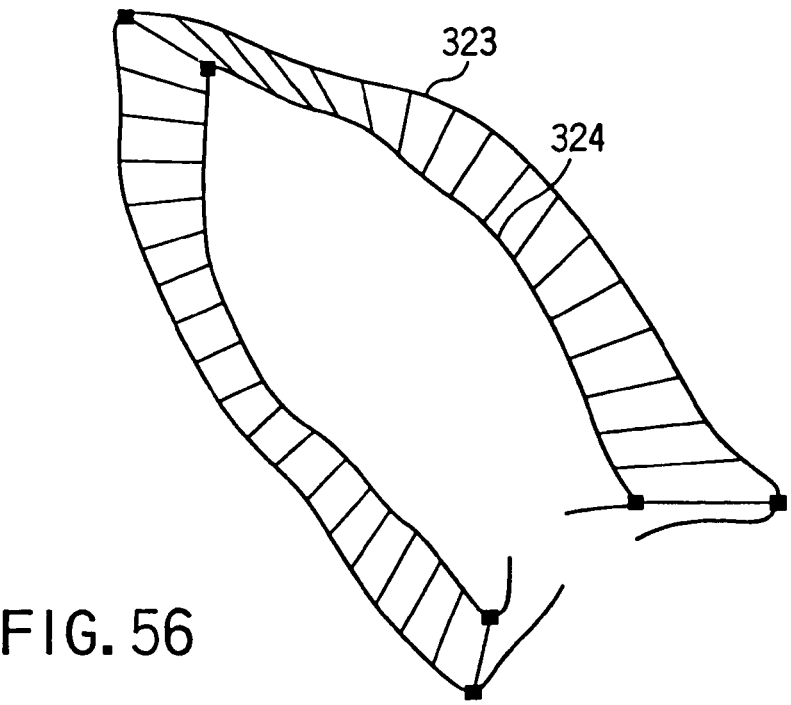
FIG. 56 is an explanatory diagram of association of cardiac wall contours in a plurality of time phases in the embodiment of FIGS. 51 and 52.

As described above, according to the embodiment shown in FIGS. 51 and 52, the cardiac apex and the annulus valva of the heart having shapes of definite characters are used as characteristic points. Due to this, positions of cardiac apex and the annulus valva can be accurately associated. Furthermore, according to the embodiments thereof, the cardiac wall contours are divided based on the cardiac apex and the annulus valva. Due to this, as shown in FIG. 56, association of the wall contours in two time periods can be made more appropriately than that by the center line method.

Figure 57:
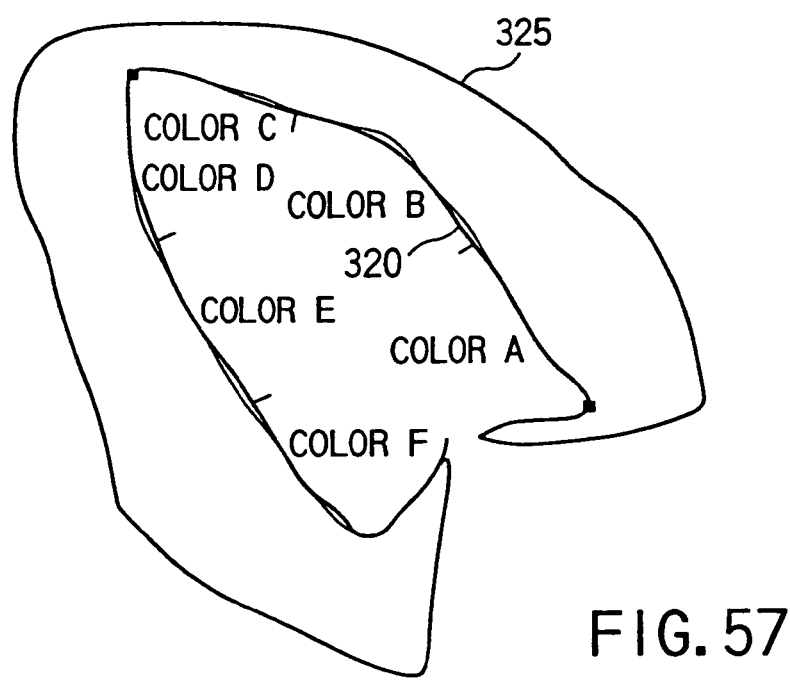
FIG. 57 is an explanatory diagram of a display method in the embodiment of FIGS. 51 and 52.

The results of the association of division points, if finished, are displayed (Step A6 of FIG. 52). In this case, as shown in FIG. 57, the cardiac wall 325 is displayed. Inside the cardiac wall 325, division points from left annulus valva to the cardiac apex and those from the cardiac apex to the right annulus valva are further classified into three parts, respectively. Contour lines (cardiac wall contours 320) are divided by colors A, B, C, D, E and F for respective classified parts and superimposed over the cross-sectional heart pictures.

The three classified parts may be, for example, a base portion, a central portion and a cardiac apex portion so as to be useful for diagnosis. By classifying the cardiac wall and displaying the divided contour lines by coloring them for respective classified parts, it is possible to appropriately divide the cardiac wall region and to easily and definitely discover the position of the cardiac wall region on the picture.

Figure 58:
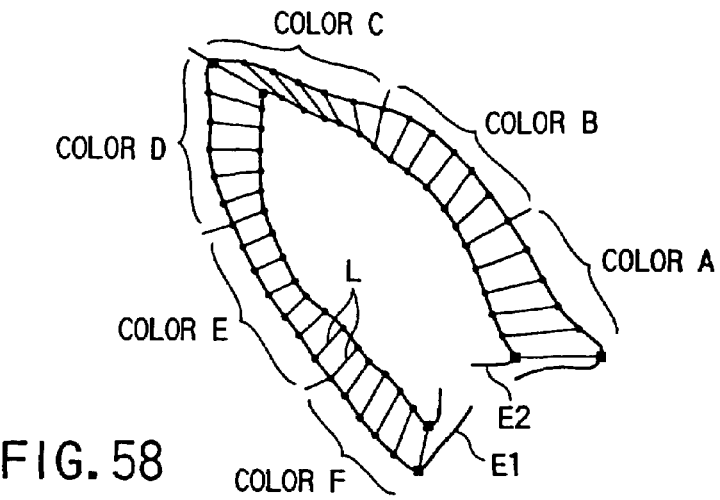
FIG. 58 is an explanatory diagram of a display method in the embodiment of FIGS. 51 and 52.

There is a different display method. A contour E1 in a certain time phase (a certain time period) as a reference time phase is pre-set with respect to the periodic diastole and systole movement of the heart. As shown in FIG. 58, division points on a contour E1 in the reference time period and those on a contour E2 (which is one of present target contours and a contour in a different time phase) in a present time phase are connected to one another by straight lines L, respectively. By so doing, it is possible to easily grasp which part of the cardiac wall region moves to what degree with respect to the cardiac wall contour in the reference time phase.

It is also possible to display contour division results of pictures in a plurality of continuous time phases as moving pictures. By using the moving picture display method, the movement state of the cardiac wall can be displayed such that they can be grasped more easily. FIGS. 57 and 58 show an example of displaying the contours by classifying divided parts with different five colors of A to F. However, this is nothing but one example. It is not always necessary to display all contours with different colors. As long as the division parts of the contours can be recognized, it is not required to color the contours. Different types of lines may be used for classification. Alternatively, such a display method as to display at least adjacent contours with different colors so as to discriminate contours, may be adopted.

Figure 59:
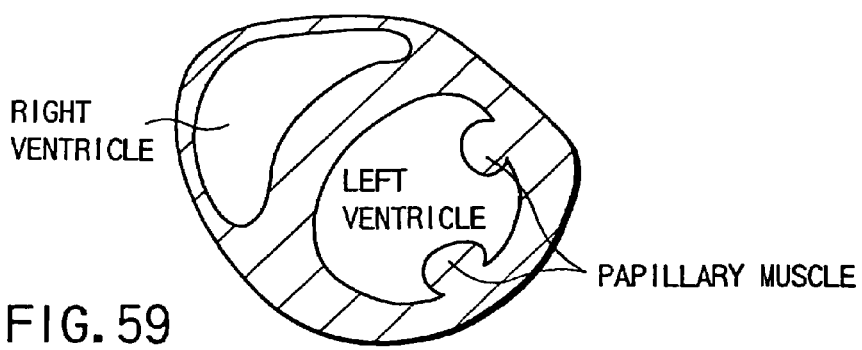
FIG. 59 is a diagram for describing an example of applying the embodiment of FIGS. 51 and 52 to a short axis heart picture.

In the meantime, since a heart is ellipsoidally sphere, there are a cross section along a longer axis and a cross section along a shorter axis. The above descriptions have been described while using a cross section along a longer axis as a cross-sectional heart image. The same processing is possible even if using a cross section along a shorter axis as a cross-sectional heart image as shown in FIG. 59. In that case, accurate association can be realized by using, as a characteristic point, a papillary muscle which is one tissue of the heart. By using this, it is possible to even analyze movements which are not perpendicular to a cardiac wall contour such as a heart torsion movement.

In the embodiment shown in FIGS. 51 and 52, the cardiac wall contours are divided into a predetermined number of parts to set division points and the cardiac wall contours in time periods of the beating heart are displayed for respective division points to clarify the division parts. In the embodiment, as characteristic points serving as reference points to the division parts on the heart contours, the cardiac apex and the annulus valva of the heart having shapes of definite characters are used.

Next, description will be given to an embodiment wherein division points are set by dividing cardiac wall contours into a predetermined number of parts, movement distances of the division points in respective time periods of the beating heart from the corresponding division points in a reference time period are calculated and the information about movement distances of respective division points is displayed while reflecting on the pictures. In this case, cardiac apex and the annulus valva of the heart having shapes of definite characters are used as characteristic points serving as reference points to the division points on the heart contours.

Figure 60:
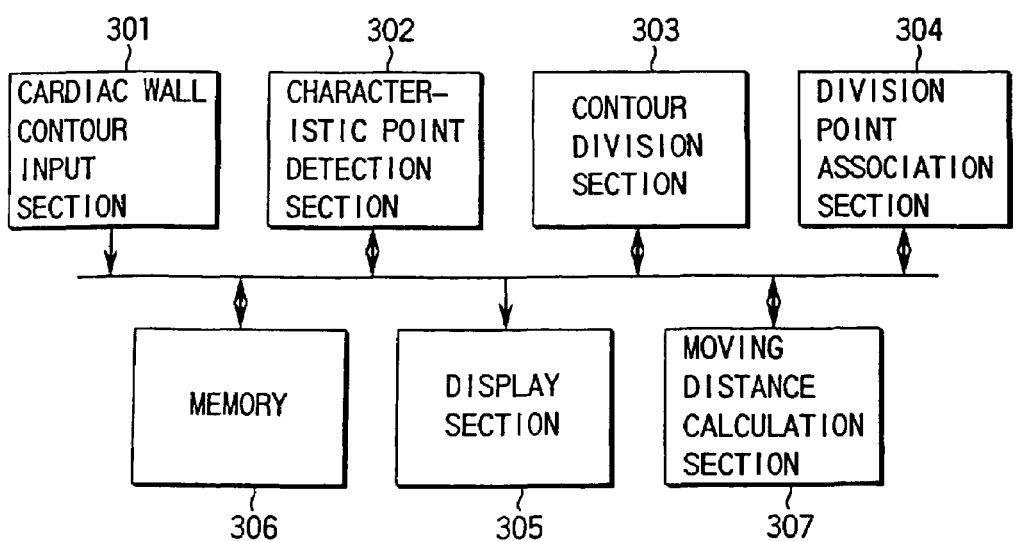
FIG. 60 is a block diagram of the cardiac function analysis support apparatus in an embodiment according to the present invention.

As shown in FIG. 60, the apparatus in this embodiment comprises a cardiac wall contour input section 301 for inputting cardiac wall contour information, a characteristic point detection section 302 for detecting or inputting characteristic points on cardiac wall contours such as the cardiac apex and the annulus valva, a contour division section 303 for dividing the cardiac wall contours based on the characteristic points, division point association section 304 for associating division points of the contours from pictures in a plurality of time phases, a display section 305 for classifying the divided cardiac wall contours into parts useful for diagnosis and display them by means of at least one of numerical display, graph display and color display of the cardiac wall, a memory 306 for storing contour information or division point information and a movement distance calculation section 307 for calculating movement distances of respective division points.

That is, the structure of the apparatus in this embodiment is characterized by comprising the movement distance calculation section 307 for calculating movement distances of respective division points in addition to the structure of the embodiment FIG. 51. A new display function of reflecting movement distances of the division positions of the divided cardiac wall contours is also added to the display section 305.

In the apparatus according to this embodiment, the inputted cardiac wall contours in respective time phases, that is, cardiac wall contours of respective time series pictures are divided based on such characteristic points as the cardiac apex and the annulus valva and the pictures in a plurality of time phases, that is, time series pictures are associated with one another. These procedures are the same as described in the embodiment of FIG. 51 (in steps B1 to B5 of FIG. 61).

Figure 61:
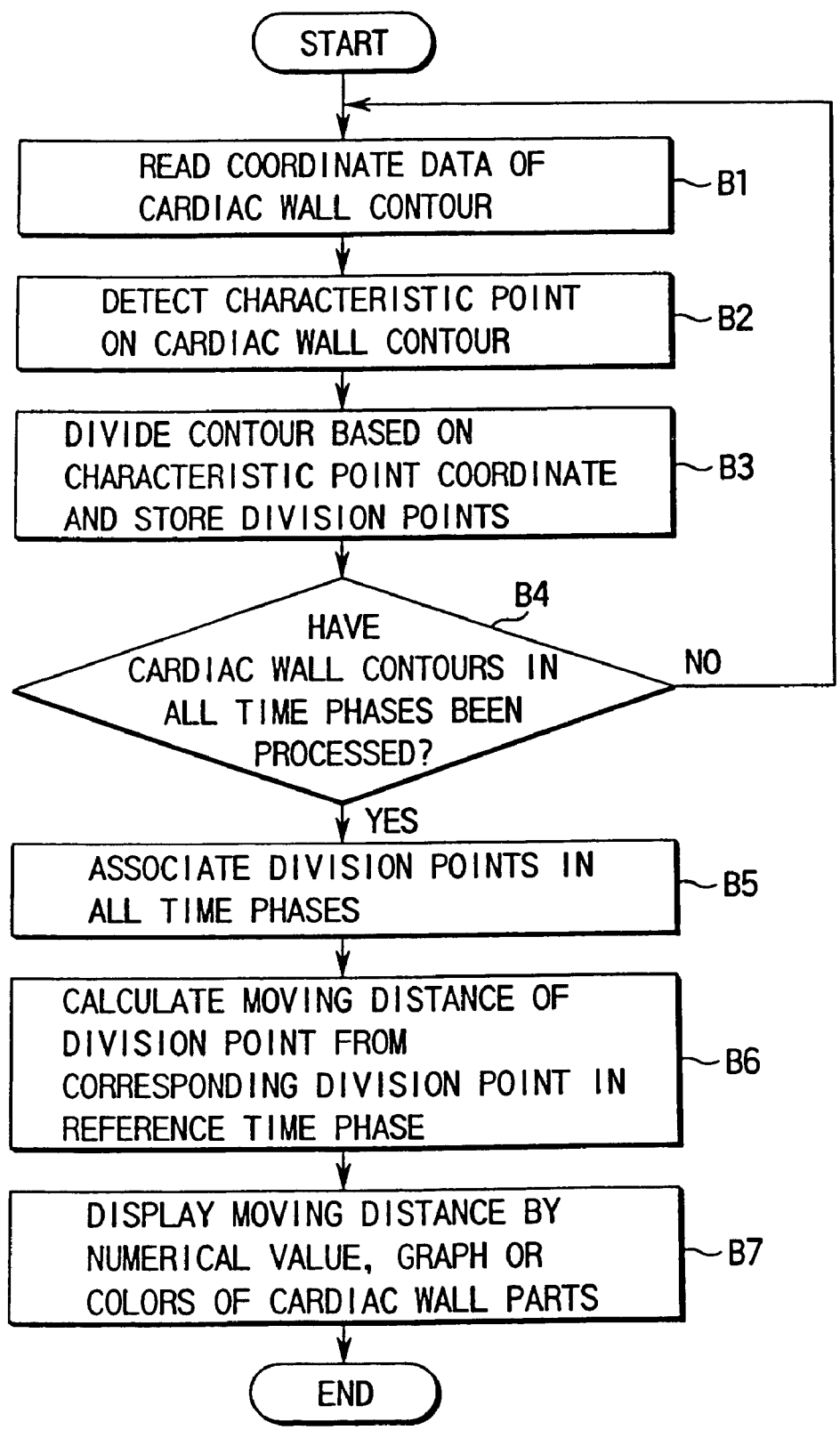
FIG. 61 is a flowchart for describing a processing flow of the cardiac function analysis support method in the embodiment of FIG. 60.

After dividing the cardiac wall contours, movement distances of division points in respective time phases from the corresponding division points in the pre-set time period are calculated, respectively (Step B6 of FIG. 61). The calculation step is conducted by the movement distance calculation section 307. Movement distances of the division points in respective time phases from the corresponding division points in the reference time period will be obtained as follows.

Among time phases of the beating heart, an i-th time phase is highlighted. A coordinate of the n-th division point of the cardiac wall contour on the cross-section of the heart in the i-th time phase on the picture is represented as $$(X, Y) = (X_{i,n}, Y_{i,n}) \tag{11}$$

If a reference time phase is the o-th time phase and a time phase for calculating a movement distance is the j-th time phase, the movement distance $d_{j,n}$ of the n-th division point is calculated as $$d_{j,n} = \sqrt{(X_{j,n} - X_{o,n})^2 + (Y_{j,n} - Y_{o,n})^2} \tag{12}$$

Based on the calculation formulas, movement distances are calculated. Next, in accordance with the calculated movement distances, the display section 305 gives the cardiac walls contours colors, superimposes the colored contours over the cross-sectional heart picture and displays them (Step B7 of FIG. 14). In regard of coloring, if the color phase on the n-th division point in the j time phase is defined as Cj,n as in the case of the formula (3), the portion of the cardiac wall having a small movement distance is colored blue and that having a large movement distance is colored red, for example. By so doing, it is possible to grasp the movement state of the cardiac wall visually, which greatly helps understand the movement state of the cardiac wall.

$$C_{j,n}(°) = Mod(k \cdot d_{j,n}, 360) \tag{13}$$

Here, k denotes a constant and Mod (,) denotes a reminder.

Figure 62:
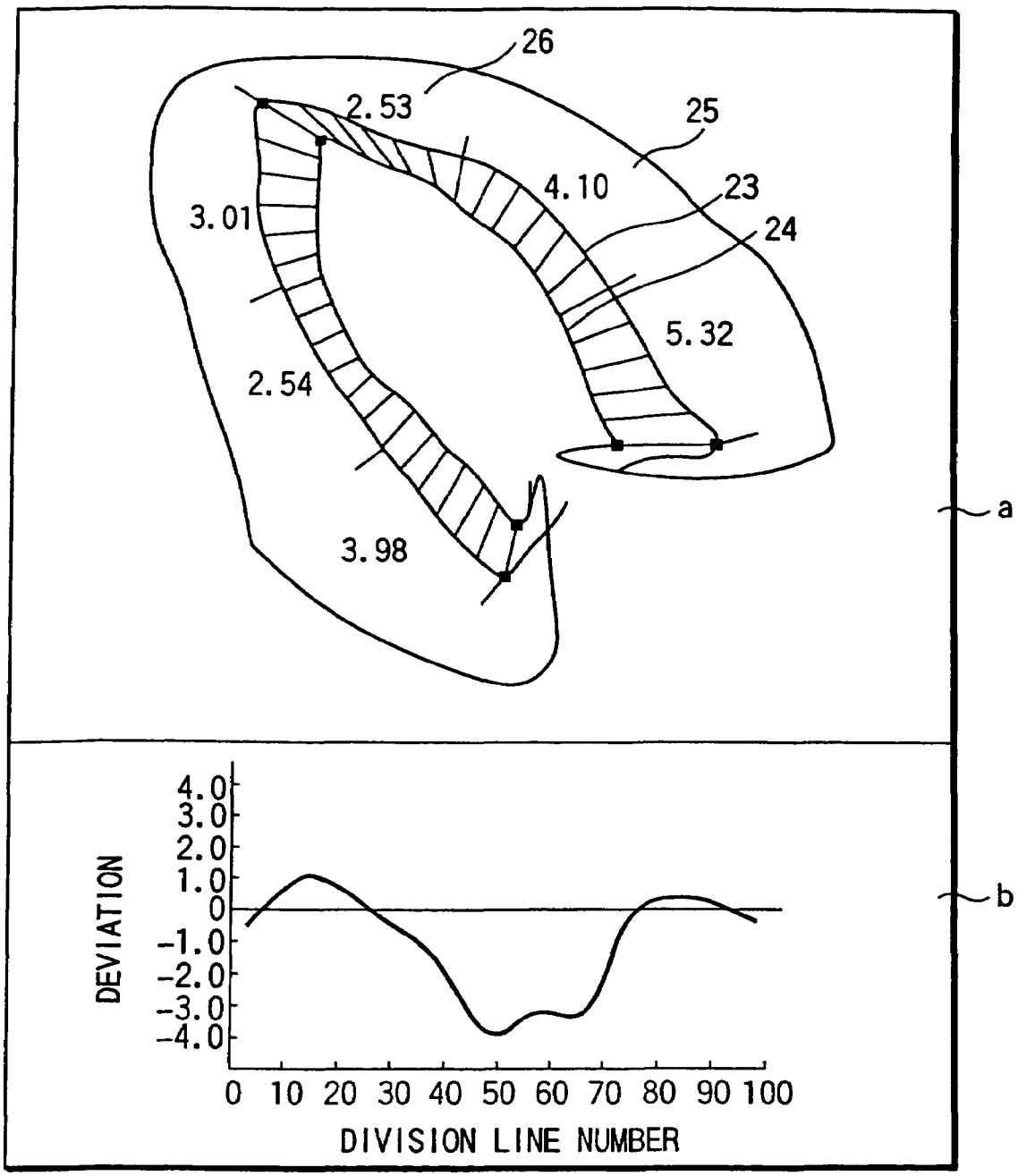
FIG. 62 is an explanatory diagram of a display method in the embodiment of FIGS. 60 and 61.

As shown in FIG. 62, movement distances for contours (division points of contours) are expressed on a graph (b of FIG. 62). Alternatively, a cardiac wall contour is classified into a plurality of parts and the statistic of movement distances for every classified cardiac wall part is calculated and is displayed numerically (a of FIG. 62).

By thus displaying numerical information, it is possible to obtain quantitative information. If, for example, an average value for every part of the heart contours is calculated as statistic, the average $E_{j,i}$ of the i-th cardiac wall part of the picture in the i-th time phase is expressed as $$E_{j,i} = \frac{1}{N} \sum_{n \in i \text{ th cardiac wall}} d_{j,n} \tag{14}$$

where N denotes the number of division points belonging to the i-th cardiac wall part.

Figure 63:
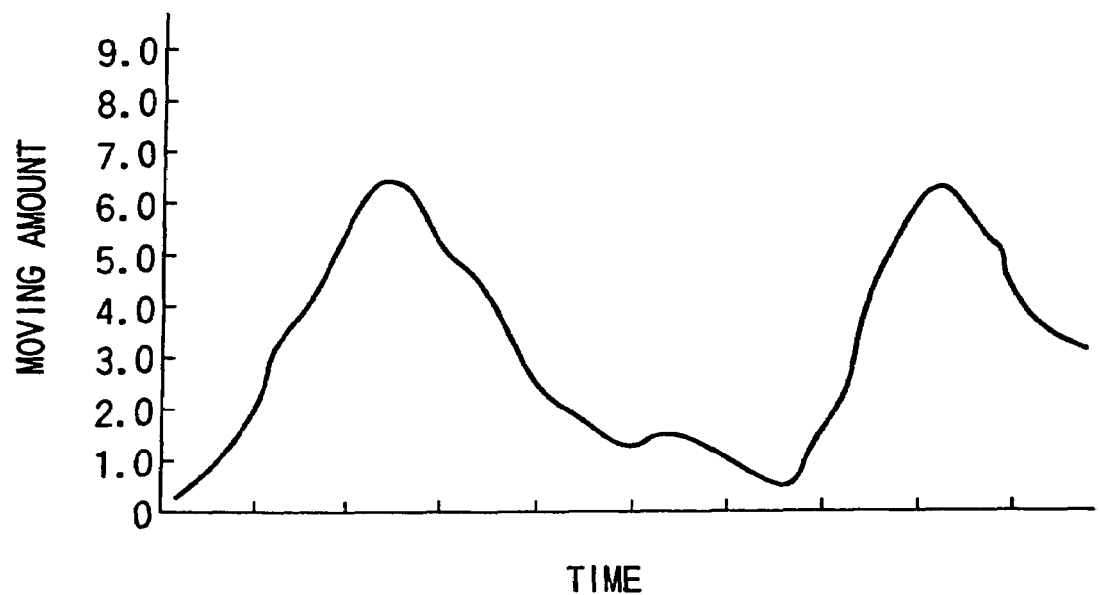
FIG. 63 is an explanatory diagram of a method for displaying velocity change in the embodiment of FIGS. 60 and 61.

As shown in FIG. 63, a change in movement distances is expressed in a time series manner and a time series change may expressed on a graph. Furthermore, velocities of the cardiac wall parts can be calculated by differentiating movement distances based on time phases. A velocity of the cardiac wall part perpendicular to an ultrasonic beam cannot be obtained as a Doppler signal in the ultrasonic diagnosis apparatus. However, by adopting the above method, it is possible to obtain velocity information of cardiac wall parts irrespectively of the direction of the beams.

Figure 64:
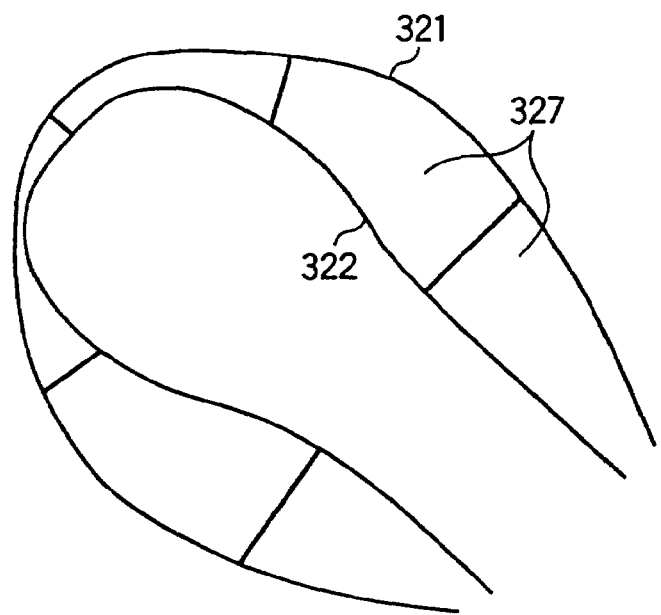
FIG. 64 is an explanatory diagram of a movement area in the embodiment of FIGS. 60 and 61.

As shown in FIG. 64, a positional difference is obtained for every division point between the contour 321 in time phase A and the contour 322 in time phase B and the differences are expressed on the picture as areas. If movement areas for the respective cardiac wall portions are calculated based on division points and expressed, the state of systole movement can be grasped for every cardiac wall portion. This is very useful as diagnosis information.

According to the embodiment of FIG. 60, the cardiac wall contours are divided into a plurality of parts and divided parts are determined. Movement distances of divided parts in time phases of the beating heart, from corresponding divided parts in the reference time phase are calculated, respectively. Information about the movement distances of the contours for divided parts is reflected on the picture and displayed.

Now, description will be given to an embodiment wherein Doppler information is used, cardiac wall contours are divided into a plurality of parts and velocity information based on the Doppler information for every part is obtained and an picture is displayed by reflecting the obtained velocity information for every part of the cardiac wall contours on the picture.

Figure 65:
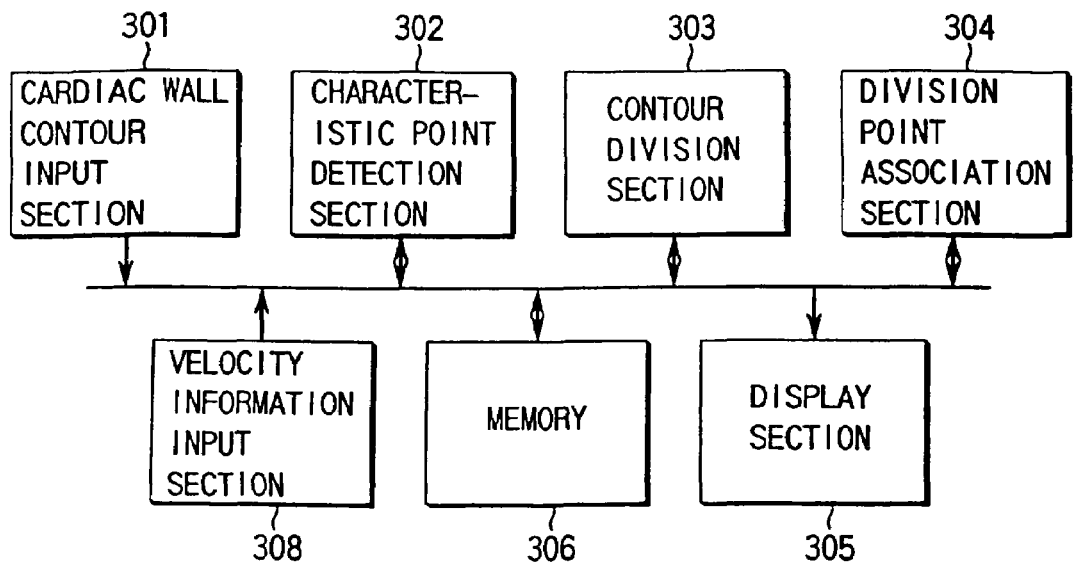
FIG. 65 is a block diagram of the cardiac function analysis support apparatus in an embodiment according to the present invention.

As shown in FIG. 65, the apparatus in this embodiment comprises a cardiac wall contour input section 301 for inputting cardiac wall contour information, a characteristic point detection section 302 for detecting or inputting characteristic points on contours such as a cardiac apex and an annulus valva, a contour division section 303 for dividing cardiac wall contours based on characteristic points, a division point association section 304 for associating division points in different time phases with one another, a display section 305 for classifying the divided cardiac wall contours into a plurality of parts useful for diagnosis and displaying the parts by means of at least one of numerical display, graph display and color display of cardiac wall, a memory 306 for storing contour information or division point information and a velocity information input section 308 for inputting velocity information obtained from Doppler signals in the ultrasonic diagnosis apparatus.

To be more specific, the structure of the embodiment FIG. 65 is characterized by comprising the velocity information input section 308 for inputting velocity information obtained from Doppler signals in the ultrasonic diagnosis apparatus in addition to the elements of the apparatus in the embodiment of FIG. 51. Additionally, the display section 305 is provided with a function of classifying velocity information about tissues obtained from Doppler signals for every cardiac wall part using division points of the divided cardiac wall contours and displaying the velocity information on the division points, respectively.

The processing by the apparatus in FIG. 65 will be described with reference to the flowchart of FIG. 66. The apparatus divides cardiac wall contours in respective inputted time phases based on characteristic points such as a cardiac apex and an annulus valva (in steps C1 to C3 of FIG. 66). This processing steps are the same as those in the first embodiment. In this embodiment, information obtained from Doppler signals is inputted (Step C4 of FIG. 66). That is, by using the ultrasonic diagnosis apparatus having a Doppler signal measurement function, Doppler signals of the heart are obtained. The velocity information input section 308 obtains velocity information from the Doppler signals and inputs the velocity information.

Figure 66:
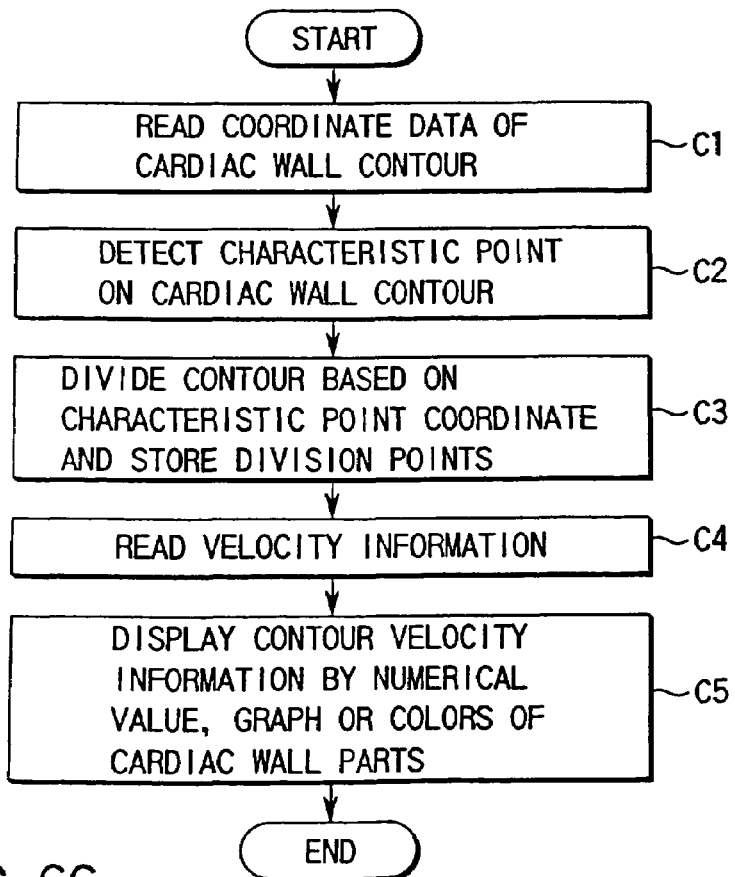
FIG. 66 is a flowchart for describing a processing flow of the cardiac function analysis support method in the embodiment of FIG. 65.

Thereafter, using division points of the divided cardiac wall contours, velocity information about tissues obtained from Doppler signals is classified for every cardiac wall part and displayed on respective division points (Step C5 of FIG. 66). The step is conducted by the display section 305.

The detailed displayed contents are as follows. By way of example, description will be given to a case of classifying a part from a left annulus valva to a cardiac apex and a part from the cardiac apex to a right annulus valva into three parts, respectively.

First, a plurality of division points are provided on cardiac wall contours. Using the division points, the cardiac wall contours are classified into a plurality of parts each having a required distance. For example, a part from the left annulus valva to the cardiac apex of a cardiac wall contour and a part from the cardiac apex to a right annulus valva are classified into three regions; i.e. a base, a central portion, a cardiac apex portion in the division order, respectively.

Next, velocity information on the respective division points is added for every classified region and an average is calculated. If the velocity on the n-th division point is Dopplern, the average Ei for every cardiac wall part is calculated by formula (5) as follows:

$$M_i = \frac{1}{N} \sum_{n \in i \text{ th cardiac wall}} Doppler_n \qquad (15)$$

Figure 67:
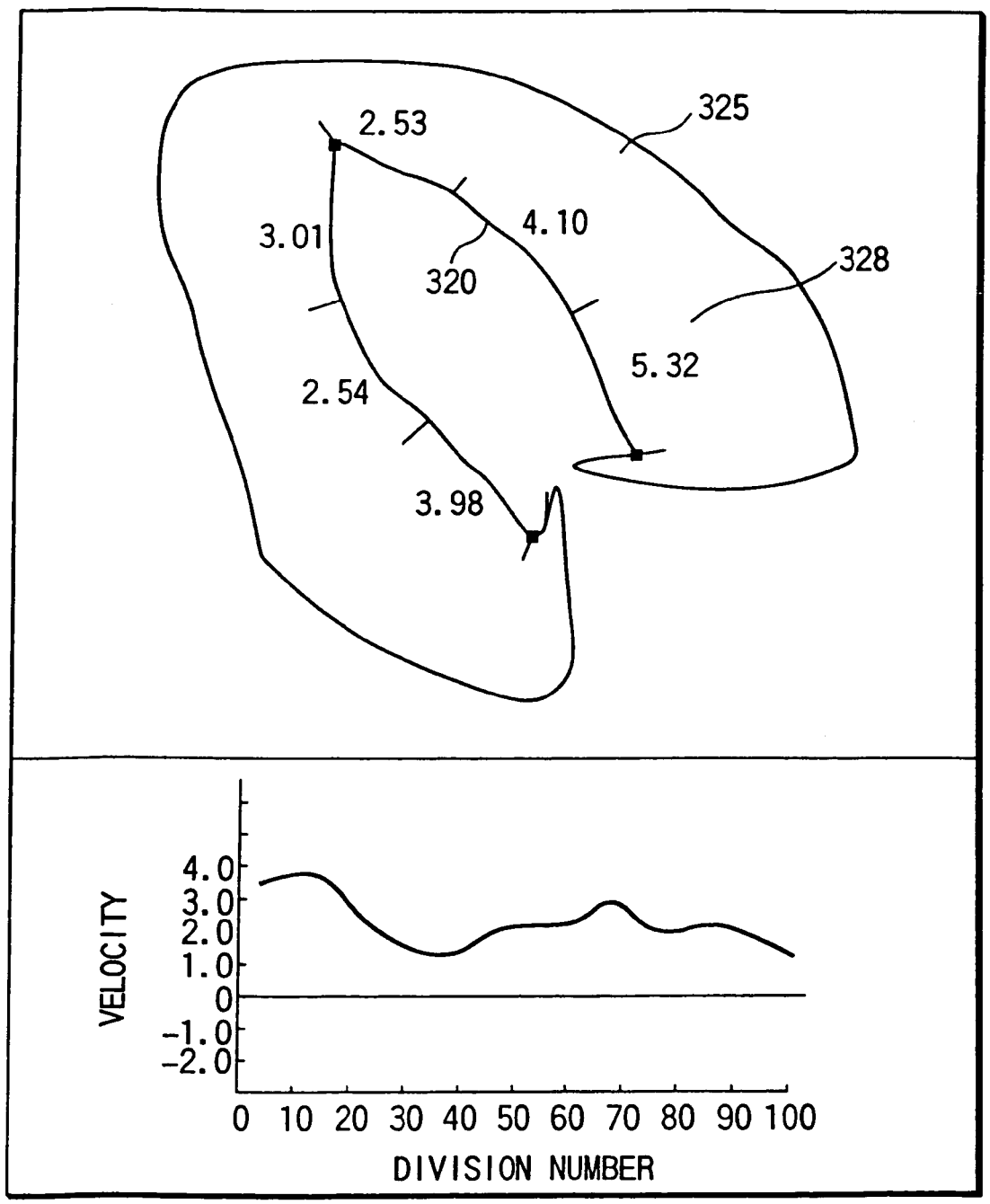
FIG. 67 is an explanatory diagram of a display method in the embodiment of FIGS. 65 and 66.

The calculated averages in the respective regions are displayed by means of graph display, numerical display or color display of the cardiac wall portions as in the case of the second embodiment (see FIG. 67).

As described above, the cardiac apex and the annulus valva having shapes of definite characters are used as characteristic points serving as reference points for dividing the cardiac wall. Based on these characteristic points, the cardiac wall contours are classified into a plurality of parts and velocity information based on Doppler information is obtained for every classified part, thereby displaying an picture reflecting the obtained velocity information for every cardiac wall contour part. As a result, velocity information about the cardiac wall is displayed for every appropriately classified cardiac wall part. Thus, it is possible to display information useful for the analysis of the cardiac function and to greatly contribute to the diagnosis of the cardiac function.

In the meantime, in the display method based on velocity information, there are cases where differences in the velocities of the cardiac wall parts cannot be observed very clearly if the differences are small, and analysis is therefore difficult to make. In considering this, description will be now given to another embodiment.

In this embodiment, cardiac wall contours are divided into a plurality of parts, velocity information based on Doppler information is obtained for every part, a dynamic range of the obtained velocity information is obtained to thereby change colors within the dynamic range. By so doing, if a picture reflecting every cardiac wall contour part is displayed, colors are allotted in accordance with the dynamic range of velocities. As a result, even if differences in velocities of divided parts are small, they can be clearly observed.

Figure 68:
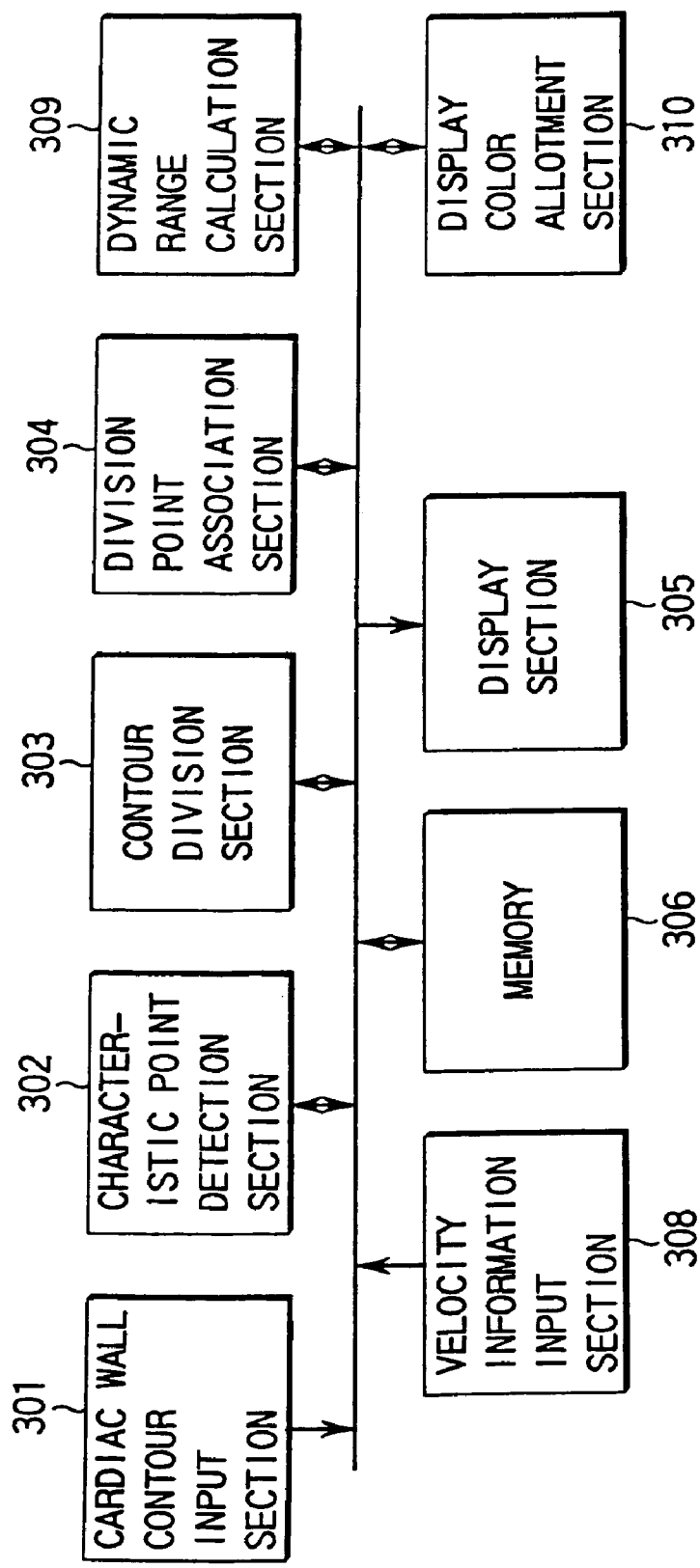
FIG. 68 is a block diagram of the cardiac function analysis support apparatus in an embodiment according to the present invention.

As shown in FIG. 68, the apparatus in this embodiment comprises a cardiac wall contour input section 301 for inputting cardiac wall contour information, a characteristic point detection section 302 for detecting or inputting characteristic points on contours such as a cardiac apex and an annulus valva, a contour division section 303 for dividing cardiac wall contours based on the characteristic points, a division point association section 304 for associating division points in a plurality of time phases, a display section 305 for classifying the divided cardiac wall contours into a plurality of parts useful for diagnosis and for displaying them by means of at least one of numerical display, graph display and color display of the cardiac wall, a memory 306 for storing contour information or division point information, a velocity information input section 308 for inputting velocity information from Doppler signals in the ultrasonic diagnosis apparatus, a dynamic range detection section 309 for detecting a dynamic range and a display color allotment section 310 for allotting display colors.

That is, the structure of the embodiment in FIG. 65 is characterized by comprising the dynamic range detection section 309 and the display color allotment section 310.

The processing by the apparatus of FIG. 68 will be described with reference to the flowchart of FIG. 69.

Figure 69:
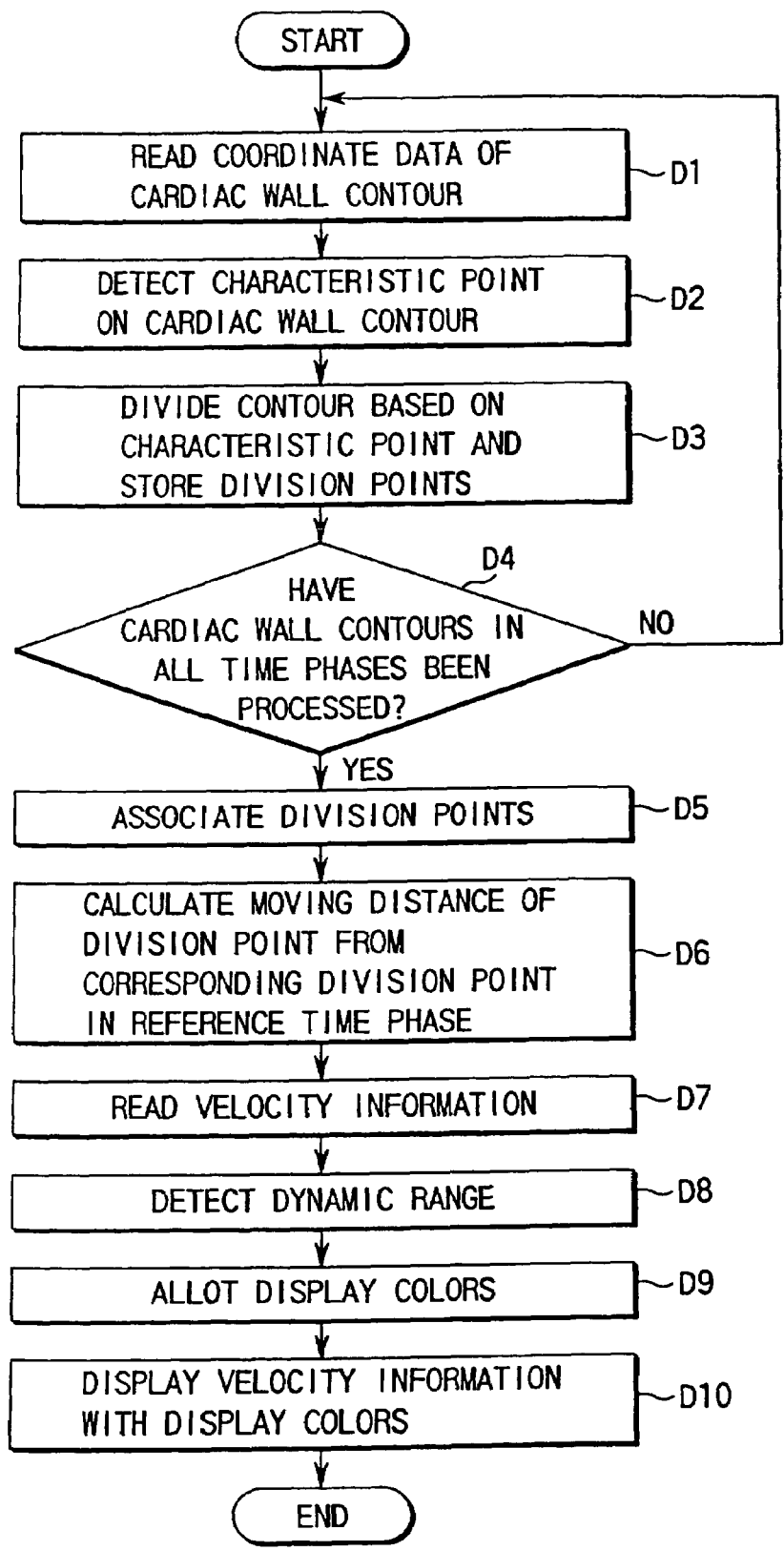
FIG. 69 is a flowchart for describing a processing flow of the cardiac function analysis support method in the embodiment of FIG. 68.

In the apparatus of this embodiment, inputted cardiac wall contours in respective time phases are divided into a plurality of parts based on characteristic points such as a cardiac apex and an annulus valva and the divided parts of pictures in a plurality of time phases are associated with one another (in steps D1 to D5 of FIG. 69). The processing steps are the same as those in the embodiment of FIG. 51.

After dividing the cardiac wall contours, movement distances of divided parts from the corresponding divided parts in the reference time phase are calculated, respectively, which processing steps are also the same as those in the embodiment of FIG. 51 (Step D6 of FIG. 68).

Next, velocity information obtained from Doppler signals is inputted (Step D7 of FIG. 68). The input step is conducted by, for example, obtaining Doppler signals of the heart using an ultrasonic diagnosis apparatus having a Doppler signal measurement function, obtaining velocity information at the velocity information input section 308 and inputting the velocity information.

Thereafter, the dynamic range detection section 309 detects dynamic ranges of movement distances of respective division points (Step D8 of FIG. 69). This is done by, for example, calculating differential values D'j,n of movement distances of respective division points in a plurality of time phases or one time phase and detecting a maximum value Vmax and a minimum value Vmin from the calculated differential values D'j, n as follows:

$$V\max = \max(D'j,n) \quad (16)$$

$$V\min = \min(D'j,n). \quad (17)$$

After completing the processing at the dynamic range detection section 309, display colors are allotted to the Vmin and Vmax (Step D9 of FIG. 69). The display colors are allotted by formula (18) by which a color phase Cj,n of the display color on the n-th division point of the j-th time phase picture is defined by a dynamic range, as follows:

$$C_{j,n}(°) = \mathrm{Mod}\left(k \cdot \frac{D'_{j,n} - V_{\min}}{V_{\max} - V_{\min}} + V_{\min}, 360\right) \quad (18)$$

Here, "(°)" in Cj, n (°) indicates that CJ,n expresses an angle.

The processing as expressed by the formula (18) is conducted by the display color allotment section 100, thereby completing allotting display colors.

Finally, the display section 305 displays velocity information on the picture by using the allotted display colors (Step D10 of FIG. 68).

By so doing, even if velocity distribution is small, it is possible to display velocity information using many colors. This is useful in diagnosing differences in cardiac wall portions in detail. In the display method based on velocity information, there are cases where differences in movement state cannot be observed very clearly if rate differences are small among cardiac wall portions, and therefore analysis is difficult to make. In the fourth embodiment, cardiac wall contours are divided into a plurality of parts and velocity information based on Doppler information is obtained for respective divided parts, the dynamic range of the resultant velocity information is obtained and colors are changed within the dynamic range. As a result, if an picture reflecting the respective parts of the cardiac wall contours is displayed, it is possible to display the picture while allotting colors there is only a little difference in velocity, it is possible to display the picture while clarifying velocity differences among the respective parts. Thus, in the analysis of the movement function, the present invention can provide an analysis support apparatus and an analysis support method capable of grasping the movement function clearly.

The methods shown in FIGS. 52, 61, 66 and 68 can be stored as programs executed by a computer in a storage medium including a magnetic disc (such as a floppy disc and a hard disc) and an optical disc (such as a CD-ROM and a DVD) and can be distributed widely.

According to the present invention described so far, cardiac wall parts in various time phases can be appropriately associated in the analysis of movement state of a cardiac wall by a plurality of time phase pictures. Using the division of cardiac wall contours, cardiac wall parts are classified by a method suitable for a diagnosis, whereby information useful for analysis can be displayed. Thus, the present invention can provide a cardiac function analysis support apparatus and a cardiac function analysis support method capable of greatly contributing to the cardiac function analysis.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

The invention claimed is:

1. An ultrasonic image processing method for extracting, from an ultrasonic moving image including an object moving periodically, an amount of movement of the moving image other than movement of the object in the ultrasonic moving image, comprising:

dividing the input ultrasonic moving image in a time period equal to a movement cycle of the object, and extracting an outline of the object from each of a plurality of frames of the ultrasonic moving image in each time period of a plurality of consecutive time periods to acquire time-series data representing movement of the outline in the time period; and acquiring time-series comparison data representing a difference in movement of the outline in every time period based on a difference between the time-series data in two adjacent time periods.

2. The method according to claim 1, including comparing the comparison data in every time period with reference data previously set for determining an useful moving image, and determining, as the useful moving image, the frames in the time periods where both the comparison result and the difference in movement of the outlines are smaller than those of the other frames.

3. An ultrasonic image processing method for extracting, from an ultrasonic moving image including an object moving periodically, an amount of movement of the moving image other than movement of the object in the ultrasonic moving image, comprising:

dividing the input ultrasonic moving image in a time period equal to a movement cycle of the object, and dividing, into a plurality of partial outlines, an outline of the object extracted from each of a plurality of frames of the ultrasonic moving image in each time period of a plurality of consecutive time periods to acquire time-series data representing movement of each of the partial outlines in the time period;

acquiring time-series comparison data representing a difference in movement of each of the partial outlines for each of the time periods, based on a difference between the time-series data of the plurality of partial outlines in two adjacent time periods; and calculating an average of respective comparison data of the plurality of partial outlines for each of the time periods.

4. The method according to claim 3, including comparing the average of respective comparison data of the plurality of partial outlines in each of the time periods with reference data previously set for determining a useful moving image, and determining, as the useful moving image, the frames in the time periods where both the comparison result and the difference in movement of the partial outline are smaller than those of the other frames.

5. The method according to claim 2, including recording the ultrasonic moving image determined as the useful moving image on a recording medium.

6. An ultrasonic image processing apparatus of extracting, from an ultrasonic moving image including an object moving periodically, an amount of movement of the moving image other than movement of the object in the ultrasonic moving image, comprising:

an extraction unit configured to divide the input ultrasonic moving image in a time period equal to a movement cycle of the object, and extract an outline of the object from each of a plurality of frames of the ultrasonic moving image in each time period of a plurality of consecutive time periods;

a first acquisition unit configured to acquire time-series data representing movement of the outline extracted from each frame in the time period; and a second acquisition unit configured to acquire time-series comparison data representing a difference in movement of the outline in every time period based on a difference between the time-series data in two adjacent time periods.

7. The apparatus according to claim 6, including a comparison unit configured to compare the comparison data in every time period with reference data previously set for determining an useful moving image, and a determination unit configured to determine, as the useful moving image, the frames in the time periods where both the comparison result and the difference in movement of the outline are smaller than those of the other frames.

8. An ultrasonic image processing apparatus of extracting, from an ultrasonic moving image including an object moving periodically, an amount of movement of the moving image other than movement of the object in the ultrasonic moving image, comprising:

an extraction unit configured to divide the input ultrasonic moving image in a time period equal to a movement cycle of the object, and extract an outline of the object from each of a plurality of frames of the ultrasonic moving image in each time period of a plurality of consecutive time periods;

an division unit configured to divide the outline of the object extracted from each frame in the time period into a plurality of partial outlines, and acquire time-series data representing movement of each partial outline in the time period;

an acquisition unit configured to acquire time-series comparison data representing a difference in movement of each of the partial outlines for each of the time periods, based on a difference between the time-series data of the plurality of partial outlines in two adjacent time periods; and a calculation unit configured to calculate an average of respective comparison data of the plurality of partial outlines for each of the time periods.

9. The apparatus according to claim 8, including a comparison unit configured to compare the average of respective comparison data of the plurality of partial outlines in each of the time periods with reference data previously set for determining a useful moving image, and a determination unit configured to determine, as the useful moving image, the frames in the time periods where both the comparison result and the difference in movement of the partial outline are smaller than those of the other frames.

10. The apparatus according to claim 9, including a record unit configured to record the ultrasonic moving image determined as the useful moving image on a recording medium.

* * * * *

UNITED STATES PATENT AND TRADEMARK OFFICE
CERTIFICATE OF CORRECTION

PATENT NO.         : 7,460,698 B2                                              Page 1 of 1
APPLICATION NO.    : 11/026015
DATED              : December 2, 2008
INVENTOR(S)        : Yoshioka et al.

It is certified that error appears in the above-identified patent and that said Letters Patent is hereby corrected as shown below:

On the title page, Item (60), the Related U.S. Application Data is incorrect. Item (60) should read:

-- Related U.S. Application Data

(60) Division of application No. 09/778,097, filed on Feb. 7, 2001, now Pat. No. 6,859,548, which is a division of application No. 08/937,007, filed on Sep. 24, 1997, now abandoned. --

Signed and Sealed this

Seventeenth Day of February, 2009

JOHN DOLL
*Acting Director of the United States Patent and Trademark Office*